United States Patent
Thomas et al.

(10) Patent No.: US 9,017,697 B2
(45) Date of Patent: Apr. 28, 2015

(54) COMPOSITIONS AND METHODS FOR MODULATING IMMUNE RESPONSES

(75) Inventors: Ranjeny Thomas, Hawthorne (AU); Nigel Meredith Davies, Nodinge (SE); Brendan John O'Sullivan, Brisbane (AU)

(73) Assignee: The University of Queensland, St. Lucia, Queensland (AU)

( * ) Notice: Subject to any disclaimer, the term of this patent is extended or adjusted under 35 U.S.C. 154(b) by 1347 days.

(21) Appl. No.: 12/444,790

(22) PCT Filed: Oct. 12, 2007

(86) PCT No.: PCT/AU2007/001555
§ 371 (c)(1),
(2), (4) Date: Feb. 9, 2010

(87) PCT Pub. No.: WO2008/043157
PCT Pub. Date: Apr. 17, 2008

(65) Prior Publication Data
US 2010/0151000 A1 Jun. 17, 2010

Related U.S. Application Data

(60) Provisional application No. 60/853,814, filed on Oct. 24, 2006.

(30) Foreign Application Priority Data

Oct. 12, 2006 (AU) ................. 2006905674

(51) Int. Cl.
*A61K 9/127* (2006.01)
*A61K 39/00* (2006.01)
*A61K 39/35* (2006.01)
*A61K 39/39* (2006.01)

(52) U.S. Cl.
CPC ............. *A61K 9/127* (2013.01); *A61K 39/0008* (2013.01); *A61K 39/001* (2013.01); *A61K 39/35* (2013.01); *A61K 39/39* (2013.01); *A61K 2039/55511* (2013.01); *A61K 2039/55522* (2013.01); *A61K 2039/55555* (2013.01); *A61K 2039/55566* (2013.01)

(58) Field of Classification Search
None
See application file for complete search history.

(56) References Cited

U.S. PATENT DOCUMENTS 7,915,009 B2 * 3/2011 Foxwell et al. .............. 435/69.1

FOREIGN PATENT DOCUMENTS

| WO | WO2004/015056 | 2/2004 |
| WO | WO2004/084927 | 10/2004 |
| WO | WO2005/063201 | 7/2005 |
| WO | WO2008/043157 | 4/2008 |

OTHER PUBLICATIONS

J.L Atwood, J.W Steed, Encyclopedia of Supramolecular Chemistry, CRC Press 2004 (p. 487).*

Dima, et al., 2001. "Stimulation of mucosal immune response following oral administration of enterotoxigenic *Escherichia coli* Fimbriae (CFA/I) entrapped in liposomes in conjunction with inactivated whole-cell *Vibrio cholerae* vaccine" Rom. Arch. Microbiol. Immunol., T. 60(1):27-54.

Singh, et al., 1998. "Controlled release microparticles as a single dose diphtheria toxoid vaccine: immunogenicity in small animal models" Vaccine. 16(4):346-352.

* cited by examiner

*Primary Examiner* — Jennifer Graser

(57) ABSTRACT

This invention discloses methods and compositions for modulating immune responses, which involve particulate delivery of agents to immune cells, wherein the agents comprise an inhibitor of the NF-κB signaling pathway and an antigen that corresponds to a target antigen. The methods and compositions of the present invention are particularly useful in the treatment or prophylaxis of an undesirable immune response associated with the target antigen, including autoimmune diseases, allergies and transplantation associated diseases.

11 Claims, 8 Drawing Sheets

(A) Intravenous administration (B) Subcutaneous administration (C) Intra peritoneal injection

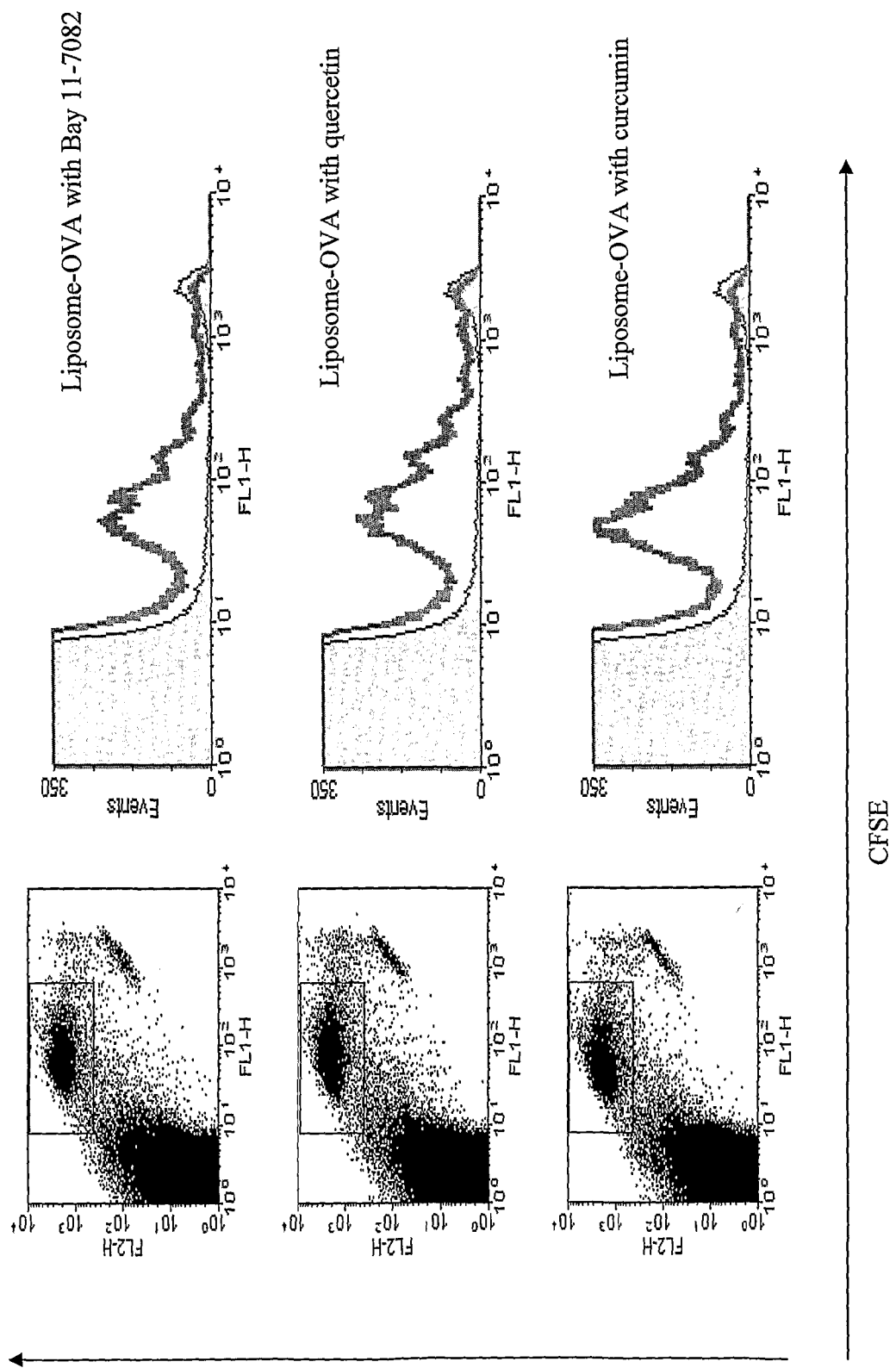
FIGURE 3...cont

COMPOSITIONS AND METHODS FOR MODULATING IMMUNE RESPONSES

This application is a §371 US National Entry of International Application No. PCT/AU2007/001555, filed Oct. 12, 2007, which claims the benefit of U.S. Provisional Application Ser. No. 60/853,814, filed Oct. 24, 2006, and Australian Patent Application No. 2006905674, filed Oct. 12, 2006, each of which is incorporated herein by reference in its entirety.

FIELD OF THE INVENTION

This invention relates generally to methods and compositions for modulating immune responses. More particularly, the present invention relates to the particulate delivery of agents to immune cells, wherein the agents comprise an inhibitor of the NF-κB signaling pathway and an antigen that corresponds to a target antigen. The methods and compositions of the present invention are particularly useful in the treatment or prophylaxis of an undesirable immune response associated with the target antigen, including autoimmune diseases, allergies and transplantation associated diseases.

BACKGROUND OF THE INVENTION

NF-κB transmits signals from the cell surface to the nucleus. Signaling through cell surface receptors to activate NF-κB and MAP kinases through adaptor molecules is of critical importance to survival and activation of all cells in the body, including those regulating innate and adaptive immunity, including antigen-presenting cells such as dendritic cells (DC). As such, NF-κB is a key signaling component in autoimmunity and an attractive target for autoimmune disease therapy.

NF-κB Function

Five NF-κB proteins p50, p52, c-Rel, p65/RelA and RelB are present in mammals. All share a rel homology domain (RHD) that mediates DNA-binding, dimerization and nuclear translocation. p50 and p52 homodimers are transcriptionally inactive, but have the capacity to bind DNA. In contrast, c-rel or Rel A are able to bind DNA and p50 or p52 are able to bind DNA and mediate transcriptional activation. As a result, the availability of subunits and affinity determines the NF-κB composition of the cell (Hoffmann A, Baltimore D: Circuitry of nuclear factor kappaB signaling. Immunol. Rev. (2006) 210:171-186).

In unstimulated cells, NF-κB is present as an inactive form in the cytoplasm bound to inhibitory proteins or IκBs, including IκBα, IκBβ, IκBε, IκBγ, IκBNS, Bcl-3, p100 and p105 (Ghosh S, M: Missing pieces in the NF-kappaB puzzle. Cell (2002) 109 Suppl:S81-96). These proteins contain ankyrin repeats consisting of two tightly packed helices followed by a loop and a tight hairpin turn, which facilitate binding to NF-κB dimers. The NLS region of NF-κB enables dimer nuclear import. IκBβ masks the NLS, preventing nuclear import of dimers. In contrast, IκBα only masks the NLS of p65 and not p50. Nuclear retention is normally prevented by the presence of a nuclear export sequence in IκBα. If this NF-κB export sequence is blocked, RelA/p50 complexes are retained in the nucleus (Huang Tt, Kudo N, Yoshida M, Miyamoto S: A nuclear export signal in the N-terminal regulatory domain of IkappaBalpha controls cytoplasmic localization of inactive NF-kappaB/IkappaBalpha complexes. Proc. Natl. Acad. Sci. U.S.A. (2000) 97(3):1014-1019).

A variety of receptor-ligand pairs activate NF-κB, including TLR/pathogen signals, inflammatory receptors (TNFR/TNF and IL-1R/IL-1), T cell (CD40/CD40L, TCR/MHC peptide) and B cell signals (BAFFR/BAFF, BCR/Ag) and differentiation signals such as lymphotoxin/LTβ and RANK/RANKL. Signaling these pathways leads to activation of serine/threonine kinase IκB kinase (IKK) (Yamamoto Y, Gaynor R B: IkappaB kinases: key regulators of the NF-kappaB pathway. Trends Biochem. Sci. (2004) 29(2):72-79). IKK phosphorylates IκB which is recognized by a specific ubiquitin ligase complex, b-TrCP-SCF. Ubiquitinated IκB is degraded by the 26S proteasome, leading to release of NF-κB, nuclear import and transcriptional activation. The IKK complex consists of 3 subunits including IKKα (IKK1), IKKβ (IKK2) and the associated non-catalytic regulatory subunit IKKγ/NF-κB essential modulator (NEMO). IKK may be activated through phosphorylation by mitogen activated protein kinase kinase kinase (MAPKKK) or NF-κB inducing kinase (NIK), leading to subsequent autophosphorylation of the IKK complex and full activity. IKKβ and NEMO deficient mice have impaired NF-κB activation in response to cytokine and TLR activation, particularly activation of RelA/p50. In contrast, IKKα has a particular role in activation of RelB/p52 complexes and histone phosphorylation to enhance NF-κB DNA binding.

The differential role of IKKα and IKKβ/NEMO in activating distinct NF-κB subunits has led to the classification of the NF-κB pathway into the classical and alternate pathways (referred to collectively herein as "the NF-κB pathway") (Xiao G, Rabson A B, Young W, Qing G, Qu Z: Alternative pathways of NF-kappaB activation: a double-edged sword in health and disease. Cytokine Growth Factor Rev. (2006) 17(4):281-293). The classical pathway is activated by TLR and pro-inflammatory cytokines, leading to IKKβ and NEMO-dependent phosphorylation, degradation of IκB, and subsequent activation of RelA/p50 heterodimers. In the absence of continual signaling the pathway is rapidly shut down, as a result of reduced IKKβ activity and induction of IκB. In contrast the alternate pathway is activated by signals associated with cell differentiation, including LTβ, CD40L and BAFF. RelB/p52 heterodimers are the predominant NF-κB proteins induced, regulated by p100, the precursor to p52, which contains an IκB domain target site for phosphorylation by IKKα. Signal-specific activation of IKKα results in processing of p100 to p52 and activation of RelB/p52. This pathway is characterized by sustained IKKα and long lasting activation of NF-κB. The alternate pathway appears to be an adaptation of the classical NF-κB pathway for cellular differentiation processes and is important in B cell and DC differentiation and lymphoid organogenesis. NIK appears to be an upstream kinase that activates IKKα. NIK, IKKα and RelB knockout mice share similar defects in lymphoid organogenesis. Importantly, there is some overlap in activation of the classical and alternate pathway; for example, LTβ signals both pathways and resulting target genes are activated (Dejardin E, Droin N M, Delhase M et al.: The lymphotoxin-beta receptor induces different patterns of gene expression via two NF-kappaB pathways. Immunity (2002) 17(4):525-535). LPS, a typical classical pathway activator, also leads to activation of the alternate pathway (Mordmuller B, Krappmann D, Esen M, Wegener E, Scheidereit C: Lymphotoxin and lipopolysaccharide induce NF-kappaB-p52 generation by a co-translational mechanism. EMBO Rep. (2003) 4(1):82-87). This may be essential for efficient differentiation of DC, which up-regulate both NF-κB pathways following antigen encounter and migration into the secondary lymphoid organs. Activation of the alternate pathway ensures that although newly synthesized IκBα inhibits RelA/p50, newly synthesized RelB and processing of p100 to p52 leads to dimer replacement or exchange with RelB/p52 and sustained DC differentiation (Saccani S, Pantano S, Natoli G: Modulation of NF-kappaB activity by exchange of dimers. Mol. Cell. (2003) 11(6):1563-1574).

In immune responses, NF-κB target genes are involved in inflammation, cellular organization and differentiation and proliferation. Tissue macrophages are the major source of NF-κB-induced pro-inflammatory cytokines. NF-κB induced cytokines such as TNFα, IL-1 and IL-6 activate innate responses leading to the release of c-reactive protein (CRP) and complement, and up-regulation of adhesion molecules by local endothelial cells. NF-κB-induced chemokines, including IL-8, MIP-1α, MCP-1, RANTES and eotaxin, and growth factors such as GM-CSF mobilize and redirect myeloid cells to local tissue. The same set of responses as occurs to infection also occurs in inflammatory autoimmune diseases, such as rheumatoid arthritis (RA) and inflammatory bowel disease (IBD).

NF-κB has a role in lymphoid organogenesis through the induction of the chemokines CXC12, CXCL13, CCL21 and CCL19. NF-κB has a role in many stages of B and T cell differentiation (Claudio E, Brown K, Siebenlist U: NF-kappaB guides the survival and differentiation of developing lymphocytes. Cell Death Differ. (2006) 13(5):697-701) including a role for the alternate pathway in NKT cell development and for the classical and alternate pathways in regulatory T cell (Treg) development (Schmidt-Supprian M, Tian J, Grant E P et al.: Differential dependence of $CD4^+CD25^+$ regulatory and natural killer-like T cells on signals leading to NF-kappaB activation. Proc. Natl. Acad. Sci. U.S.A. (2004) 101(13):4566-4571; Schmidt-Supprian M, Courtois G, Tian J et al.: Mature T cells depend on signaling through the IKK complex. Immunity (2003) 19(3):377-389; Zheng Y, Vig M, Lyons J, Van Parijs L, Beg A A: Combined deficiency of p50 and cRel in $CD4^+$ T cells reveals an essential requirement for nuclear factor kappaB in regulating mature T cell survival and in vivo function. J. Exp. Med. (2003) 197(7):861-874). c-Rel is also required for efficient IL-2 production by naïve T cells (Banerjee D, Liou H C, Sen R: c-Rel-dependent priming of naive T cells by inflammatory cytokines. Immunity (2005) 23(4):445-458) and T reg are critically dependent on IL-2 for post thymic survival (D'Cruz L M, Klein L: Development and function of agonist-induced $CD25^+Foxp3+$ regulatory T cells in the absence of interleukin 2 signaling. Nat. Immunol. (2005) 6(11):1152-1159; Fontenot J D, Rasmussen J P, Gavin M A, Rudensky A Y: A function for interleukin 2 in Foxp3-expressing regulatory T cells. Nat. Immunol. (2005) 6(11): 1142-1151). NF-κB plays an important role in proliferation of lymphocytes as well as non-hematopoetic cells such as synoviocytes, that hyperproliferate in RA. Relevant NF-κB target genes include c-myc, cyclin D1 and anti-apoptotic genes including c-IAP and Bcl-2.

NF-κB in Autoimmune Inflammation

Autoimmune diseases result from a process involving three distinct but related components—a break in self tolerance, development of chronic inflammation in one or several organs, and if ongoing, tissue destruction and its resultant detrimental effects. "Central" tolerance defects are important contributors to spontaneous autoimmune disease. In the fetal and neonatal period, central tolerance is actively maintained in the thymus (Ardavin C: Thymic dendritic cells. Immunol. Today (1997) 18:350-361). During this process, a repertoire of T cells restricted to self-MHC displayed by the thymic cortical epithelium (cTEC) is selected in each individual. In addition, those T cells reactive to self-antigen presented by medullary antigen-presenting cells (APC), which include medullary epithelial cells (mTEC) and medullary dendritic cells (DC), are deleted by negative selection above a threshold of affinity for self antigens presented by those APC (Kappler J W, Roehm N, Marrack P: T cell tolerance by clonal elimination in the thymus. Cell (1987) 49:273-280). Since an affinity threshold applies for central deletion of self-reactive T cells, circulation of low-affinity self-reactive T cells in the periphery is therefore inevitable. Low-level thymic expression and presentation of self-antigens normally expressed by peripheral somatic cells is common. Expression of these antigens is transcriptionally controlled by AIRE, whose expression is in turn controlled by the alternate NF-κB pathway (Anderson M S, Venanzi Es, Klein L et al.: Projection of an immunological self shadow within the thymus by the aire protein. Science (2002) 298(5597):1395-1401). In spontaneous autoimmune models, a variety of defects in the interaction of APC and thymocytes interferes with the normal process of negative selection, thus permitting the release of autoreactive T cells into the periphery, where subsequent environmental events more readily trigger autoimmune disease (Yoshitomi H, Sakaguchi N, Kobayashi K et al.: A role for fungal {beta}-glucans and their receptor Dectin-1 in the induction of autoimmune arthritis in genetically susceptible mice. J. Exp. Med. (2005) 201(6):949-960). Commonly, viral or modified self-antigens, which have not been expressed in the thymus, are presented by peripheral DC to initiate autoimmunity. A number of modified self-antigens have been described in human autoimmune diseases.

Dendritic Cells

It has been proposed that DC are the critical decision making cells in the immune system (Fazekas de St Groth B. The evolution of self-tolerance: a new cell arises to meet the challenge of self-reactivity. Immunol Today. 1998; 19:448-54). Through their role in the generation of central and peripheral tolerance as well as in priming immune responses and stimulation of memory and effector T cells, DC are likely to play essential roles in both the initiation and perpetuation of autoimmunity and autoimmune diseases. However, the understanding of the means by which DC contribute to peripheral tolerance has opened the exciting possibility of harnessing them for antigen-specific immunotherapy of autoimmune diseases and transplantation.

DC are now recognized as essential regulators of both innate and acquired arms of the immune system (Banchereau J, Steinman R M. Dendritic cells and the control of immunity. Nature. 1998 Mar. 19; 392(6673):245-52). They are responsible for the stimulation of naive T lymphocytes, a property that distinguishes them from all other antigen presenting cells (APC). DC are also essential accessory cells in the generation of primary antibody responses (Inaba K, Steinman R M, Van Voorhis W C, Muramatsu S. Dendritic cells are critical accessory cells for thymus-dependent antibody responses in mouse and in man. Proc Natl Acad Sci USA. 1983 October; 80(19): 6041-5) and are powerful enhancers of NK cell cytotoxicity (Kitamura H, Iwakabe K, Yahata T, Nishimura S, Ohta A, Ohmi Y, et al. The natural killer T (NKT) cell ligand alpha-galactosylceramide demonstrates its immunopotentiating effect by inducing interleukin (IL)-12 production by dendritic cells and IL-12 receptor expression on NKT cells. J Exp Med. 1999 Apr. 5; 189(7):1121-8). DC are crucial for the initiation of primary immune responses of both helper and cytotoxic T lymphocytes, and thus act as "nature's adjuvant" (Schuler G, Steinman R M. Dendritic cells as adjuvants for immune-mediated resistance to tumors. J Exp Med. 1997 Oct. 20; 186(8):1183-7). Conversely, DC are also involved in the maintenance of tolerance to antigens. DC contribute to thymic central tolerance and shaping of the T cell repertoire by presenting antigens to T cells and deleting those T cells that exhibit strong autoreactivity (Brocker T. Survival of mature CD4 T lymphocytes is dependent on major histocompatibility complex class II-expressing dendritic cells. J Exp Med. 1997 Oct. 20; 186(8):1223-32). However, DC also play a role in peripheral tolerance. Here, DC contribute by deletion of autoreactive lymphocytes and expansion of the population of regulatory T cells (Treg). Accordingly, DC offer potential utility in protective and therapeutic strategies for tolerance restoration in autoimmune diseases.

DC precursors from the bone marrow migrate via the bloodstream to peripheral tissues where they reside as immature DC. Immature DC efficiently capture invading pathogens and other particulate and soluble antigens (Ag). After Ag uptake, DC rapidly cross the endothelium of lymphatic vessels and migrate to the draining secondary lymphoid organs. Following the uptake of immunogenic Ag and lymphatic migration, DC undergo a process of maturation, which is characterized by downregulation of the capacity to capture Ag and upregulation of Ag processing and presentation, expression of co-stimulatory molecules and altered dendritic morphology (Steinman R M. The dendritic cell system and its role in immunogenicity. *Annu Rev Immunol.* 1991; 9:271-96; Cella M, Sallusto F, Lanzavecchia A. Origin, maturation and antigen presenting function of dendritic cells. Curr Opin Immunol. 1997 February; 9(1):10-6; Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med. 1996 Aug. 1; 184(2):747-52). After presentation of Ag to naive T cells in the T cell area of secondary lymphoid organs, most DC disappear, probably by apoptosis. Thus, under optimal conditions, the same DC sequentially carries out distinct functions such as capture and processing of Ag, Ag presentation to rare, naïve Ag-specific T cells and induction of Ag-specific T cell clonal expansion.

Considering the crucial role of DC in Ag processing and presentation and thus in the regulation of immune reactivity, DC are important directors of immune responsiveness, through the interactions with responding lymphocytes and other accessory cells. Broadly, evidence suggests that under steady state conditions, recruitment of DC precursors into tissues and migration/maturation into secondary lymphoid organs occurs at low rates and may favour tolerance induction. On the other hand, stimulation of immature DC leading to DC maturation and activation may induce a productive immune response (Sallusto F, Lanzavecchia A. Mobilizing dendritic cells for tolerance, priming, and chronic inflammation. J Exp Med. 1999 Feb. 15; 189(4):611-4).

The process of DC maturation can be stimulated by various mechanisms, including pathogen-derived molecules (LPS, DNA, RNA), proinflammatory cytokines (TNFα, IL-1, IL-6), tissue factors such as hyaluronan fragments, migration of DC across endothelial barriers between inflamed tissues and lymphatics, and T cell-derived signals (CD154) (Sparwasser T, Koch E S, Vabulas R M, Heeg K, Lipford G B, Ellwart J W, et al. Bacterial DNA and immunostimulatory CpG oligonucleotides trigger maturation and activation of murine dendritic cells. Eur J. Immunol. 1998 June; 28(6):2045-54; Cella M, Salio M, Sakakibara Y, Langen H, Julkunen I, Lanzavecchia A. Maturation, activation, and protection of dendritic cells induced by double-stranded RNA. J Exp Med. 1999 Mar. 1; 189(5):821-9; De Smedt T, Pajak B, Muraille E, Lespagnard L, Heinen E, De Baetselier P, et al. Regulation of dendritic cell numbers and maturation in vivo by lipopolysaccharide. J Exp Med. 1996 Oct. 1; 184(4):1413-24). In contrast, anti-inflammatory signals, such as IL-10, TGFβ, prostaglandins, and corticosteroids tend to inhibit maturation (De Smedt T, Van Mechelen M, De Becker G, Urbain J, Leo O, Moser M. Effect of interleukin-10 on dendritic cell maturation and function. Eur J. Immunol. 1997 May; 27(5):1229-35; Geissmann F, Revy P, Regnault A, Lepelletier Y, Dy M, Brousse N, et al. TGF-beta 1 prevents the noncognate maturation of human dendritic Langerhans cells. J. Immunol. 1999 Apr. 15; 162(8):4567-75; de Jong E C, Vieira P L, Kalinski P, Kapsenberg M L. Corticosteroids inhibit the production of inflammatory mediators in immature monocyte-derived DC and induce the development of tolerogenic DC3. J Leukoc Biol. 1999 August; 66(2):201-4). Thus, DC represent an attractive therapeutic target, either to enhance or to attenuate immunity for modulation of disease. To date, ex vivo modulation of DC and exposure to antigen before transfer into an animal or human recipient has been the major approach to achieve protective and therapeutic immunity. This relates in part to complexity of the DC system in the context of a whole person with an immune system disorder, and in part to the difficulty of delivery of specific Ags and immunomodulators to DC in vivo.

Role of NF-κB in Regulating DC Function

The ability of a myeloid DC to induce immunity or tolerance is linked to its maturation state and thus to NF-κB activity (Dhodapkar M V, Steinman R M, Krasovsky J, Munz C, Bhardwaj N. Antigen-specific inhibition of effector T cell function in humans after injection of immature dendritic cells. J Exp Med. 2001 Jan. 15; 193(2):233-8; Jonuleit H, Schmitt E, Schuler G, Knop J, Enk A H. Induction of interleukin 10-producing, nonproliferating CD4(+) T cells with regulatory properties by repetitive stimulation with allogeneic immature human dendritic cells. J Exp Med. 2000 Nov. 6; 192(9):1213-22; Lutz M B, Kukutsch N A, Menges M, Rossner S, Schuler G. Culture of bone marrow cells in GM-CSF plus high doses of lipopolysaccharide generates exclusively immature dendritic cells which induce alloantigen-specific CD4 T cell anergy in vitro. Eur J. Immunol. 2000 April; 30(4):1048-52: Mehling A, Grabbe S, Voskort M, Schwarz T, Luger T A, Beissert S. Mycophenolate mofetil impairs the maturation and function of murine dendritic cells. J. Immunol. 2000 Sep. 1; 165(5):2374-81). Immature DC generated from murine BM induce T cell unresponsiveness in vitro and prolonged cardiac allograft survival (Lutz M B, Suri R M, Niimi M, Ogilvie A L, Kukutsch N A, Rossner S, et al. Immature dendritic cells generated with low doses of GM-CSF in the absence of IL-4 are maturation resistant and prolong allograft survival in vivo. Eur J. Immunol. 2000 July; 30(7):1813-22). Various drugs and cytokines, and inhibitors of NF-κB inhibit myeloid DC maturation (de Jong E C, Vieira P L, Kalinski P, Kapsenberg M L. Corticosteroids inhibit the production of inflammatory mediators in immature monocyte-derived DC and induce the development of tolerogenic DC3. J Leukoc Biol. 1999 August; 66(2):201-4; Griffin M D, Lutz W, Phan V A, Bachman L A, McKean D J, Kumar R. Dendritic cell modulation by 1alpha, 25 dihydroxyvitamin D3 and its analogs: a vitamin D receptor-dependent pathway that promotes a persistent state of immaturity in vitro and in vivo. Proc Natl Acad Sci USA. 2001 Jun. 5; 98(12):6800-5; Hackstein H, Morelli A E, Larregina A T, Ganster R W, Papworth G D, Logar A J, et al. Aspirin inhibits in vitro maturation and in vivo immunostimulatory function of murine myeloid dendritic cells. J. Immunol. 2001 Jun. 15; 166(12):7053-62; Lee J I, Ganster R W, Geller D A, Burckart G J, Thomson A W, Lu L. Cyclosporine A inhibits the expression of costimulatory molecules on in vitro-generated dendritic cells: association with reduced nuclear translocation of nuclear factor kappa B. Transplantation. 1999 Nov. 15; 68(9): 1255-63; Steinbrink K, Wolfl M, Jonuleit H, Knop J, Enk A H. Induction of tolerance by IL-10-treated dendritic cells. J.

Immunol. 1997 Nov. 15; 159(10):4772-80; Yoshimura S, Bondeson J, Foxwell B M, Brennan F M, Feldmann M. Effective antigen presentation by dendritic cells is NF-kappaB dependent: coordinate regulation of MHC, co-stimulatory molecules and cytokines. Int Immunol. 2001 May; 13(5): 675-83), including corticosteroids, salicylates, mycophenolate mofetil, transforming growth factor (TGF)-β IL-10. DC generated in the presence of these agents alter T cell function in vitro and in vivo, including promotion of allograft survival (Giannoukakis N, Bonham C A, Qian S, Zhou Z, Peng L, Harnaha J, et al. Prolongation of cardiac allograft survival using dendritic cells treated with NF-κB decoy oligodeoxyribonucleotides. Mol. Ther. 2000; 1(5 Pt 1):430-7; Griffin M D, Lutz W, Phan V A, Bachman L A, McKean D J, Kumar R. Dendritic cell modulation by 1alpha, 25 dihydroxyvitamin D3 and its analogs: a vitamin D receptor-dependent pathway that promotes a persistent state of immaturity in vitro and in vivo. Proc Natl Acad Sci USA. 2001; 98(12):6800-5; Rea D, van Kooten C, van Meijgaarden K E, Ottenhoff T H, Melief C J, Offringa R. Glucocorticoids transform CD40-triggering of dendritic cells into an alternative activation pathway resulting in antigen-presenting cells that secrete IL-10. Blood. 2000 May 15; 95(10):3162-7; Adorini L, Penna G, Giarratana N, Uskokovic M. Tolerogenic dendritic cells induced by vitamin D receptor ligands enhance regulatory T cells inhibiting allograft rejection and autoimmune diseases. J Cell Biochem. 2003 Feb. 1; 88(2):227-33). NF-κB activity leads to transcription of a number of genes involved in the immune response. In particular, RelB activity is required for myeloid DC differentiation (Burkly L, Hession C, Ogata L, Reilly C, Marconi L A, Olson D, et al. Expression of relB is required for the development of thymic medulla and dendritic cells. Nature. 1995 Feb. 9; 373(6514):531-6; Weih F, Carrasco D, Durham S K, Barton D S, Rizzo C A, Ryseck R P, et al. Multiorgan inflammation and hematopoietic abnormalities in mice with a targeted disruption of RelB, a member of the NF-kappa B/Rel family. Cell. 1995; 80(2):331-40; Wu L, D'Amico A, Winkel K D, Suter M, Lo D, Shortman K. RelB is essential for the development of myeloid-related CD8alpha-dendritic cells but not of lymphoid-related CD8alpha+ dendritic cells. Immunity. 1998 December; 9(6): 839-47). RelB regulates DC and B cell APC function through regulation of CD40 and MHC molecule expression (O'Sullivan B J, MacDonald K P, Pettit A R, Thomas R. RelB nuclear translocation regulates B cell MHC molecule, CD40 expression, and antigen-presenting cell function. Proc Natl Acad Sci USA. 2000 Oct. 10; 97(21):11421-6; O'Sullivan B J, Thomas R. CD40 Ligation conditions dendritic cell antigen-presenting function through sustained activation of NF-kappaB. J. Immunol. 2002 Jun. 1; 168(11):5491-8; Martin E, O'Sullivan B, Low P, Thomas R. Antigen-specific suppression of a primed immune response by dendritic cells mediated by regulatory T cells secreting interleukin-10. Immunity. 2003 January; 18(1):155-67). The present inventors have shown that antigen-exposed DC in which RelB function is inhibited lack cell surface CD40, prevent priming of immunity, and suppress previously primed immune responses. While immature DC, which maintain the potential for subsequent activation, were only moderately suppressive of primed immune responses, RelB-deficient DC lacking this potential were much more suppressive (Martin E, O'Sullivan B, Low P, Thomas R. Antigen-specific suppression of a primed immune response by dendritic cells mediated by regulatory T cells secreting interleukin-10. Immunity. 2003 January; 18(1):155-67).

Use of Dendritic Cells for Tolerance

Increasing evidence in humans and rodents strongly suggests that immature or NF-κB-deficient DC may control peripheral tolerance by inducing the differentiation of regulatory T cells (Dhodapkar M V, Steinman R M, Krasovsky J, Munz C, Bhardwaj N. Antigen-specific inhibition of effector T cell function in humans after injection of immature dendritic cells. J Exp Med. 2001 Jan. 15; 193(2):233-8; Jonuleit H, Schmitt E, Schuler G, Knop J, Enk A H. Induction of interleukin 10-producing, nonproliferating CD4(+) T cells with regulatory properties by repetitive stimulation with allogeneic immature human dendritic cells. J Exp Med. 2000 Nov. 6; 192(9):1213-22; Martin E, O'Sullivan B, Low P, Thomas R. Antigen-specific suppression of a primed immune response by dendritic cells mediated by regulatory T cells secreting interleukin-10. Immunity. 2003 January; 18(1):155-67; Roncarolo M G, Levings M K, Traversari C. Differentiation of T regulatory cells by immature dendritic cells. J Exp Med. 2001 Jan. 15; 193(2):F5-9). Thus, repetitive in vitro stimulation of allogeneic human T cells with immature, monocyte-derived dendritic cells leads to the generation of nonproliferating, suppressive, interleukin-10 (IL-10)-producing Treg (Jonuleit H, Schmitt E, Schuler G, Knop J, Enk A H. Induction of interleukin 10-producing, nonproliferating CD4(+) T cells with regulatory properties by repetitive stimulation with allogeneic immature human dendritic cells. J Exp Med. 2000 Nov. 6; 192(9):1213-22). Dhodapkar et al. injected autologous, monocyte-derived immature DC, pulsed with influenza matrix peptide and keyhole limpet hemocyanin, subcutaneously in two human volunteers. They reported an Ag-specific inhibition of CD8$^+$ T-cell killing activity and the appearance of peptide-specific IL-10-producing T cells, accompanied by a decrease in the number of interferon (IFN)-γ-producing T cells (Dhodapkar M V, Steinman R M, Krasovsky J, Munz C, Bhardwaj N. Antigen-specific inhibition of effector T cell function in humans after injection of immature dendritic cells. J Exp Med. 2001 Jan. 15; 193(2):233-8).

CD40 is a key determinant of DC immunogenicity. Inhibition of the RelB transcription factor or of CD40 itself produces regulatory DC that are able to generate IL-10-producing T regulatory cells in vivo (Martin E, O'Sullivan B, Low P, Thomas R. Antigen-specific suppression of a primed immune response by dendritic cells mediated by regulatory T cells secreting interleukin-10. Immunity. 2003 January; 18(1):155-67). Conversely, tumor antigen-specific immunity can be markedly heightened by engineering DC which are able to express CD40 for prolonged periods in vivo (Hanks B A, Jiang J, Singh R A, Song W, Barry M, Huls M H, et al. Re-engineered CD40 receptor enables potent pharmacological activation of dendritic-cell cancer vaccines in vivo. Nat. Med. 2005 February; 11(2):130-7). IL-10 and TGFβ produced by T regulatory cells may contribute to tolerance by limiting expression of MHC class II and co-stimulatory molecules by DC (Jonuleit H, Schmitt E, Schuler G, Knop J, Enk A H. Induction of interleukin 10-producing, nonproliferating CD4(+) T cells with regulatory properties by repetitive stimulation with allogeneic immature human dendritic cells. J Exp Med. 2000 Nov. 6; 192(9):1213-22; Roncarolo M G, Levings M K, Traversari C. Differentiation of T regulatory cells by immature dendritic cells. J Exp Med. 2001 Jan. 15; 193(2): F5-9).

In conjunction with decreased expression of co-stimulatory molecules, expression of ILT3 and ILT4 may be increased by regulatory DC (Chang C C, Ciubotariu R, Manavalan J S, Yuan J, Colovai A I, Piazza F, et al. Tolerization of dendritic cells by T(S) cells: the crucial role of inhibitory receptors ILT3 and ILT4. Nat. Immunol. 2002 March;

3(3):237-43). These Ig-like inhibitory receptors, related to NK cell killer inhibitory receptors (KIR), are upregulated by the APC as a result of interaction with $CD8^+CD28^-$ regulatory T cells. These receptors negatively signal monocytes and DC through immunoreceptor tyrosine-based inhibitory motifs (ITIMs) (Colonna M, Nakajima H, Cella M. A family of inhibitory and activating Ig-like receptors that modulate function of lymphoid and myeloid cells. Semin Immunol. 2000; 12(2):121-7; Colonna M, Navarro F, Bellon T, Llano M, Garcia P, Samaridis J, et al. A common inhibitory receptor for major histocompatibility complex class I molecules on human lymphoid and myelomonocytic cells. J Exp Med. 1997; 186(11):1809-18; Colonna M, Samaridis J, Cella M, Angman L, Allen R L, O'Callaghan C A, et al. Human myelomonocytic cells express an inhibitory receptor for classical and nonclassical MHC class 1 molecules. J. Immunol. 1998; 160(7):3096-100). $CD4^+$ T cell-induced NFκB activation of APC is reduced in the presence of $CD8^+CD28^-$ T cells, potentially through this signaling pathway (Chang C C, Ciubotariu R, Manavalan J S, Yuan J, Colovai A I, Piazza F, et al. Tolerization of dendritic cells by T(S) cells: the crucial role of inhibitory receptors ILT3 and ILT4. Nat. Immunol. 2002; 3(3):237-43).

IL-10 is an important cytokine involved in the generation of regulatory T cells by DC. Treatment of DC with IL-10 can convert immature DC into regulatory DC by suppressing NF-κB and therefore arresting maturation. This drives the differentiation of IL-10 producing T regulatory type 1-producing cells in vitro and in vivo (Steinbrink K, Wolfl M, Jonuleit H, Knop J, Enk A H. Induction of tolerance by IL-10-treated dendritic cells. J. Immunol. 1997 Nov. 15; 159 (10):4772-80; Steinbrink K, Jonuleit H, Muller G, Schuler G, Knop J, Enk A H. Interleukin-10-treated human dendritic cells induce a melanoma-antigen-specific anergy in CD8(+) T cells resulting in a failure to lyse tumor cells. Blood. 1999 Mar. 1; 93(5):1634-42; Liu L, Rich B E, Inobe J, Chen W, Weiner H L. Induction of Th2 cell differentiation in the primary immune response: dendritic cells isolated from adherent cell culture treated with IL-10 prime naive $CD4^+$ T cells to secrete IL-4. Int Immunol. 1998 August; 10(8):1017-26). Human DC exposed to IL-10 induce a state of antigen-specific anergy in $CD4^+$ T cells and CD8+ T cells by similarly converting DC into an immuoregulatory state (104). IL-10 inhibits IL-12 production and co-stimulatory molecule expression by DC, giving rise to regulatory DC (Kalinski P, Hilkens C M, Wierenga E A, Kapsenberg M L. T-cell priming by type-1 and type-2 polarized dendritic cells: the concept of a third signal. Immunol Today. 1999 December; 20(12):561-7).

DC could also be manipulated in situ to induce peripheral tolerance. For example Flt3L, a growth factor that expands DC, enhanced the induction of oral tolerance in vivo (Viney J L, Mowat A M, O'Malley J M, Williamson E, Fanger N A. Expanding dendritic cells in vivo enhances the induction of oral tolerance. J. Immunol. 1998 Jun. 15; 160(12):5815-25). By contrast, treatment with Flt-3L increased severity of experimental autoimmune thyroiditis due to enhanced Th1 responses, while GM-CSF either prevented or significantly suppressed disease development even at a late stage, due to enhanced Th2 responses (Vasu C, Dogan R N, Holterman M J, Prabhakar B S. Selective induction of dendritic cells using granulocyte macrophage-colony stimulating factor, but not fms-like tyrosine kinase receptor 3-ligand, activates thyroglobulin-specific $CD4^+/CD25^+$ T cells and suppresses experimental autoimmune thyroiditis. J. Immunol. 2003 Jun. 1; 170(11):5511-22).

Several procedures to induce tolerance have been developed using either DC modified as just described, or different routes of DC administration. For example, subcutaneous (sc) injection of antigen-pulsed splenic DC or epidermal Langerhans cells induces antigen-specific immunity, whereas intravenous (iv) injections of the same preparation result in tolerance (Morikawa Y, Furotani M, Kuribayashi K, Matsuura N, Kakudo K. The role of antigen-presenting cells in the regulation of delayed-type hypersensitivity. I. Spleen dendritic cells. Immunology. 1992 September; 77(1):81-7; Morikawa Y, Furotani M, Matsuura N, Kakudo K. The role of antigen-presenting cells in the regulation of delayed-type hypersensitivity. II. Epidermal Langerhans' cells and peritoneal exudate macrophages. Cell Immunol. 1993 November; 152(1): 200-10). Specific strategies for autoimmune diseases might include promotion of regulatory T cell development using regulatory DC, or genetic engineering of DC to introduce molecules that have immunosuppressive functions, such as IL-10, TGFβ, Fas-ligand, ILT3 and ILT4. Evidence for the ability of DC to suppress autoimmune inflammatory disease so far comes from the application of DC to models of autoimmune disease, as detailed below. Syngeneic DC, with or without exposure to autoantigens have been shown to inhibit the development of autoimmune diseases of the neuromuscular system, such as experimental allergic encephalomyelitis (EAE), autoimmune endocrinopathies, such as type 1 diabetes and models of autoimmune arthritis, such as collagen-induced arthritis.

After exposure to TGFβ in vitro, splenic DC from healthy syngeneic donor rats could transfer suppression to recipients with EAE. In contrast, TGFβ-exposed DC from donor rats with EAE had no effect when transferred. DC were administered 5 days after immunization of Lewis rats with encephalitogenic myelin basic protein peptide 68-86 (MBP68-86) and complete Freund's adjuvant (CFA), during the incipient phase of EAE (Huang Y M, Yang J S, Xu L Y, Link H, Xiao B G. Autoantigen-pulsed dendritic cells induce tolerance to experimental allergic encephalomyelitis (EAE) in Lewis rats. Clin Exp Immunol. 2000 December; 122(3):437-44). Sc injection of immature, but not lipopolysaccharide (LPS)-treated, bone marrow (BM)-derived DC prior to immunization also prevented EAE (Xiao B G, Huang Y M, Yang J S, Xu L Y, Link H. Bone marrow-derived dendritic cells from experimental allergic encephalomyelitis induce immune tolerance to EAE in Lewis rats. Clin Exp Immunol. 2001 August; 125(2):300-9). TGFβ-modified DC similarly inhibited the development of clinical signs of experimental autoimmune myasthenia gravis (EAMG) in Lewis rats when given during the incipient phase of EAMG (Yarilin D, Duan R, Huang Y M, Xiao B G. Dendritic cells exposed in vitro to TGF-beta1 ameliorate experimental autoimmune myasthenia gravis. Clin Exp Immunol. 2002 February; 127(2):214-9).

In autoimmune disease of the eye, peptide-loaded immature DC inhibited the production of IFN-γ by uveitogenic T cells and therefore the induction of experimental autoimmune uveo-retinitis (EAU) in vivo (Jiang H R, Muckersie E, Robertson M, Forrester J V. Antigen-specific inhibition of experimental autoimmune uveoretinitis by bone marrow-derived immature dendritic cells. Invest Opthalmol V is Sci. 2003 April; 44(4):1598-607). Draining lymph node T cells secreted high levels of IL-10 and IL-15. In another model, transfer of inter-photoreceptor retinoid binding protein-pulsed $TGFβ_2$-treated APC to inter-photoreceptor retinoid binding protein-immunized mice successfully suppressed the induction of experimental uveoretinitis in mice (Okamoto S, Kosiewicz M, Caspi R, Streilein J. ACAID as a potential therapy for establishmental autoimmune uveitis. In: Science E, editor. Advances in Ocular Immunology. Amsterdam; 1994).

Myelin antigen-pulsed splenocytes were shown to suppress EAE by selective induction of anergy in encephalitogenic T cells (Vandenbark A A, Celnik B, Vainiene M, Miller S D, Offner H. Myelin antigen-coupled splenocytes suppress experimental autoimmune encephalomyelitis in Lewis rats through a partially reversible anergy mechanism. J. Immunol. 1995 Dec. 15; 155(12):5861-7). Regulatory APC, generated by exposure to TGFb2 and MBP Ag, promoted development of $CD8^+$ Treg that suppressed EAE (Faunce D E, Terajewicz A, Stein-Streilein J. Cutting edge: in vitro-generated tolerogenic APC induce CD8+ T regulatory cells that can suppress ongoing experimental autoimmune encephalomyelitis. J. Immunol. 2004 Feb. 15; 172(4):1991-5): These results provide evidence that DC can induce tolerance in experimental autoimmune diseases through effects on responding T cells. In alternative approach, EAE could be prevented by iv injection of splenic DC exposed ex vivo to MBP and CTLA-4-Ig fusion protein, presumably through ex vivo blockade of CD28-CD80 interactions (Khoury S J, Gallon L, Verburg R R, Chandraker A, Peach R, Linsley P S, et al. Ex vivo treatment of antigen-presenting cells with CTLA4Ig and encephalitogenic peptide prevents experimental autoimmune encephalomyelitis in the Lewis rat. J. Immunol. 1996 Oct. 15; 157(8):3700-5).

In a number of models, repetitive intravenous administration of so-called "semimature" DC, prepared in vitro by exposure to tumor necrosis factor TNF-α, induced Ag-specific protection. TNF-α-DC have been shown to express high levels of MHC and T cell co-stimulatory molecules, but unlike mature DC, they produce low levels of pro-inflammatory cytokines and are unable to secrete IL-12p70. These DC suppress EAE through generation of autoantigen-specific IL-10-secreting $CD4^+$ T cells (Menges M, Rossner S, Voigtlander C, Schindler H, Kukutsch N A, Bogdan C, et al. Repetitive injections of dendritic cells matured with tumor necrosis factor alpha induce antigen-specific protection of mice from autoimmunity. J Exp Med. 2002 Jan. 7; 195(1):15-21), possibly as a result of the lack of expression of co-stimulatory "signal 3" (Thomas R. Signal 3 and its role in autoimmunity. Arthritis Res Ther. 2004; 6:26-7). Finally, DC exposed to $TGF-\beta_1$ or IFN-γ suppressed the onset and relapses of EAE, in comparison with animals receiving untreated DC or saline injections (Xiao B G, Wu X C, Yang J S, Xu L Y, Liu X, Huang Y M, et al. Therapeutic potential of IFN-gamma-modified dendritic cells in acute and chronic experimental allergic encephalomyelitis. Int Immunol. 2004 January; 16(1):13-22).

In the NOD mouse model of diabetes, transfer of DC treated with IFN-γ also induced long-lasting protection against type 1 diabetes mellitus (Shinomiya M, Fazle Akbar S M, Shinomiya H, Onji M. Transfer of dendritic cells (DC) ex vivo stimulated with interferon-gamma (IFN-gamma) downmodulates autoimmune diabetes in non-obese diabetic (NOD) mice. Clin Exp Immunol. 1999 July; 117(1):38-43). Transfer of pancreatic lymph node DC also suppressed the development of diabetes by the induction of regulatory cells in NOD mice (Clare-Salzler M J, Brooks J, Chai A, Van Herle K, Anderson C. Prevention of diabetes in nonobese diabetic mice by dendritic cell transfer. J Clin Invest. 1992 September; 90(3):741-8). In other experiments, a single iv injection of syngeneic splenic DC from euglycemic NOD mice exposed to human IgG protected mice from diabetes. Supernatants of islets from these mice contained increased levels of IL-4 and IL-10 and diminished levels of IFN-γ compared with diabetic controls, suggesting a favorable effect of type 2 cytokines on disease (Papaccio G, Nicoletti F, Pisanti F A, Bendtzen K, Galdieri M. Prevention of spontaneous autoimmune diabetes in NOD mice by transferring in vitro antigen-pulsed syngeneic dendritic cells. Endocrinology. 2000 April; 141 (4): 1500-5).

Mature BM-derived DC could also prevent diabetes development in NOD mice, an effect ascribed to the generation of $CD25^+CD4^+$ regulatory T cells, secreting Th2 cytokines (Feili-Hariri M, Dong X, Alber S M, Watkins S C, Salter R D, Morel P A. Immunotherapy of NOD mice with bone marrow-derived dendritic cells. Diabetes. 1999 December; 48(12): 2300-8). BM-derived DC generated in the presence of NF-κB inhibitory oligo-dinucleotides or the soluble NF-κB inhibitor Bay11-7082 could also prevent diabetes (Ma L, Qian S, Liang X, Wang L, Woodward J E, Giannoukakis N, et al. Prevention of diabetes in NOD mice by administration of dendritic cells deficient in nuclear transcription factor-kappaB activity. Diabetes. 2003 August; 52(8):1976-85). However, no studies have demonstrated that transferred DC can ameliorate established type 1 diabetes in NOD mice.

Experimental autoimmune thyroiditis (EAT), a murine model of Hashimoto's thyroiditis in humans, can be induced upon challenge of susceptible animals with thyroglobulin and adjuvant (Charreire J. Immune mechanisms in autoimmune thyroiditis. Adv Immunol. 1989; 46:263-334). This disease is mediated by $CD4^+$ T cells and is characterized by lymphocytic infiltration of the thyroid gland (Weetman A P, McGregor A M. Autoimmune thyroid disease: further developments in our understanding. Endocr Rev. 1994 December; 15(6): 788-830). DC exposed to TNFα and Ag induced Ag-specific $CD4^+CD25^+$ T cells with the ability to inhibit development of EAT, confirming results previously published in a model of EAE (Verginis P, Li H S, Carayanniotis G. Tolerogenic semimature dendritic cells suppress experimental autoimmune thyroiditis by activation of thyroglobulin-specific $CD4^+$ $CD25^+$ T cells. J. Immunol. 2005 Jun. 1; 174(11):7433-9).

Several studies in experimental arthritis have evaluated the therapeutic effect of DC transduced with various immunomodulatory genes. Transduction of DC with TNF-related apoptosis-induced ligand (TRAIL) was evaluated in mice with collagen-induced arthritis (CIA). TRAIL expression was controlled by a doxycycline-inducible tetracycline response element. Transfected DC were capable of inducing apoptosis of arthritogenic T cells (Liu Z, Xu X, Hsu H C, Tousson A, Yang P A, Wu Q, et al. CII-DC-AdTRAIL cell gene therapy inhibits infiltration of CII-reactive T cells and CII-induced arthritis. J Clin Invest. 2003 November; 112(9): 1332-41). Genetic modification of primary DC to express Fas-L eliminated or reduced the number of antigen-specific T cells responsible for the progression of CIA (Kim S H, Kim S, Oligino T J, Robbins P D. Effective treatment of established mouse collagen-induced arthritis by systemic administration of dendritic cells genetically modified to express FasL. Mol. Ther. 2002 November; 6(5):584-90). Moreover, DC transfected with Fas-L could induce antigen-specific tolerance after exposure to a peptide to which they had previously been sensitized. This observation provides evidence that it may also be possible to delete autoreactive T cells from the repertoire using modified DC (Matsue H, Matsue K, Walters M, Okumura K, Yagita H, Takashima A. Induction of antigen-specific immunosuppression by CD95L cDNA-transfected 'killer' dendritic cells. Nat. Med. 1999 August; 5(8):930-7).

Adoptive transfer of immature DC expressing IL-4 after adenoviral infection, into mice with established CIA suppressed disease for up to 4 weeks (Kim S H, Kim S, Evans C H, Ghivizzani S C, Oligino T, Robbins P D. Effective treatment of established murine collagen-induced arthritis by systemic administration of dendritic cells genetically modified to express IL-4. J. Immunol. 2001 Mar. 1; 166(5):3499-505). Similarly, IL-4-transduced bone marrow derived DC adoptively transferred before disease onset reduced the incidence and severity of murine CIA, whereas IL-4 delivery by retrovirally transduced T cells and NIH 3T3 cells had no effect (Morita Y, Yang J, Gupta R, Shimizu K, Shelden E A, Endres J, et al. Dendritic cells genetically engineered to express IL-4 inhibit murine collagen-induced arthritis. J Clin Invest. 2001 May; 107(10):1275-84). Whereas each of these approaches suppressed Th1-mediated T cell and antibody responses, they typically did not deviate the immune response towards a Th2 type or regulatory response. By contrast, DC generated in the presence of vasoactive intestinal peptide (VIP) were able to suppress CIA in an IL-10 dependent fashion (Chorny A, Gonzalez-Rey E, Fernandez-Martin A, Ganea D, Delgado M. Vasoactive intestinal peptide induces regulatory dendritic cells that can prevent acute graft-versus-host disease while maintain graft-versus-tumor. Blood. 2006 Jan. 17). TNF-DC also suppressed CIA, when delivered i.v. in high doses, in a partially IL-10 dependent manner (Verginis P, Li H S, Carayanniotis G. Tolerogenic semimature dendritic cells suppress experimental autoimmune thyroiditis by activation of thyroglobulin-specific $CD4^+CD25^+$ T cells. J. Immunol. 2005 Jun. 1; 174(11):7433-9). Both TNF-DC and VIP-DC stimulate peripheral conversion of $CD4^+CD25^+$ regulatory T cells and Tr1 type Treg. VIP has been shown to reduce DC NF-κB activation and CD40 expression (Chorny A, Gonzalez-Rey E, Fernandez-Martin A, Ganea D, Delgado M. Vasoactive intestinal peptide induces regulatory dendritic cells that can prevent acute graft-versus-host disease while maintain graft-versus-tumor. Blood. 2006 Jan. 17).

DC immunotherapy has been introduced in the clinic, and has proven to be feasible, non-toxic and effective in some patients with cancer, particularly if the DC have been appropriately activated (Banchereau J, Palucka A K, Dhodapkar M, Burkeholder S, Taquet N, Rolland A, et al. Immune and clinical responses in patients with metastatic melanoma to $CD34^{(+)}$ progenitor-derived dendritic cell vaccine. Cancer Res. 2001 Sep. 1; 61(17):6451-8; Nestle F O, Banchereau J, Hart D. Dendritic cells: On the move from bench to bedside. Nat. Med. 2001 July; 7(7):761-5; Dhodapkar M V, Krasovsky J, Steinman R M, Bhardwaj N. Mature dendritic cells boost functionally superior $CD8^{(+)}$ T-cell in humans without foreign helper epitopes. J Clin Invest. 2000 March; 105(6):R9-R14). In vivo activation and targeting of DC, as well as exploitation of DC to suppress autoimmunity, will expand the application of DC to a wide variety of immune-mediated diseases. However, a number of technical questions also need to be addressed in autoimmune immunotherapy, including the frequency and route of administration, the subset and number of DC to be used, and the concentration and duration of cytokine treatment. For example, while a single iv or sc dose of $0.5 \times 10^6$ DC treated with an NF-κB inhibitor was sufficient to suppress priming or antigen-induced arthritis, TNF-treated DC must be given repeatedly iv in high doses.

Data relating to human DC are scarce, but certain studies have reported encouraging results. Using a human in vitro model system, immature DC exposed to allospecific $CD8^+$ $CD28^-$ T suppressor cells or $CD4^+CD25^+$ Treg exhibited increased surface expression of the inhibitory molecules ILT3 and 4 (Chang C C, Ciubotariu R, Manavalan J S, Yuan J, Colovai A I, Piazza F, et al. Tolerization of dendritic cells by T(S) cells: the crucial role of inhibitory receptors ILT3 and ILT4. Nat. Immunol. 2002 March; 3(3):237-43). These human regulatory DC induced reversible anergy in unprimed or primed T helper cells, promoting the conversion of alloreactive $CD4^+$ T cells to Treg. Human blood $CD4^+CD123^+$ $CD11c^-$ precursor DC can be generated when cultured in the presence of IL-3 (Grouard G, Rissoan M C, Filgueira L, Durand I, Banchereau J, Liu Y J. The enigmatic plasmacytoid T cells develop into dendritic cells with interleukin (IL)-3 and CD40-ligand. J Exp Med. 1997 Mar. 17; 185(6):1101-11; Rissoan M C, Soumelis V, Kadowaki N, Grouard G, Briere F, de Waal Malefyt R, et al. Reciprocal control of T helper cell and dendritic cell differentiation. Science. 1999 Feb. 19; 283 (5405):1183-6; Arpinati M, Green C L, Heimfeld S, Heuser J E, Anasetti C. Granulocyte-colony stimulating factor mobilizes T helper 2-inducing dendritic cells. Blood. 2000 Apr. 15; 95(8):2484-90). After in vitro activation by TNF-α, these DC promoted production of IL-4 and IL-10 by T cells (Rissoan M C, Soumelis V, Kadowaki N, Grouard G, Briere F, de Waal Malefyt R, et al. Reciprocal control of T helper cell and dendritic cell differentiation. Science. 1999 Feb. 19; 283(5405):1183-6). Such DC have potential for the treatment of autoimmune diseases and acute graft-versus-host disease (Liu Y J, Blom B. Introduction: TH2-inducing DC2 for immunotherapy. Blood. 2000 Apr. 15; 95(8):2482-3).

PB monocyte-derived DC, exposed to IFN-β secrete high levels of IL-10 but low levels of IL-12, and suppress IFN-γ production by mononuclear cells (Huang Y M, Hussien Y, Yarilin D, Xiao B G, Liu Y J, Link H. Interferon-beta induces the development of type 2 dendritic cells. Cytokine. 2001 Mar. 7; 13(5):264-71). DC from MS patients treated with IFN-β in vivo produced less IFN-γ and TNF-α than DC from control patients (Huang Y M, Xiao B G, Ozenci V, Kouwenhoven M, Teleshova N, Fredrikson S, et al. Multiple sclerosis is associated with high levels of circulating dendritic cells secreting pro-inflammatory cytokines. J. Neuroimmunol. 1999 Sep. 1; 99(1):82-90). These findings suggest that exposure of DC to IFN-β and IL-10 may curtail the production of pro-inflammatory cytokines, and after re-infusion, such DC may represent a promising direction for therapy of MS. Signaling through NF-κB was also shown to determine the capacity of DC to stimulate T cell proliferation in vitro, in that $CD40^-$ human monocyte-derived DC generated in the presence of an NF-κB inhibitor, signal little T cell proliferation or IFN-γ production (Thompson A G, O'Sullivan B J, Beamish H, Thomas R. T cells signaled by NF-kappa B-dendritic cells are sensitized not anergic to subsequent activation. J. Immunol. 2004 Aug. 1; 173(3):1671-80).

In a human study of two healthy volunteers, in vivo responses to recall antigens were suppressed when normal volunteers were injected with antigen-exposed immature DC (Dhodapkar M V, Steinman R M, Krasovsky J, Munz C, Bhardwaj N. Antigen-specific inhibition of effector T cell function in humans after injection of immature dendritic cells. J Exp Med. 2001 Jan. 15; 193(2):233-8). This effect was linked to the generation of regulatory type $CD4^+$ and $CD8^+$ T cells and the production of IL-10, and is in marked contrast to the active immunity that can be achieved with mature DC. This small study is the only clinical evidence to date illustrating the potential of immature DC as a tool for immunosuppression. However, it is not yet clear whether this potential will translate into patients with immune system defects that have led to the development of spontaneous autoimmune disease.

Patients with systemic lupus erythematosus (SLE) have been shown to display major alterations in DC homeostasis in that plasmacytoid DC are reduced in blood and IFNα-activated monocytes from these patients are effective APC in vitro (Blanco P, Palucka A K, Gill M, Pascual V, Banchereau J. Induction of dendritic cell differentiation by IFN-alpha in systemic lupus erythematosus. Science. 2001; 294(5546): 1540-3). It was speculated that monocyte-derived DC might efficiently capture apoptotic cells and nucleosomes, present in SLE patients' blood and tissues (Amoura Z, Piette J C, Chabre H, Cacoub P, Papo T, Wechsler B, et al. Circulating plasma levels of nucleosomes in patients with systemic lupus erythematosus: correlation with serum antinucleosome antibody titers and absence of clear association with disease activity. Arthritis Rheum. 1997; 40(12):2217-25). In view of the high levels of IFNα in serum, and its detrimental effects in SLE, IFNα is being developed as a potential target for therapeutic intervention in SLE (Vallin H, Blomberg S, Alm G V, Cederblad B, Ronnblom L. Patients with systemic lupus erythematosus (SLE) have a circulating inducer of interferon-alpha (IFN-alpha) production acting on leucocytes resembling immature dendritic cells. Clin Exp Immunol. 1999; 115(1):196-202). IFNα activates not only myeloid cells, including monocytes and myeloid DC, but also plasmacytoid DC themselves, which are enriched in the inflammatory site in SLE skin lesions (Farkas L, Beiske K, Lund-Johansen F, Brandtzaeg P, Jahnsen F L. Plasmacytoid Dendritic Cells (Natural Interferon-alpha/beta-Producing Cells) Accumulate in Cutaneous Lupus Erythematosus Lesions. Am J. Pathol. 2001; 159(1):237-43). Of interest, the RNA components of the Ro 60 and Sm/RNP small ribonucleoprotein autoantigens have recently been shown to act as endogenous adjuvants which stimulate plasmacytoid DC (PDC) maturation and type I IFN production (Kelly K M, Zhuang H, Nacionales D C, Scumpia P O, Lyons R, Akaogi J, et al. "Endogenous adjuvant" activity of the RNA components of lupus autoantigens Sm/RNP and Ro 60. Arthritis Rheum. 2006 Apr. 27; 54(5): 1557-67; Savarese E, Chae O W, Trowitzsch S, Weber G, Kastner B, Akira S, et al. U1 small nuclear ribonucleoprotein immune complexes induce type I interferon in plasmacytoid dendritic cells through TLR7. Blood. 2006 Apr. 15; 107(8): 3229-34; Vollmer J, Tluk S, Schmitz C, Hamm S, Jurk M, Forsbach A, et al. Immune stimulation mediated by autoantigen binding sites within small nuclear RNAs involves Toll-like receptors 7 and 8. J Exp Med. 2005 Dec. 5; 202(11):1575-85). Type I IFN production by PDC can also be triggered in cutaneous LE by UV-light, which stimulates local production of chemokines for T cells and PDC.

Additionally, several investigators have postulated in vivo administration of soluble inhibitors of the NF-κB pathway either by themselves or in combination with soluble antigens to elicit tolerogenic DC for the treatment of autoimmune disease, allergies and graft versus host disease. Illustrative references disclosing this strategy include: U.S. Pat. No. 7,078,027; U.S. Pat. App. Pub. Nos. 2005/032725, 2004/072228, 2004/166095, 2004/166099, 2005/208036, 2004/258688, 2004/265912, 2005/0220854, 2005/0036993 and 2003/0153518; International Publications WO 99/29865, WO 00/61132, WO 03/000199, WO 2004/084927 and WO 2004/084942; and European Pat. App. No. 1 462 111. However, there is no clinical evidence to the knowledge of the present inventors that supports the usefulness of this strategy.

The present invention is predicated in part on the surprising discovery that co-administration of an NF-κB inhibitor and an antigen in vivo when both are in soluble form or when one is soluble and the other is liposome encapsulated, is ineffective in producing a tolerogenic response to the antigen. However, the present inventors have found that strong tolerogenic responses are generated in vivo by administering particles (e.g., liposomes) comprising both an NF-κB inhibitor and an antigen. This discovery has been reduced to practice in the form of particulate, immunomodulating compositions and methods of treating or preventing undesirable or deleterious immune responses, as described hereafter.

SUMMARY OF THE INVENTION

Accordingly, in one aspect, the present invention provides compositions for modulating an immune response, especially an undesirable or deleterious immune response, to a target antigen. These compositions generally comprise an inhibitor of the NF-κB pathway and an antigen that corresponds to at least a portion of the target antigen, wherein the inhibitor and the antigen are in particulate form. Typically, the NF-κB pathway inhibitor and the antigen are contained in one or more particles. In some embodiments, the inhibitor and the antigen are contained in the same particle. In other embodiments, the inhibitor and the antigen are contained in different particles. Desirably, the or each particle is capable of being taken up (e.g., endocytosis or phagocytosis) by an immune cell such as, but not limited to, an antigen presenting cell (e.g., a dendritic cell, macrophage or Langerhans cell). In some embodiments, the particle comprises a matrix, carrier or substrate. Representative particles are suitably dimensioned and include nanoparticles and microparticles. In some embodiments, the particle comprises a lipid matrix or carrier such as a cationic lipid, an anionic lipid, non-ionic and/or a zwitterionic lipid, e.g., polyglyceryl alkyl ethers, sphingolipids or a phospholipid (such as phosphatidylcholine). In specific examples of this type, the particle is liposomal. In other embodiments, the particle comprises a carrier particle, such as a metal particle (e.g., a tungsten, gold, platinum or iridium particle). In still other embodiments, the particle comprises a polymeric matrix or carrier, illustrative examples of which include biocompatible polymeric particles (e.g., particles fabricated with poly(lactide-co-glycolide)). In still other embodiments, the particle comprises a ceramic or inorganic matrix or carrier.

Suitably, the antigen that corresponds to at least a portion of the target antigen is selected from allergens, autoantigens and alloantigens. The antigen may be selected from proteinaceous antigens, lipid antigens, glycolipid antigens and carbohydrate antigens. In some embodiments, the antigen is in a non-nucleic acid form (e.g., from which the antigen is expressible).

In some embodiments, the inhibitor of the NF-κB pathway decreases the level or functional activity of a member of the NF-κB pathway, which is suitably selected from BTK, LYN, BCR Igα, BCR Igβ, Syk, Blnk, PLCγ2, PKCβ, DAG, CARMA1, BCL10, MALT1, PI3K, PIPS, AKT, p38 MAPK, ERK, COT, IKKα, IKKβ, IKKγ, NIK, RelA/p65, P105/p50, c-Rel, RelB, p52, NIK, Leu13, CD81, CD19, CD21 and its ligands in the complement and coagulation cascade, TRAF6, ubiquitin ligase, Tab2, TAK1, NEMO, NOD2, RIP2, Lck, fyn, Zap70, LAT, GRB2, SOS, CD3 zeta, Slp-76, GADS, ITK, PLCγ1, PKCθ, ICOS, CD28, SHP2, SAP, SLAM and 2B4. In illustrative examples of this type, the NF-κB pathway inhibitor decreases the level or functional activity of any one or more of RelA/p65, P105/p50, c-Rel, RelB or p52. In some embodiments, the inhibitor of the NF-κB pathway increases the level or functional activity of a member of the NF-κB pathway, which is suitably selected from SHP1, SHIP, PIR-B, CD22, CD72, FcgRIIB, IκB, P100, CTLA4, PD-1, Cb1, KIR3DL1, KIR3DL2, KIR2DL and Csk. In some embodiments, the NF-κB pathway inhibitor is in a non-nucleic acid form (e.g., from which the inhibitor is expressible).

The particulate compositions as broadly defined above are especially useful for inducing a tolerogenic response including the induction of an anergic response, or the suppression of a future or existing immune response, to a specified antigen or group of antigens. For example, the immune response includes, but is not limited to, a response mediated by immunoglobulin molecules (e.g., IgE) and/or T lymphocytes (e.g., cytotoxic T lymphocytes (CTLs) and T helper lymphocytes). The immune response is typically but not exclusively directed to an antigen selected from a protein antigen, a particulate antigen, an alloantigen, an autoantigen, an allergen, a bacterial antigen, a viral antigen, a parasitic antigen or an immune complex.

In some embodiments, the composition may further comprise a pharmaceutically acceptable carrier or diluent.

Another aspect of the present invention provides methods for modulating an immune response, especially an undesirable or deleterious immune response, to a target antigen in a subject. These methods generally comprise administering to the subject a composition as broadly described above. The composition may be administered by injection, by topical or mucosal application, by inhalation or via the oral route including modified-release modes of administration, over a period of time and in amounts which are effective to modulate the immune response to the target antigen. In specific embodiments, the composition is administered systemically.

Typically, the immune response is associated with a condition selected from an allergy, an autoimmune disease and a transplant rejection. Thus, in yet another aspect, the invention provides methods for treating or preventing a condition whose symptoms or etiology are associated with the presence or risk of development of an undesirable or deleterious immune response to a target antigen in a subject. These methods generally comprise administering to the subject an effective amount of a composition as broadly described above. In some embodiments, the subject has a condition as broadly described above whilst in others the subject is at risk of developing such a condition. In some embodiments, when the NF-κB pathway inhibitor and the antigen are provided in different particles, they are concurrently administered to the subject.

In a related aspect, the invention extends to the use of an inhibitor of the NF-κB pathway and an antigen that corresponds to at least a portion of a target antigen, wherein the inhibitor and the antigen are in particulate form in the manufacture of a medicament for suppressing an immune response to the target antigen, or for treating or preventing an allergy or an autoimmune disease associated with the target antigen, or for treating or preventing a transplant rejection associated with the target antigen.

The invention also encompasses the use of an inhibitor of the NF-κB pathway and an antigen that corresponds to at least a portion of a target antigen, wherein the inhibitor and the antigen are in particulate form in the study and modulation of an immune response to the target antigen.

DETAILED DESCRIPTION OF THE INVENTION

1. Definitions

Figure 1:
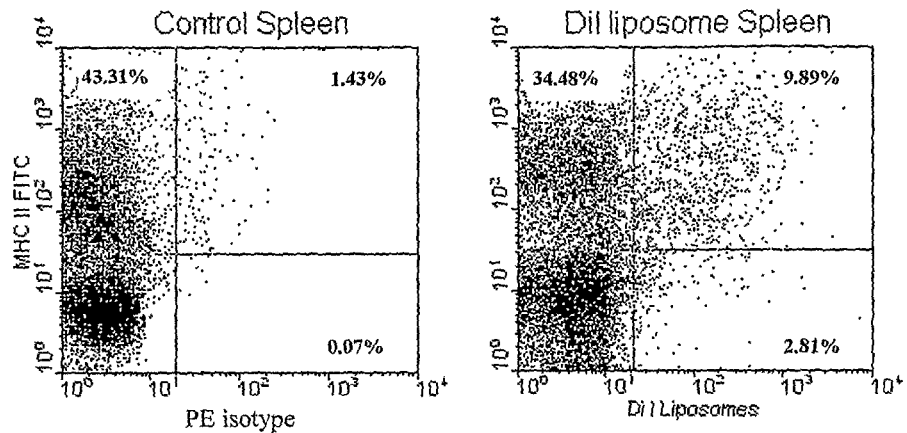
FIG. 1 is a graphical and photographic representation showing that liposomes are taken up by phagocytic cells expressing MHC class II, including dendritic cells and macrophages in lymphoid organs. A-C: 100 μL liposomes labeled with the red fluorescent dye DiI were injected into C57BL/6 mice by (A) intravenous injection via tail vein (iv), or (B) subcutaneous injection at the tail base (sc), or (C) intraperitoneally (ip). 24 hours after injection, splenocytes of mice injected intravenously and draining LNs of mice injected subcutaneously or intraperitoneally were removed and processed into cell suspensions. Cells were stained with anti-MHC class II-FITC (for i.v. and s.c. injections) or CD11c-APC (for IP injection), and analyzed by flow cytometry. Control mice received no liposomes. The proportion of class II+ or CD11c+ cells taking up liposomes is shown by the double labelled quadrant. D-H: 24 h after injection, spleens of mice injected with 100 μL of DiI curcumin liposomes either i.v. or s.c. were embedded in OCT medium and sectioned at 6 μm. Magnification: ×20. (D) iv injection. Spleen stained for monocytes and macrophages using AlexaFluor 647 CD11b (blue) and AlexaFluor 488 F480 (green) respectively. DiI+ liposomes are identified in red. (E) iv injection. Spleen sectioned and stained for myeloid dendritic cells and macrophages using AlexaFluor 647 CD11c (blue) and AlexaFluor 488 F480 (green) respectively. (F) sc injection. Spleen sectioned and stained for monocytes and macrophages using AlexaFluor 647 CD11b (blue) and AlexaFluor 488 F480 (green) respectively. (G) iv injection. Spleen sectioned and stained for myeloid dendritic cells and macrophages using AlexaFluor 647 CD11c (blue) and AlexaFluor 488 F480 (green) respectively. (H) Un-injected control spleen, stained for CD11b/F480 (left graph) and CD11c/F480 (right graph), showing absence of DiI staining (red).
Figure 1:
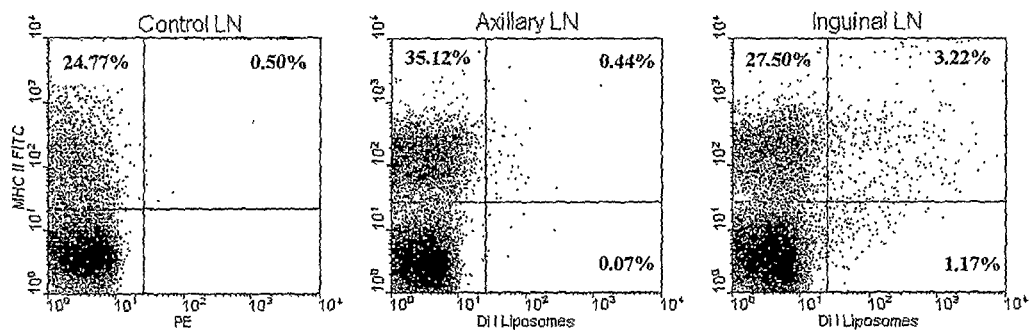
Figure 1:
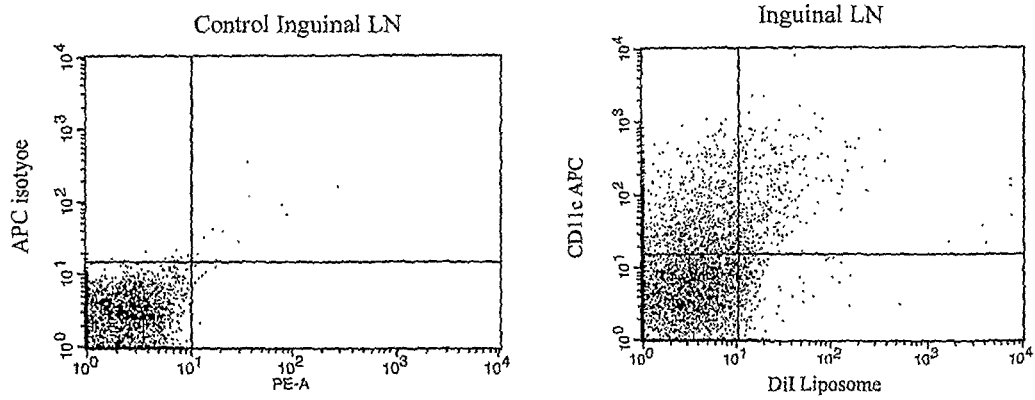
Figure 1:
Figure 1:
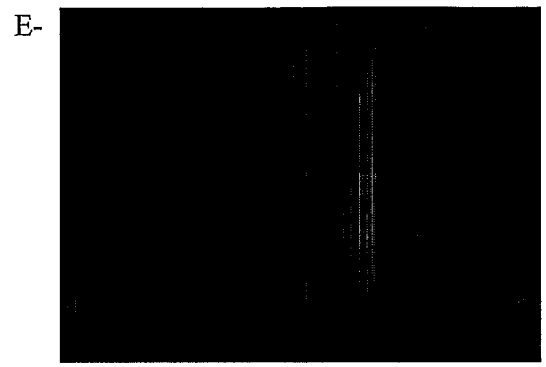
Figure 1:
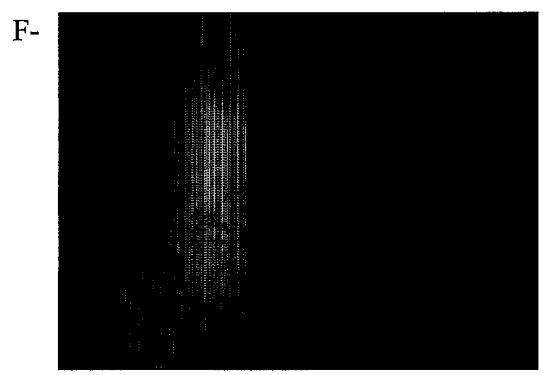
Figure 1:
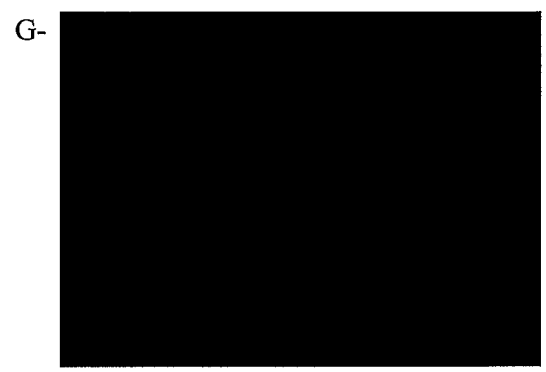
Figure 1:
Figure 1:
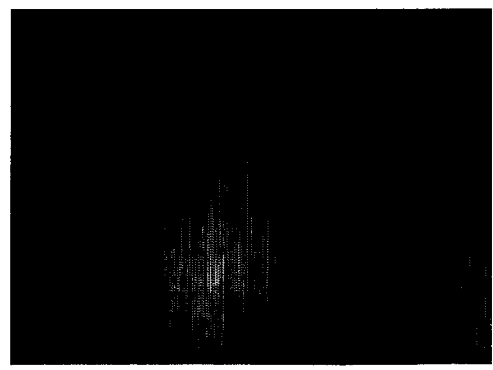

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g., amounts, concentrations, time etc) that vary by as much as 30%, preferably by as much as 20%, and more preferably by as much as 10%, 9%, 8%, 7%, 6%, 5%, 4%, 3%, 2% or 1% to a specified condition.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "anergy" as used herein refers to a suppressed response, or a state of non-responsiveness, to a specified antigen or group of antigens by an immune system. For example, T lymphocytes and B lymphocytes are anergic when they cannot respond to their specific antigen under optimal conditions of stimulation.

By "antigen" is meant all, or part of, a protein, peptide, or other molecule or macromolecule capable of eliciting an immune response in a vertebrate animal, especially a mammal. Such antigens are also reactive with antibodies from animals immunized with that protein, peptide, or other molecule or macromolecule.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "autologous" is meant something (e.g., cells, tissues etc) derived from the same organism.

The term "allogeneic" as used herein refers to cells, tissues, organisms etc that are of different genetic constitution.

By "alloantigen" is meant an antigen found only in some members of a species, such as blood group antigens. By contrast a "xenoantigen" refers to an antigen that is present in members of one species but not members of another. Correspondingly, an "allograft" is a graft between members of the same species and a "xenograft" is a graft between members of a different species.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "corresponds to" or "corresponding to" is meant an antigen which encodes an amino acid sequence that displays substantial similarity to an amino acid sequence in a target antigen. In general the antigen will display at least about 30, 40, 50, 55, 60, 65, 70, 75, 80, 85, 90, 91, 92, 93, 94, 95, 96, 97, 98, 99% similarity to at least a portion of the target antigen.

By "effective amount," in the context of modulating an immune response or treating or preventing a disease or condition, is meant the administration of that amount of composition to an individual in need thereof, either in a single dose or as part of a series, that is effective for that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

Reference herein to "immuno-interactive" includes reference to any interaction, reaction, or other form of association between molecules and in particular where one of the molecules is, or mimics, a component of the immune system.

Reference herein to "a level or functional activity" in the context of a gene expression product (e.g., a protein or a transcript) produced by a specified cell is to be taken in its broadest sense and includes a level or functional activity of the expression product that is produced in a single cell or in a plurality or population of cells. In the latter case, therefore, it will be understood that the phrase will encompass a mean level or functional activity of the protein produced by a plurality or population of cells.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (snakes, frogs, lizards etc), and fish. A preferred subject is a human in need of treatment or prophylaxis for a condition or disease, which is associated with the presence or aberrant expression of an antigen of interest. However, it will be understood that the aforementioned terms do not imply that symptoms are present.

By "pharmaceutically-acceptable carrier" is meant a solid or liquid filler, diluent or encapsulating substance that may be safely used in topical or systemic administration.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "regulatory lymphocyte" is meant a lymphocyte that is involved in regulating or suppressing responses and actions of other cells, especially of other immune cells such as B lymphocytes and T helper lymphocytes.

By "suppression," "suppressing" and the like is meant any attenuation or regulation of an immune response, including B-lymphocyte and T lymphocyte immune responses, to an antigen or group of antigens. In some embodiments, the attenuation is mediated at least in part by suppressor T lymphocytes (e.g., $CD4^+CD25^+$ regulatory T lymphocytes).

As used herein, the term "surfactant" refers to any agent, which preferentially absorbs to an interface between two immiscible phases, such as the interface between water and an organic polymer solution, a water/air interface or organic solvent/air interface. Surfactants generally possess a hydrophilic moiety and a lipophilic moiety; such that, upon absorbing to microparticles, they tend to present moieties to the external environment that do not attract similarly coated particles, thus reducing particle agglomeration. Surfactants may also promote absorption of a therapeutic or diagnostic agent and increase bioavailability of the agent.

As used herein, a particle "incorporating a surfactant" refers to a particle with a surfactant on at least the surface of the particle. The surfactant may be incorporated throughout the particle and on the surface during particle formation, or may be coated on the particle after particle formation. The surfactant can be coated on the particle surface by adsorption, ionic or covalent attachment, or physically "entrapped" by the surrounding matrix. The surfactant can be, for example, incorporated into controlled release particles, such as polymeric microspheres.

By "treatment," "treat," "treated" and the like is meant to include both therapeutic and prophylactic treatment.

2. Compositions

The present invention arises in part from the determination that co-administration of an NF-κB inhibitor and an antigen to an animal with a pre-existing immune response to the antigen, in which both the inhibitor and the antigen are in soluble form or in which one is soluble and the other is in particulate form, is ineffective in producing a tolerogenic response to the antigen. By contrast, the present inventors have discovered that strong tolerogenic responses can be generated in the animal by administering both the NF-κB inhibitor and the antigen in particulate form. Accordingly, the present invention provides compositions comprising both an inhibitor of the NF-κB pathway and an antigen that corresponds to a target antigen that is associated with an unwanted immune response for use in eliciting or stimulating tolerance to the target antigen in a range of conditions including ones that manifest in allergies, autoimmune diseases or transplant rejection.

2.1 Particles

In accordance with the present invention, the inhibitor and the antigen (also referred to herein as "the bioactive agents") are contained in or otherwise associated with the same particle or different particles. A variety of particles may be used in the invention, including but not limited to, liposomes, micelles, lipidic particles, ceramic/inorganic particles and polymeric particles, and are typically selected from nanoparticles and microparticles. The particles are suitably sized for phagocytosis or endocytosis by antigen-presenting cells. Antigen-presenting cells include both professional and facultative types of antigen-presenting cells. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Examples of facultative antigen-presenting cells include but are not limited to activated T cells, astrocytes, follicular cells, endothelium and fibroblasts. In some embodiments, the antigen-presenting cell is selected from monocytes, macrophages, B-lymphocytes, cells of myeloid lineage, dendritic cells or Langerhans cells. In specific embodiments, the antigen-presenting cell expresses CD11c and includes a dendritic cell. In illustrative examples, the particles have a dimension of less than about 100 μm, more suitably in the range of less than or equal to about 1 μm, although the particles may be as large as about 30 μm, and as small as a few nm. Liposomes consist basically of a phospholipid bilayer forming a shell around an aqueous core. Advantages include the lipophilicity of the outer layers which "mimic" the outer membrane layers of cells and that they are taken up relatively easily by a variety of cells. Polymeric vehicles typically consist of micro/nanospheres and micro/nanocapsules formed of biocompatible polymers, which are either biodegradable (for example, polylactic acid) or non-biodegradable (for example, ethylenevinyl acetate). Some of the advantages of the polymeric devices are ease of manufacture and high loading capacity, range of size from nanometer to micron diameter, as well as controlled release and degradation profile.

In some embodiments, the particles comprise an antigen-binding molecule on their surface, which is immuno-interactive with a marker that is expressed at higher levels on antigen-presenting cells (e.g., dendritic cells) than on non-antigen-presenting cells. Illustrative markers of this type include MGL, DCL-1, DEC-205, macrophage mannose R, DC-SIGN or other DC or myeloid specific (lectin) receptors, as for example disclosed by Hawiger et al. (2001, J Exp Med 194, 769), Kato et al. 2003, J Biol Chem 278, 34035), Benito et al. (2004, J Am Chem Soc 126, 10355), Schjetne, et al. (2002, Int Immunol 14, 1423) and van Vliet et al., 2006, Nat Immunol September 24; [Epub ahead of print])(van Vliet et al., Immunobiology 2006, 211:577-585).

The particles can be prepared from a combination of the bioactive agent(s), and a carrier matrix (e.g., surfactant, excipient or polymeric material). In some embodiments, the matrices are biodegradable and biocompatible, and optionally are capable of biodegrading at a controlled rate for delivery of a therapeutic or diagnostic agent. The particles can be made of a variety of materials. Both inorganic and organic materials can be used as well as polymeric and non-polymeric materials. Illustrative materials of this type include polar lipids, organic polymers and monomers, poly- and mono-saccharides, ceramic/inorganic materials, polypeptides and proteins. Other suitable materials include, but are not limited to, gelatin, polyethylene glycol, trehalose, dextran and chitosan. Particles with degradation and release times ranging from seconds to months can be designed and fabricated, based on factors such as the particle material.

2.1.1 Polymeric Particles

Polymeric particles may be formed from any biocompatible and desirably biodegradable polymer, copolymer, or blend. The polymers may be tailored to optimize different characteristics of the particle including: i) interactions between the bioactive agents to be delivered and the polymer to provide stabilization of the bioactive agents and retention of activity upon delivery; ii) rate of polymer degradation and, thereby, rate of agent release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)-hexane anhydride] (PCPH) may be used. Biodegradable polyanhydrides are described in U.S. Pat. No. 4,857,311.

In other embodiments, bulk eroding polymers such as those based on polyesters including poly(hydroxy acids) or poly(esters) can be used. For example, polyglycolic acid (PGA), polylactic acid (PLA), or copolymers thereof may be used to form the particles. The polyester may also have a charged or functionalizable group, such as an amino acid. In illustrative examples, particles with controlled release properties can be formed of poly(D,L-lactic acid) and/or poly(D, L-lactic-co-glycolic acid) ("PLGA").

Other polymers include poly(alkylcyanoacrylates), polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

In some embodiments, particles are formed from functionalized polymers such as polyester graft copolymers, as described in Hrkach et al. (1995, Macromolecules, 28:4736-4739; and "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M. Ottenbrite et al., Eds., American Chemical Society, Chapter 8, pp. 93-101, 1996.)

Materials other than biodegradable polymers may be used to form the particles. Suitable materials include various non-biodegradable polymers and various excipients. The particles also may be formed of the bioactive agent(s) and surfactant alone.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art, provided that the conditions are optimized for forming particles with the desired diameter.

Methods developed for making microspheres for delivery of encapsulated agents are described in the literature, for example, as described in Doubrow, M., Ed., "Microcapsules and Nanoparticles in Medicine and Pharmacy," CRC Press, Boca Raton, 1992. Methods also are described in Mathiowitz and Langer (1987, J. Controlled Release 5, 13-22); Mathiowitz et al. (1987, Reactive Polymers 6, 275-283); and Mathiowitz et al. (1988, J. Appl. Polymer Sci. 35, 755-774) as well as in U.S. Pat. No. 5,213,812, U.S. Pat. No. 5,417,986, U.S. Pat. No. 5,360,610, and U.S. Pat. No. 5,384,133. The selection of the method depends on the polymer selection, the size, external morphology, and crystallinity that is desired, as described, for example, by Mathiowitz et al. (1990, Scanning Microscopy 4: 329-340; 1992, J. Appl. Polymer Sci. 45, 125-134); and Benita et al. (1984, J. Pharm. Sci. 73, 1721-1724).

In solvent evaporation, described for example, in Mathiowitz et al., (1990), Benita; and U.S. Pat. No. 4,272,398 to Jaffe, the polymer is dissolved in a volatile organic solvent, such as methylene chloride. Several different polymer concentrations can be used, for example, between 0.005 and 2.0 g/mL. The bioactive agent(s), either in soluble form or dispersed as fine particles, is (are) added to the polymer solution, and the mixture is suspended in an aqueous phase that contains a surface-active agent such as poly(vinyl alcohol). The aqueous phase may be, for example, a concentration of 1% poly(vinyl alcohol) w/v in distilled water. The resulting emulsion is stirred until most of the organic solvent evaporates, leaving solid microspheres, which may be washed with water and dried overnight in a lyophilizer. Microspheres with different sizes (between 0.1 and 1000 μm) and morphologies can be obtained by this method.

Solvent removal was primarily designed for use with less stable polymers, such as the polyanhydrides. In this method, the agent is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike the hot-melt microencapsulation method described for example in Mathiowitz et al. (1987, Reactive Polymers, 6:275), this method can be used to make microspheres from polymers with high melting points and a wide range of molecular weights. Microspheres having a diameter for example between one and 300 microns can be obtained with this procedure.

With some polymeric systems, polymeric particles prepared using a single or double emulsion technique, vary in size depending on the size of the droplets. If droplets in water-in-oil emulsions are not of a suitably small size to form particles with the desired size range, smaller droplets can be prepared, for example, by sonication or homogenation of the emulsion, or by the addition of surfactants.

If the particles prepared by any of the above methods have a size range outside of the desired range, particles can be sized, for example, using a sieve, and optionally further separated according to density using techniques known to those of skill in the art.

The polymeric particles can be prepared by spray drying. Methods of spray drying, such as that disclosed in PCT WO 96/09814 by Sutton and Johnson, disclose the preparation of smooth, spherical microparticles of a water-soluble material with at least 90% of the particles possessing a mean size between 1 and 10 p.m.

2.1.2 Ceramic Particles

Ceramic particles may also be used to deliver the bioactive agents of the invention. These particles are typically prepared using processes similar to the well known sol-gel process and usually require simple and room temperature conditions as described for example in Brinker et al. ("Sol-Gel Science: The Physics and Chemistry of Sol-Gel Processing;" Academic Press: San Diego, 1990, p-60), and Avnir et al. (1994, Chem. Mater. 6, 1605). Ceramic particles can be prepared with desired size, shape and porosity, and are extremely stable. These particles also effectively protect doped molecules (polypeptides, drugs etc.) against denaturation induced by extreme pH and temperature (Jain et al., 1998, J. Am. Chem. Soc. 120, 11092-11095). In addition, their surfaces can be easily functionalized with different groups (Lal et al., 2000, Chem. Mater. 12, 2632-2639; Badley et al., 1990, Langmuir, 6, 792-801), and therefore they can be attached to a variety of monoclonal antibodies and other ligands in order to target them to desired sites in vivo.

Various ceramic particles have been described for delivery in vivo of active agent-containing payloads. For example, British Patent 1 590 574 discloses incorporation of biologically active components in a sol-gel matrix. International Publication WO 97/45367 discloses controllably dissolvable silica xerogels prepared via a sol-gel process, into which a biologically active agent is incorporated by impregnation into pre-sintered particles (1 to 500 µm) or disks. International Publication WO 0050349 discloses controllably biodegradable silica fibres prepared via a sol-gel process, into which a biologically active agent is incorporated during synthesis of the fibre. U.S. Pat. Appl. Pub. 20040180096 describes ceramic nanoparticles in which a bioactive substance is entrapped. The ceramic nanoparticles are made by formation of a micellar composition of the dye. The ceramic material is added to the micellar composition and the ceramic nanoparticles are precipitated by alkaline hydrolysis. U.S. Pat. Appl. Pub. 20050123611 discloses controlled release ceramic particles comprising an active material substantially homogeneously dispersed throughout the particles. These particles are prepared by mixing a surfactant with an apolar solvent to prepare a reverse micelle solution; (b) dissolving a gel precursor, a catalyst, a condensing agent and a soluble active material in a polar solvent to prepare a precursor solution; (c) combining the reverse micelle solution and the precursor solution to provide an emulsion and (d) condensing the precursor in the emulsion. U.S. Pat. Appl. Pub. 20060210634 discloses adsorbing bioactive substances onto ceramic particles comprising a metal oxide (e.g., titanium oxide, zirconium oxide, scandium oxide, cerium oxide and yttrium oxide) by evaporation. Kortesuo et al. (2000, Int J. Pharm. May 10; 200(2):223-229) disclose a spray drying method to produce spherical silica gel particles with a narrow particle size range for controlled delivery of drugs such as toremifene citrate and dexmedetomidine HCl. Wang et al. (2006, Int J. Pharm. 308 (1-2):160-167) describe the combination of adsorption by porous $CaCO_3$ microparticles and encapsulation by polyelectrolyte multilayer films for delivery of bioactive substances.

2.1.3 Liposomes

Liposomes can be produced by standard methods such as those reported by Kim et al. (1983, Biochim. Biophys. Acta 728, 339-348); Liu et al. (1992, Biochim. Biophys. Acta 1104, 95-101); Lee et al. (1992, Biochim. Biophys. Acta. 1103, 185-197), Brey et al. (U.S. Pat. Appl. Pub. 20020041861), Hass et al. (U.S. Pat. Appl. Pub. 20050232984), Kisak et al. (U.S. Pat. Appl. Pub. 20050260260) and Smyth-Templeton et al. (U.S. Pat. Appl. Pub. 20060204566). Additionally, reference may be made to Copeland et al. (2005, Immunol. Cell Biol. 83: 95-105) who review lipid based particulate formulations for the delivery of antigen, and to Bramwell et al. (2005, Crit. Rev Ther Drug Carrier Syst. 22(2):151-214; 2006, J Pharm Pharmacol. 58(6):717-728) who review particulate delivery systems for vaccines, including methods for the preparation of protein-loaded liposomes. Many liposome formulations using a variety of different lipid components have been used in various in vitro cell culture and animal experiments. Parameters have been identified that determine liposomal properties and are reported in the literature, for example, by Lee et al. (1992, Biochim. Biophys. Acta. 1103, 185-197); Liu et al. (1992, Biochim. Biophys. Acta, 1104, 95-101); and Wang et al. (1989, Biochem. 28, 9508-951).

In some embodiments, preparative methods based on hydration of dried-lipid film are used, in which the lipids of choice (and any organic-soluble bioactive), dissolved in an organic solvent, are mixed and dried onto the bottom of a glass container under vacuum. The lipid film is rehydrated using an aqueous buffered solution containing any water-soluble bioactives to be encapsulated by gentle swirling. The hydrated lipid vesicles can then be further processed by extrusion, submitted to a series of freeze-thawing cycles or dehydrated and then rehydrated to promote encapsulation of bioactives. Liposomes can then be washed by centrifugation or loaded onto a size-exclusion column to remove unentrapped bioactive from the liposome formulation and stored at 4° C. The basic method for liposome preparation is described in more detail in Thierry et al. (1992, Nuc. Acids Res. 20:5691-5698).

A particle carrying a payload of bioactive agent(s) can be made using the procedure as described in: Pautot et al. (2003, Proc. Natl. Acad. Sci. USA, 100(19):10718-21). Using the Pautot et al. technique, streptavidin-coated lipids (DPPC, DSPC, and similar lipids) can be used to manufacture liposomes. The drug encapsulation technique described by Needham et al. (2001, Advanced Drug Delivery Reviews, 53(3): 285-305) can be used to load these vesicles with one or more active agents.

The liposomes can be prepared by exposing chloroformic solution of various lipid mixtures to high vacuum and subsequently hydrating the resulting lipid films (DSPC/CHOL) with pH 4 buffers, and extruding them through polycarbonated filters, after a freezing and thawing procedure. It is possible to use DPPC supplemented with DSPC or cholesterol to increase encapsulation efficiency or increase stability, etc. A transmembrane pH gradient is created by adjusting the pH of the extravesicular medium to 7.5 by addition of an alkalinization agent. A bioactive agent (e.g., a small molecule inhibitor of the NF-κB pathway, which is, for example, a weak base) can be subsequently entrapped by addition of a solution of the bioactive agent in small aliquots to the vesicle solution, at an elevated temperature, to allow accumulation of the bioactive agent inside the liposomes.

Other lipid-based particles suitable for the delivery of the bioactive agents of the present invention such as niosomes are described by Copeland et al. (2005, Immunol. Cell Biol. 83: 95-105).

2.1.4 Ballistic Particles

The bioactive agents of the present invention may be attached to (e.g., by coating or conjugation) or otherwise associated with particles suitable for use in needleless or "ballistic" (biolistic) delivery. Illustrative particles for ballistic delivery are described, for example, in: International Publications WO 02/101412; WO 02/100380; WO 02/43774; WO 02/19989; WO 01/93829; WO 01/83528; WO 00/63385; WO 00/26385; WO 00/19982; WO 99/01168; WO 98/10750; and WO 97/48485. It shall be understood, however, that such particles are not limited to their use with a ballistic delivery device and can otherwise be administered by any alternative technique (e.g., injection or microneedle delivery) through which particles are deliverable to immune cells.

The active agents can be coated or chemically coupled to carrier particles (e.g., core carriers) using a variety of techniques known in the art. Carrier particles are selected from materials which have a suitable density in the range of particle sizes typically used for intracellular delivery. The optimum carrier particle size will, of course, depend on the diameter of the target cells. Illustrative particles have a size ranging from about 0.01 to about 250 µm, from about 0.05 to about 50 µm, and from about 1 to about 10 µm; and a particle density ranging from about 0.1 to about 25 g/cm$^3$. Non-limiting particles of this type include metal particles such as, tungsten, gold, platinum and iridium carrier particles. Tungsten particles are readily available in average sizes of 0.5 to 2.0 µm in diameter. Gold particles or microcrystalline gold (e.g., gold powder A1570, available from Engelhard Corp., East Newark, N.J.) may also be used. Gold particles provide uniformity in size (available from Alpha Chemicals in particle sizes of 1-3 µm, or available from Degussa, South Plainfield, N.J. in a range of particle sizes including 0.95 µm) and low toxicity. Microcrystalline gold provides a diverse particle size distribution, typically in the range of 0.1-5 µm. The irregular surface area of microcrystalline gold provides for highly efficient coating with the active agents of the present invention.

Many methods are known and have been described for adsorbing, coupling or otherwise attaching bioactive molecules (e.g., hydrophilic molecules such as proteins and nucleic acids) onto particles such as gold or tungsten particles. In illustrative examples, such methods combine a predetermined amount of gold or tungsten with the bioactive molecules, CaCl$_2$ and spermidine. In other examples, ethanol is used to precipitate the bioactive molecules onto gold or tungsten particles (see, for example, Jumar et al., 2004, Phys Med. Biol. 49:3603-3612). The resulting solution is suitably vortexed continually during the coating procedure to ensure uniformity of the reaction mixture. After attachment of the bioactive molecules, the particles can be transferred for example to suitable membranes and allowed to dry prior to use, coated onto surfaces of a sample module or cassette, or loaded into a delivery cassette for use in particular particle-mediated delivery instruments.

The formulated compositions may suitably be prepared as particles using standard techniques, such as by simple evaporation (air drying), vacuum drying, spray drying, freeze drying (lyophilization), spray-freeze drying, spray coating, precipitation, supercritical fluid particle formation, and the like. If desired, the resultant particles can be dandified using the techniques described in International Publication WO 97/48485.

2.1.5 Surfactants

Surfactants which can be incorporated into, or used to fabricate, particles include phosphoglycerides. Exemplary phosphoglycerides include phosphatidylcholines, such as the naturally occurring surfactant, L-α-phosphatidylcholine dipalmitoyl ("DPPC"). The surfactants advantageously improve surface properties by, for example, reducing particle-particle interactions, and can render the surface of the particles less adhesive. The use of surfactants endogenous to the lung may avoid the need for the use of non-physiologic surfactants.

Providing a surfactant on the surfaces of the particles can reduce the tendency of the particles to agglomerate due to interactions such as electrostatic interactions, Van der Waals forces, and capillary action. The presence of the surfactant on the particle surface can provide increased surface rugosity (roughness), thereby improving aerosolization by reducing the surface area available for intimate particle-particle interaction.

Surfactants known in the art can be used including any naturally occurring surfactant. Other exemplary surfactants include phospholipids such as diphosphatidyl glycerol (DPPG) or phosphatidylethanolamine; fatty alcohols or fatty acids such as palmitic acid or oleic acid polyoxyethylene-9-lauryl ether; sorbitan esters such as sorbitan trioleate (Span 85); bile salts; and amphiphilic polymers such as poloxamers or proteins.

2.2 Inhibitors of NF-κB Function

The inhibitor of NF-κB function includes any molecule or compound that reduces the level or functional activity of NF-κB in immune cells, especially antigen-presenting cells. In some embodiments, the inhibitor of NF-κB function decreases the level or functional activity of a member of the NF-κB pathway, which is suitably selected from BTK, LYN, BCR Igα, BCR Igβ, Syk, Blnk, PLCγ2, PKCβ, DAG, CARMA1, BCL10, MALT1, PI3K, PIP3, AKT, p38 MAPK, ERK, COT, IKKα, IKKβ, IKKγ, NIK, RelA/p65, P105/p50, c-Rel, RelB, p52, NIK, Leu13, CD81, CD19, CD21 and its ligands in the complement and coagulation cascade, TRAF6, ubiquitin ligase, Tab2, TAK1, NEMO, NOD2, RIP2, Lck, fyn, Zap70, LAT, GRB2, SOS, CD3 zeta, Slp-76, GADS, ITK, PLCγ1, PKCθ, ICOS, CD28, SHP2, SAP, SLAM and 2B4. In illustrative examples of this type, the NF-κB pathway inhibitor decreases the level or functional activity of any one or more of RelA/p65, P105/p50, c-Rel, RelB or p52. Suitably, in these embodiments, the inhibitor of NF-κB function blocks, inhibits or otherwise antagonizes at least one function or activity of the member. In other embodiments, the inhibitor of NF-κB function increases the level or functional activity of a member of the NF-κB pathway, which is suitably selected from SHP1, SHIP, PIR-B, CD22, CD72, FcgRIIB, IκB, P100, CTLA4, PD-1, Cb1, KIR3DL1, KIR3DL2, KIR2DL and Csk. In these embodiments, the inhibitor of NF-κB function increases, stimulates or otherwise agonizes at least one function or activity of the member.

Many inhibitors of NF-κB function have been described and representative examples are listed in the following tables:

TABLE 1

| ANTI-OXIDANTS THAT INHIBIT ACTIVATION OF NF-KB | |
|---|---|
| Molecule | Reference |
| a-lipoic acid | Sen et al., 1998 Jun 18; Biochem Biophys Res Commun; 247(2): 223-8; Suzuki et al., 1992 Dec 30; Biochem Biophys Res Commun.; 189(3): 1709-15 |
| a-tocopherol | Islam et al., 1998 Nov 24; Circulation; 98(21): 2255-61 |
| Aged garlic extract (allicin) | Ide & Lau, 2001 Mar; J Nutr; 131(3s): 1020S-6S. Lang et al., 2004 Oct; Clin Nutr; 23(5): 1199-208. |
| 2-Amino-1-methyl-6-phenylimidazo[4,5-b]pyridine (PhIP) | Yun et al., 2005 Jan 5; Toxicology; 217(1): 31-8. Epub 2005 Sep 15. |
| N-acetyldopamine dimers (from P. cicadae) | Xu et al., 2006 Aug 16; Bioorg Med Chem. |
| Allopurinol | Gomez-Cabrera et al., 2006 Aug; Br J Nutr; 96 Suppl 1: S31-3 |
| Anetholdithiolthione | Sen et al., 1996 Jan 5; Biochem Biophys Res Commun; 218(1): 148-53 |
| Apocynin | Barbieri et al., 2004 Jul 15; Free Radic Biol Med; 37(2): 156-65. |
| Apple juice/extracts | Shi & Jiang, 2002; J Environ Pathol Toxicol Oncol; 21(3): 233-42. Davis et al., 2006 May; Exp Biol Med (Maywood); 231(5): 594-8 |
| Aretemsia p7F (5,6,3',5'-tetramethoxy 7,4'-hydroxyflavone) | Lee et al., 2004 Dec; Ann N Y Acad Sci; 1030: 555-68 |
| Astaxanthin | Lee et al., 2003 Aug 31; Mol Cells; 16(1): 97-105. |
| Benidipine | Matsubara & Hazegawa, Eur J Pharmacol. 2004 Sep 13; 498(1-3): 303-14 |
| bis-eugenol | Murakami et al., Biochem Pharmacol. 2003 Sep 15; 66(6): 1061-6 |
| Bruguiera gymnorrhiza compounds | Homhual et al., Planta Med. 2006 Feb; 72(3): 255-60. |
| Butylated hydroxyanisole (BHA) | Israël et al., J Immunol. 1992 Nov 15; 149(10): 3386-93. Schulze-Osthoff et al., EMBO J. 1993 Aug; 12(8): 3095-104. |
| Cepharanthine | Okamoto et al., J Biol Chem. 1994 Mar 18; 269(11): 8582-9. |
| Caffeic Acid Phenethyl Ester (3,4-dihydroxycinnamic acid, CAPE) | Natarajan et al., Proc Natl Acad Sci U S A. 1996 Aug 20; 93(17): 9090-5 |
| Carnosol | Lo et al., Carcinogenesis. 2002 Jun; 23(6): 983-91 Huang et al., Biochem Pharmacol. 2005 Jan 15; 69(2): 221-32. Epub 2004 Nov 23. |
| beta-Carotene | Bai et al., Exp Mol Med. 2005 Aug 31; 37(4): 323-34 |
| Carvedilol | Yang et al., Cardiovasc Res. 2003 Sep 1; 59(3): 776-87 |
| Catechol Derivatives | Suzuki & Packer, Biochem Mol Biol Int. 1994 Feb; 32(2): 299-305 |
| Chlorogenic acid | Feng et al., J Biol Chem. 2005 Jul 29; 280(30): 27888-95. Epub 2005 Jun 8. |
| Cocoa polyphenols | Lee et al., J Nutr. 2006 May; 136(5): 1150-5. |
| Curcumin (Diferulolylmethane) | Singh & Aggarwal, J Biol Chem. 1995 Oct 20; 270(42): 24995-5000 |
| Dehydroepiandrosterone (DHEA) and DHEA-sulfate (DHEAS) | Iwasaki et al., J Clin Endocrinol Metab. 2004 Jul; 89(7): 3449-54 Liu et al., Cancer Res. 2005 Mar 15; 65(6): 2269-76 |
| Dibenzylbutyrolactone lignans | Cho et al., Int Immunopharmacol. 2002 Jan; 2(1): 105-16 |
| Diethyldithiocarbamate (DDC) | Schreck et al., J Exp Med. 1992 May 1; 175(5): 1181-94. |
| Diferoxamine | Sappey et al., AIDS Res Hum Retroviruses. 1995 Sep; 11(9): 1049-61; Schreck et al., Free Radic Res Commun. 1992; 17(4): 221-37 |

TABLE 1-continued

ANTI-OXIDANTS THAT INHIBIT ACTIVATION OF NF-KB

| Molecule | Reference |
|---|---|
| Dihydroisoeugenol | Murakami et al., Arch Biochem Biophys. 2005 Feb 15; 434(2): 326-32 |
| Dihydrolipoic Acid | Suzuki et al., Biochem Biophys Res Commun. 1992 Dec 30; 189(3): 1709-15; Suzuki et al., Biochem Mol Biol Int. 1995 Jun; 36(2): 241-6 |
| Dilazep + fenofibric acid | Sonoki et al., Eur J Pharmacol. 2003 Aug 15; 475(1-3): 139-47; Yang et al., Naunyn Schmiedebergs Arch Pharmacol. 2005 May; 371(5): 401-7. Epub 2005 May 25 |
| Dimethyldithiocarbamates (DMDTC) | Pyatt et al., Toxicology. 1998 Jul 3; 128(2): 83-90. |
| Dimethylsulfoxide (DMSO) | Kelly et al., Infect Immun. 1994 Aug; 62(8): 3122-8. |
| Disulfiram | Schreck et al., Free Radic Res Commun. 1992; 17(4): 221-37. |
| Ebselen | Schreck et al., Free Radic Res Commun. 1992; 17(4): 221-37 |
| Edaravone | Kokura et al., Cancer Lett. 2005 Nov 18; 229(2): 223-33. Epub 2005 Aug 10 |
| EPC-K1 (phosphodiester compound of vitamin E and vitamin C) | Hirano et al., Immunopharmacology. 1998 Mar; 39(1): 31-8 |
| Epigallocatechin-3-gallate (EGCG; green tea polyphenols) | Lin & Lin, Mol Pharmacol. 1997 Sep; 52(3): 465-72; Yang et al., J Nutr. 1998 Dec; 128(12): 2334-40. |
| Ergothioneine | Rahman et al., Biochem Biophys Res Commun. 2003 Mar 21; 302(4): 860-4 |
| Ethyl Pyruvate (Glutathione depletion) | Song et al., J Pharmacol Exp Ther. 2004 Jan; 308(1): 307-16. Epub 2003 Oct 20.; Tsung et al., Transplantation. 2005 Jan 27; 79(2): 196-204 |
| Ethylene Glycol Tetraacetic Acid (EGTA) | Janssen et al., Methods Enzymol. 1999; 300: 363-74 |
| Flavonoids (Crataegus; Boerhaavia diffusa root; xanthohumol) | Zhang et al., J Neurochem. 2004 Jul; 90(1): 211-9; Chen et al., Mol Pharmacol. 2004 Sep; 66(3): 683-93.; Pandey et al., Int Immunopharmacol. 2005 Mar; 5(3): 541-53; Albini et al., FASEB J. 2006 Mar; 20(3): 527-9. Epub 2005 Dec 30; Colgate et al., Cancer Lett. 2006 Mar 22; [Epub ahead of print] |
| Folic acid | Au-Yeung et al., Can J Physiol Pharmacol. 2006 Jan; 84(1): 141-7 |
| Gamma-glutamylcysteine synthetase (gamma-GCS) | Manna et al., Oncogene. 1999 Jul 29; 18(30): 4371-82 |
| Ganoderma lucidum polysaccharides | Zhang et al., Life Sci. 2003 Sep 19; 73(18): 2307-19. |
| Garcinol (from extract of Garcinia indica fruit rind) | Liao et al., Mol Carcinog. 2004 Nov; 41(3): 140-9 |
| Ginkgo biloba extract | Chen et al., Arterioscler Thromb Vasc Biol. 2003 Sep 1; 23(9): 1559-66. Epub 2003 Jul 31 |
| Glutathione | Cho et al., Biochem Biophys Res Commun. 1998 Dec 9; 253(1): 104-8; Schreck et al., Free Radic Res Commun. 1992; 17(4): 221-37 |
| Hematein | Choi et al., J Cardiovasc Pharmacol. 2003 Aug; 42(2): 287-95 |
| Hydroquinone | Pyatt et al., Toxicol Appl Pharmacol. 1998 Apr; 149(2): 178-84.; Yang et al., Zhongguo Shi Yan Xue Ye Xue Za Zhi. 2006 Aug; 14(4): 804-7 |
| 23-hydroxyursolic acid | Shin et al., Planta Med. 2004 Sep; 70(9): 803-7 |
| IRFI 042 (Vitamin E-like compound) | Altavilla et al., Free Radic Biol Med. 2001 May 15; 30(10): 1055-66 |
| Iron tetrakis | Kang et al., Toxicol Appl Pharmacol. 2003 Sep 1; 191(2): 147-55. |
| Isovitexin | Lin et al., Planta Med. 2005 Aug; 71(8): 748-53 |
| Kangen-karyu extract | Satoh et al., J Pharm Pharmacol. 2005 Oct; 57(10): 1335-43 |
| L-cysteine | Mihm et al., AIDS. 1991 May; 5(5): 497-503 |

TABLE 1-continued

ANTI-OXIDANTS THAT INHIBIT ACTIVATION OF NF-KB

| Molecule | Reference |
| --- | --- |
| Lacidipine | Cominacini et al., J Hypertens. 1997 Dec; 15(12 Pt 2): 1633-40 |
| Lazaroids | Marubayashi et al., Transplant Proc. 2002 Nov; 34(7): 2662-3 |
| Ligonberries | Wang et al., J Agric Food Chem. 2005 Apr 20; 53(8): 3156-66 |
| Lupeol | Saleem et al., Oncogene. 2004 Jul 1; 23(30): 5203-14 |
| Magnolol | Chen et al., Br J Pharmacol. 2002 Jan; 135(1): 37-47 |
| Maltol | Yang et al., J Biochem Mol Biol. 2006 Mar 31; 39(2): 145-9 |
| Manganese superoxide dismutase (Mn-SOD) | Manna et al., J Biol Chem. 1998 May 22; 273(21): 13245-54 |
| Extract of the stem bark of Mangifera indica L. | Leiro et al., Int Immunopharmacol. 2004 Aug; 4(8): 991-1003; Garrido et al., Phytother Res. 2005 Mar; 19(3): 211-5 |
| Melatonin | Gilad et al., FASEB J. 1998 Jun; 12(9): 685-93; Mohan et al., Biochem Mol Biol Int. 1995 Dec; 37(6): 1063-70; Li et al., Mediators Inflamm. 2005 Aug 31; 2005(4): 185-93 |
| Mulberry anthocyanins | Chen et al., Cancer Lett. 2006 Apr 28; 235(2): 248-59. Epub 2005 Jun 22 |
| N-acetyl-L-cysteine (NAC) | Schreck et al., EMBO J. 1991 Aug; 10(8): 2247-58 |
| Nacyselyn (NAL) | Antonicelli et al., Free Radic Biol Med. 2002 Mar 15; 32(6): 492-502 |
| Nordihydroguaiaritic acid (NDGA) | Brennan & O'Neill, Biochem Pharmacol. 1998 Apr 1; 55(7): 965-73; Israël et al., J Immunol. 1992 Nov 15; 149(10): 3386-93; Schulze-Osthoff et al., EMBO J. 1993 Aug; 12(8): 3095-104; Staal et al., AIDS Res Hum Retroviruses. 1993 Apr; 9(4): 299-306 |
| Ochnaflavone | Suh et al., Arch Biochem Biophys. 2006 Mar 15; 447(2): 136-46. Epub 2006 Feb 10 |
| Orthophenanthroline | Schreck et al., Free Radic Res Commun. 1992; 17(4): 221-37 |
| Phenolic antioxidants (Hydroquinone and tert-butyl hydroquinone) | Ma et al., 2003 |
| alpha-phenyl-n-tert-butyl-nitrone (PBN) | Kotake et al., Biochim Biophys Acta. 1998 Nov 19; 1448(1): 77-84; Lin et al., Neurosci Lett. 2006 Sep 11; 405(1-2): 52-6. Epub 2006 Jul 28 |
| Phenylarsine oxide (PAO, tyrosine phosphatase inhibitor) | Arbault et al., Biomed Pharmacother. 1997; 51(10): 430-8 |
| Phyllanthus urinaria | Chularojmontri et al., Biol Pharm Bull. 2005 Jul; 28(7): 1165-71 |
| Pyrrolinedithiocarbamate (PDTC) | Schreck et al., J Exp Med. 1992 May 1; 175(5): 1181-94 |
| Quercetin (low concentrations) | Musonda & Chipman, Carcinogenesis. 1998 Sep; 19(9): 1583-9; Shih et al., Eur J Pharmacol. 2004 Aug 2; 496(1-3): 41-8 |
| Red wine | Blanco-Colio et al., Circulation. 2000 Aug 29; 102(9): 1020-6; Cui & He, Zhonghua Yu Fang Yi Xue Za Zhi. 2004 Mar; 38(2): 103-6 |
| Ref-1 (redox factor 1) | Ozaki et al., FASEB J. 2002 Jun; 16(8): 889-90. Epub 2002 Apr 23 |
| Rg(3), a ginseng derivative | Keum et al., Mutat Res. 2003 Feb-Mar; 523-524: 75-85 |
| Rotenone | Schulze-Osthoff et al., EMBO J. 1993 Aug; 12(8): 3095-104 |
| Roxithromycin | Ueno et al., Clin Cancer Res. 2005 Aug 1; 11(15): 5645-50 |
| S-allyl-cysteine (SAC, garlic compound) | Geng et al., Free Radic Biol Med. 1997; 23(2): 345-50 |
| Sauchinone | Lee et al., Br J Pharmacol. 2003 May; 139(1): 11-20.; Hwang et al., Planta Med. 2003 Dec; 69(12): 1096-101 |

TABLE 1-continued

ANTI-OXIDANTS THAT INHIBIT ACTIVATION OF NF-KB

| Molecule | Reference |
|---|---|
| Spironolactone | Han et al., J Am Soc Nephrol. 2006 May; 17(5): 1362-72. Epub 2006 Mar 29 |
| Strawberry extracts | Wang et al., J Agric Food Chem. 2005 May 18; 53(10): 4187-93 |
| Taxifolin | Wang et al., J Biomed Sci. 2006 Jan; 13(1): 127-41. Epub 2005 Nov 9 |
| Tempol | Cuzzocrea et al., Free Radic Res. 2004 Aug; 38(8): 813-9 |
| Tepoxaline (5-(4-chlorophenyl)-N-hydroxy-(4-methoxyphenyl)-N-methyl-1H-pyrazole-3-propanamide) | Kazmi et al., J Cell Biochem. 1995 Feb; 57(2): 299-310.; Ritchie et al., Int J Immunopharmacol. 1995 Oct; 17(10): 805-12 |
| Vitamin C | Staal et al., AIDS Res Hum Retroviruses. 1993 Apr; 9(4): 299-306; Son et al., Arch Pharm Res. 2004 Oct; 27(10): 1073-9 |
| Vitamin B6 | Yanaka et al., Int J Mol Med. 2005 Dec; 16(6): 1071-5 |
| Vitamin E derivatives | Suzuki & Packer, Biochem Biophys Res Commun. 1993 May 28; 193(1): 277-83 |
| a-torphryl succinate | Staal et al., AIDS Res Hum Retroviruses. 1993 Apr; 9(4): 299-306; Suzuki & Packer, Biochem Mol Biol Int. 1993 Nov; 31(4): 693-700 |
| a-torphryl acetate | Suzuki & Packer, Biochem Biophys Res Commun. 1993 May 28; 193(1): 277-83 |
| PMC (2,2,5,7,8-pentamethyl-6-hydroxychromane) | Suzuki & Packer, Biochem Biophys Res Commun. 1993 May 28; 193(1): 277-83 |
| Yakuchinone A and B | Chun et al., J Environ Pathol Toxicol Oncol. 2002; 21(2): 131-9 |

TABLE 2A

PROTEASOME AND PROTEASES INHIBITORS OF REL/NF-KB

| Molecule | References |
|---|---|
| *Proteasome inhibitors* | |
| Peptide Aldehydes: | Palombella et al., Cell. 1994 Sep 9; 78(5): 773-85; Grisham et al., Methods Enzymol. 1999; 300: 345-63; Jobin et al., Gut. 1998 Jun; 42(6): 779-87 |
| ALLnL (N-acetyl-leucinyl-leucynil-norleucynal, MG101) | |
| LLM (N-acetyl-leucinyl-leucynil-methional) | |
| Z-LLnV (carbobenzoxyl-leucinyl-leucynil-norvalinal, MG115) | |
| Z-LLL (carbobenzoxyl-leucinyl-leucynil-leucynal, MG132) | |
| Lactacystine, b-lactone | Fenteany & Schreiber, J Biol Chem. 1998 Apr 10; 273(15): 8545-8; Grisham et al., Methods Enzymol. 1999; 300: 345-63 |
| Boronic Acid Peptide | Grisham et al., Methods Enzymol. 1999; 300: 345-63; Iqbal et al., J Med Chem. 1995 Jun 23; 38(13): 2276-7 |
| Ubiquitin Ligase Inhibitors | Yaron et al., EMBO J. 1997 Nov 3; 16(21): 6486-94 |
| PS-341 (Bortezomib) | Adams, Cancer Cell. 2004 May; 5(5): 417-21 |
| Salinosporamide A (1, NPI-0052) | Macherla et al., J Med Chem. 2005 Jun 2; 48(11): 3684-7 |
| Cyclosporin A | Frantz et al, EMBO J. 1994 Feb 15; 13(4): 861-70; Kunz et al., Biochem Biophys Res Commun. 1995 Nov 13; 216(2): 438-46; Marienfeld et al., Eur J Immunol. 1997 Jul; 27(7): 1601-9; McCaffrey et al., Nucleic Acids Res. 1994 |

TABLE 2A-continued

PROTEASOME AND PROTEASES INHIBITORS OF REL/NF-KB

| Molecule | References |
| --- | --- |
| FK506 (Tacrolimus) | Jun 11; 22(11): 2134-42; Meyer et al., FEBS Lett. 1997 Aug 18; 413(2): 354-8; Wechsler et al., J Immunol. 1994 Sep 15; 153(6): 2515-23 Okamoto et al., J Biol Chem. 1994 Mar 18; 269(11): 8582-9; Venkataraman et al., J Exp Med. 1995 Mar 1; 181(3): 1091-9 |
| Deoxyspergualin | Tepper et al., J Immunol. 1995 Sep 1; 155(5): 2427-36 |
| Disulfiram | Lovborg et al., Int J Cancer. 2006 Mar 15; 118(6): 1577-80 |
| Protease inhibitors | |
| APNE (N-acetyl-DL-phenylalanine-b-naphthylester) | Higuchi et al., Blood. 1995 Sep 15; 86(6): 2248-56 |
| BTEE (N-benzoyl L-tyrosine-ethylester) | Rossi et al., J Biol Chem. 1998 Jun 26; 273(26): 16446-52 |
| DCIC (3,4-dichloroisocoumarin) | D'Acquisto et al., FEBS Lett. 1998 Nov 27; 440(1-2): 76-80 |
| DFP (diisopropyl fluorophosphate) | |
| TPCK (N-a-tosyl-L-phenylalanine chloromethyl ketone) | |
| TLCK (N-a-tosyl-L-lysine chloromethyl ketone) | |

TABLE 2B

IκBα PHOSPHORYLATION AND/OR DEGRADATION INHIBITORS

| Molecule | Point of Inhibition | References |
| --- | --- | --- |
| BAY 11-7082 | IκBα phosphorylation | Pierce et al. J. Biol Chem 1997; 272, 21096-21103 BioMol, Plymouth Meeting, PA |
| BAY 11-7085 | IκBα phosphorylation | Pierce et al. J. Biol Chem 1997; 272, 21096-21103 BioMol, Plymouth Meeting, PA |
| Desloratadine | Histamine H1 receptor | Wu et al., Int Arch Allergy Immunol. 2004 Dec; 135(4): 313-8. Epub 2004 Nov 24 |
| Salmeterol, fluticasone propionate | beta2 agonists | Baouz et al., Int Immunol. 2005 Nov; 17(11): 1473-81. Epub 2005 Oct 6 |
| CPU0213 | Endothelin receptor antagonist | He et al., Acta Pharmacol Sin. 2006 Sep; 27(9): 1213-21 |
| Erbin overexpression | NOD2 inhibitor | McDonald et al., J Biol Chem. 2005 Dec 2; 280(48): 40301-9. Epub 2005 Oct 3 |
| Protein-bound polysaccharide from basidiomycetes | LPS-CD14 interaction | Asai et al., FEMS Immunol Med Microbiol. 2005 Jan 1; 43(1): 91-8. |
| Calagualine (fern derivative) | upstream of IKK (TRAF2-NIK) | Manna et al., Cancer Lett. 2003 Feb 20; 190(2): 171-82 |
| NS3/4A (HCV protease) | upstream of IKK | Karayiannis, J Hepatol. 2005 Oct; 43(4): 743-5 |
| golli BG21 (product of myelin basic protein) | upstream of IKK (PKC) | Feng et al., J Neuroimmunol. 2004 Jul; 152(1-2): 57-66 |
| NPM-ALK oncoprotein | Traf2 inhibition | Horie et al., Cancer Cell. 2004 Apr; 5(4): 353-64 |
| NS5A (Hepatitis C virus) | Traf2 inhibition | Park et al., J Biol Chem. 2002 Apr 12; 277(15): 13122-8. Epub 2002 Jan 30 |
| LY29 and LY30 | PI3 Kinase inhibitors | Choi et al., FEBS Lett. 2004 Feb 13; 559(1-3): 141-4 |
| Evodiamine (Evodiae Fructus component) | AKT-IKK interaction | Takada et al., J Biol Chem. 2005 Apr 29; 280(17): 17203-12. Epub 2005 Feb 14 |
| Rituximab (anti-CD20 antibody) | up-regulates Raf-1 kinase inhibitor | Jazirehi et al., Cancer Res. 2005 Jan 1; 65(1): 264-76 |
| Kinase suppressor of ras (KSR2) | MEKK3 inhibitor | Channavajhala et al., Biochem Biophys Res Commun. 2005 Sep 9; 334(4): 1214-8 |

TABLE 2B-continued

IκBα PHOSPHORYLATION AND/OR DEGRADATION INHIBITORS

| Molecule | Point of Inhibition | References |
| --- | --- | --- |
| M2L (Vaccinia virus) | ERK2 inhibitor | Gedey et al., J Virol. 2006 Sep; 80(17): 8676-85 |
| Pefabloc (serine protease inhibitor) | upstream of IKK | Tando et al., Digestion. 2002; 66(4): 237-45 |
| Rocaglamides (*Aglaia* derivatives) | upstream of IKK | Baumann et al., J Biol Chem. 2002 Nov 22; 277(47): 44791-800. Epub 2002 Sep 16 |
| Betaine | NIK/IKK | Hu et al., J Biol Chem. 2004 Aug 20; 279(34): 35975-83. Epub 2004 Jun 18 |
| TNAP | NIK | Go et al., J Gerontol A Biol Sci Med Sci. 2005 Oct; 60(10): 1252-64 |
| Geldanamycin | IKK complex formation | Chen et al., Mol Cell. 2002 Feb; 9(2): 401-10 |
| Grape seed proanthocyanidins | IKKa activity | Mantena & Katiyar, Free Radic Biol Med. 2006 May 1; 40(9): 1603-14. Epub 2006 Jan 26 |
| MC160 (Molluscum contagiosum virus) | IKKa activity | Nichols & Shisler, J Virol. 2006 Jan; 80(2): 578-86 |
| NS5B (Hepatitis C protein) | IKKa activity | Choi et al., Mol Cell Biol. 2006 Apr; 26(8): 3048-59 |
| Pomegranate fruit extract | IKKa activity | Afaq et al., Photochem Photobiol. 2005 Jan-Feb; 81(1): 38-45; Khan et al., Carcinogenesis. 2006 Aug 18; [Epub ahead of print] |
| Tetrandine (plant alkaloid) | IKKa activity | Ho et al., Br J Pharmacol. 2004 Dec; 143(7): 919-27. Epub 2004 Oct 25 |
| BMS-345541 (4(2'-Aminoethyl)amino-1,8-dimethylimidazo(1,2-a)quinoxaline) | IKKa and IKKb kinase activity | Burke et al., J Biol Chem. 2003 Jan 17; 278(3): 1450-6. Epub 2002 Oct 25; Yang et al., 2006 |
| 2-amino-3-cyano-4-aryl-6-(2-hydroxy-phenyl)pyridine derivatives | IKKb activity | Murata et al., Bioorg Med Chem Lett. 2003 Mar 10; 13(5): 913-8, Murata et al., Bioorg Med Chem Lett. 2004 Aug 2; 14(15): 4013-7, Murata et al., Bioorg Med Chem Lett. 2004 Aug 2; 14(15): 4019-22 |
| Acrolein | IKKb activity | Vallacchi et al., Antioxid Redox Signal. 2005 Jan-Feb; 7(1-2): 25-31 |
| Anandamide | IKKb activity | Sancho et al., Mol Pharmacol. 2003 Feb; 63(2): 429-38 |
| AS602868 | IKKb activity | Frelin et al., Oncogene. 2003 Nov 6; 22(50): 8187-94 |
| Cobrotoxin | IKKb activity and p50 DNA binding | Park et al., Biochemistry. 2005 Jun 14; 44(23): 8326-36 |
| Core protein (Hepatitis C) | IKKb activity | Joo et al., J Virol. 2005 Jun; 79(12): 7648-57; Shrivastava et al., J Virol. 1998 Dec; 72(12): 9722-8 |
| Dihydroxyphenylethanol | IKKb activity | Guichard et al., Carcinogenesis. 2006 Sep; 27(9): 1812-27. Epub 2006 Mar 7 |
| Herbimycin A | IKKb activity | Iwasaki et al., FEBS Lett. 1992 Feb 24; 298(2-3): 240-4; Mahon & O'Neill, Biochem Soc Trans. 1995 Feb; 23(1): 111S; Ogino et al., Mol Pharmacol. 2004 Jun; 65(6): 1344-51 |
| Inhibitor 22 | IKKb activity | Baxter et al., Bioorg Med Chem Lett. 2004 Jun 7; 14(11): 2817-22 |
| Isorhapontigenin | IKKb activity | Li et al., Free Radic Biol Med. 2005 Jan 15; 38(2): 243-57 |
| Manumycin A | IKKb activity | Bernier et al., J Biol Chem. 2006 Feb 3; 281(5): 2551-61. Epub 2005 Nov 30; Frassanito et al., Clin Exp Med. 2005 Mar; 4(4): 174-82 |
| MLB120 (small molecule) | IKKb activity | Nagashima et al., Blood. 2006 Jun 1; 107(11): 4266-73. Epub 2006 Jan 26 |
| Novel Inhibitor | IKKb activity | Kamon et al., Biochem Biophys Res Commun. 2004 Oct 8; 323(1): 242-8 |

TABLE 2B-continued

IκBα PHOSPHORYLATION AND/OR DEGRADATION INHIBITORS

| Molecule | Point of Inhibition | References |
| --- | --- | --- |
| vIRF3 (KSHV) | IKKb activity | Seo et al., Oncogene. 2004 Aug 12; 23(36): 6146-55 |
| Nitric oxide | IKKb activity/IkB phosphorylation | Katsuyama et al., Arterioscler Thromb Vasc Biol. 1998 Nov; 18(11): 1796-802; Matthews et al., Nucleic Acids Res. 1996 Jun 15; 24(12): 2236-42; Spieker & Liao, Methods Enzymol. 1999; 300: 374-88; Reynaert et al., Proc Natl Acad Sci USA. 2004 Jun 15; 101(24): 8945-50. Epub 2004 Jun 7 |
| SC-514 (small molecule) | IKKb activity | Kishore et al., J Biol Chem. 2003 Aug 29; 278(35): 32861-71. Epub 2003 Jun 17 |
| Thienopyridine | IKKb activity | Morwick et al., J Med Chem. 2006 May 18; 49(10): 2898-908 |
| Acetyl-boswellic acids | IKK activity | Syrovets et al., J Biol Chem. 2005 Feb 18; 280(7): 6170-80. Epub 2004 Dec 2; Syrovets et al., J Immunol. 2005 Jan 1; 174(1): 498-506 |
| Amino-pyrimidine derivative | IKK activity | Karin et al., Nat Rev Drug Discov. 2004 Jan; 3(1): 17-26 |
| Benzoimidazole derivative | IKK activity | Karin et al., Nat Rev Drug Discov. 2004 Jan; 3(1): 17-26 |
| BMS-345541 | IKK activity | Burke et al., J Biol Chem. 2003 Jan 17; 278(3): 1450-6. Epub 2002 Oct 25. |
| Beta-carboline | IKK activity | Yoon et al., J Toxicol Environ Health A. 2005 Dec 10; 68(23-24): 2005-17 |
| CYL-19s and CYL-26z, two synthetic alpha-methylene-gamma-butyrolactone derivatives | IKK activity | Huang et al., Carcinogenesis. 2004 Oct; 25(10): 1925-34. Epub 2004 Jun 24 |
| ACHP (2-amino-6-[2-(cyclopropylmethoxy)-6-hydroxyphenyl]-4-piperidin-4-yl nicotinonitrile | IKKb activity (ATP analog) | Sanda et al., Leukemia. 2006 Apr; 20(4): 590-8 |
| Compound A | IKKb activity (ATP analog) | Ziegelbauer et al., Br J Pharmacol. 2005 May; 145(2): 178-92 |
| Flavopiridol | IKK activity and RelA phosphor. | Takada & Aggarwal, J Biol Chem. 2004 Feb 6; 279(6): 4750-9. Epub 2003 Nov 20 |
| Cyclopentones | IKKb activity | Bickley et al., Bioorg Med Chem. 2004 Jun 15; 12(12): 3221-7 |
| Dehydroascorbic acid (Vitamin C) | IKKb activity | Carcamo et al., Mol Cell Biol. 2004 Aug; 24(15): 6645-52 |
| IMD-0354 | IKKb activity | Tanaka et al., Blood. 2005 Mar 15; 105(6): 2324-31. Epub 2004 Nov 23, Tanaka et al., Cancer Res. 2006 Jan 1; 66(1): 419-26; Inayama et al., Am J Respir Crit Care Med. 2006 May 1; 173(9): 1016-22. Epub 2006 Feb 2 |
| Jesterone dimer | IKKb activity; DNA binding | Liang et al., Mol Pharmacol. 2003 Jul; 64(1): 123-31; Liang et al., 2006 |
| PS-1145 (MLN1145) | IKKb activity | Hideshima et al., J Biol Chem. 2002 May 10; 277(19): 16639-47. Epub 2002 Feb 28 |
| 2-[(aminocarbonyl)amino]-5-acetylenyl-3-thiophenecarboxamides (TPCA-1) | IKKb activity | Bonafoux et al., Bioorg Med Chem Lett. 2005 Jun 2; 15(11): 2870-5; Podolin et al., 2005 |
| 1'-Acetoxychavicol acetate (*Languas galanga*) | IKK activity | Ichikawa et al., J Immunol. 2005 Jun 1; 174(11): 7383-92; Ito et al., Cancer Res. 2005 May 15; 65(10): 4417-24 |
| Apigenin (plant flavinoid) | IKK activity | Shukla & Gupta, Clin Cancer Res. 2004 May 1; 10(9): 3169-78; |

TABLE 2B-continued

IκBα PHOSPHORYLATION AND/OR DEGRADATION INHIBITORS

| Molecule | Point of Inhibition | References |
| --- | --- | --- |
| | | Yoon et al., Mol Pharmacol. 2006 Sep; 70(3): 1033-44. Epub 2006 Jun 16 |
| Cardamomin | IKK activity | Lee et al., J Pharmacol Exp Ther. 2006 Jan; 316(1): 271-8. Epub 2005 Sep 23 |
| CDDO-Me (synthetic triterpenoid) | IKK activity | Shishodia et al., Clin Cancer Res. 2006 Mar 15; 12(6): 1828-38 |
| CHS 828 (anticancer drug) | IKK activity | Olsen et al., Int J Cancer. 2004 Aug 20; 111(2): 198-205 |
| CML-1 | IKK activity | Mo et al., J Ethnopharmacol. 2006 Jul 11; [Epub ahead of print] |
| Compound 5 (Uredio-thiophenecarboxamide derivative) | IKK activity | Roshak et al., Curr Opin Pharmacol. 2002 Jun; 2(3): 316-21 |
| Diaylpyridine derivative | IKK activity | Murata et al., Bioorg Med Chem Lett. 2003 Mar 10; 13(5): 913-8 |
| Diosgenin | IKK activity | Shishodia & Aggarwal, Oncogene. 2006 Mar 9; 25(10): 1463-73; Liagre et al., Int J Mol Med. 2005 Dec; 16(6): 1095-101 |
| E3-14.7K (Adenovirus) | IKK activity | Li et al., Proc Natl Acad Sci USA. 1999 Feb 2; 96(3): 1042-7 |
| E3-10.4K/14.5K (Adenovirus) | IKK activity | Friedman & Horwitz, J Virol. 2002 Jun; 76(11): 5515-21 |
| E7 (human papillomavirus) | IKK activity | Spitkovsky et al., J Biol Chem. 2002 Jul 12; 277(28): 25576-82. Epub 2002 May 1 |
| Furonaphthoquinone | IKK activity | Shin et al., Int Immunopharmacol. 2006 Jun; 6(6): 916-23. Epub 2006 Feb 3 |
| Guggulsterone | IKK activity | Ichikawa & Aggarwal, Clin Cancer Res. 2006 Jan 15; 12(2): 662-8 |
| HB-EGF (Heparin-binding epidermal growth factor-like growth factor) | IKK activity | Mehta & Besner, J Immunol. 2003 Dec 1; 171(11): 6014-22 |
| Falcarindol | IKK activity | Shiao et al., Br J Pharmacol. 2005 Jan; 144(1): 42-51 |
| Hepatocyte growth factor | IKK activity | Min et al., Circ Res. 2005 Feb 18; 96(3): 300-7. Epub 2005 Jan 6; Gong et al., J Am Soc Nephrol. 2006 Sep; 17(9): 2464-73. Epub 2006 Aug 2 |
| Honokiol | IKK activity | Tse et al., Biochem Pharmacol. 2005 Nov 15; 70(10): 1443-57. Epub 2005 Sep 21 |
| Hypoestoxide | IKK activity | Ojo-Amaize et al., Cell Immunol. 2001 May 1; 209(2): 149-57 |
| Indolecarboxamide derivative | IKK activity | Karin et al., Nat Rev Drug Discov. 2004 Jan; 3(1): 17-26 |
| LF15-0195 (analog of 15-deoxyspergualine) | IKK activity | Yang et al., J Leukoc Biol. 2003 Sep; 74(3): 438-47 |
| gamma-mangostin (from *Garcinia mangostana*) | IKK activity | Nakatani et al., Mol Pharmacol. 2004 Sep; 66(3): 667-74 |
| Garcinone B | IKK activity | Yamakuni et al., Neurosci Lett. 2006 Feb 20; 394(3): 206-10. Epub 2005 Nov 2 |
| (Amino)imidazolylcarboxaldehyde derivative | IKK activity | Karin et al., Nat Rev Drug Discov. 2004 Jan; 3(1): 17-26. |
| Imidazolylquinoline-carboxaldehyde derivative | IKK activity | Karin et al., Nat Rev Drug Discov. 2004 Jan; 3(1): 17-26 |
| Kahweol | IKK activity | Kim et al., Cancer Lett. 2004 Sep 30; 213(2): 147-54 |
| Kava (*Piper methysticum*) derivatives | IKK activity | Folmer et al., Biochem Pharmacol. 2006 Apr 14; 71(8): 1206-18. Epub 2006 Feb 7 |
| Lead | IKK activity | Xu et al., Cell Biol Toxicol. 2006 May; 22(3): 189-98 |
| Mild hypothermia | IKK activity | Han et al., J Cereb Blood Flow Metab. 2003 May; 23(5): 589-98 |
| ML120B | IKK activity | Catley et al., Mol Pharmacol. 2006 Aug; 70(2): 697-705. Epub 2006 May 10 |

TABLE 2B-continued

IκBα PHOSPHORYLATION AND/OR DEGRADATION INHIBITORS

| Molecule | Point of Inhibition | References |
| --- | --- | --- |
| MX781 (retinoid antagonist) | IKK activity | Bayon et al., Mol Cell Biol. 2003 Feb; 23(3): 1061-74 |
| N-acetylcysteine | IKK activity | Oka et al., FEBS Lett. 2000 Apr 28; 472(2-3): 196-202 |
| Nitrosylcobalamin (vitamin B12 analog) | IKK activity | Chawla-Sarkar et al., J Biol Chem. 2003 Oct 10; 278(41): 39461-9. Epub 2003 Jul 24 |
| NSAIDs | IKK activity | Takada et al., Oncogene. 2004 Dec 9; 23(57): 9247-58 |
| Hepatits C virus NS5B | IKK activity | Choi et al., Mol Cell Biol. 2006 Apr; 26(8): 3048-59 |
| PAN1 (aka NALP2 or PYPAF2) | IKK activity | Bruey et al., J Biol Chem. 2004 Dec 10; 279(50): 51897-907. Epub 2004 Sep 28 |
| Pectin (citrus) | IKK activity | Chen et al., Biochem Pharmacol. 2006 Oct 16; 72(8): 1001-9. Epub 2006 Aug 22 |
| Pyrazolo[4,3-c]quinoline derivative | IKK activity | Karin et al., Nat Rev Drug Discov. 2004 Jan; 3(1): 17-26 |
| Pyridooxazinone derivative | IKK activity | Karin et al., Nat Rev Drug Discov. 2004 Jan; 3(1): 17-26 |
| N-(4-hydroxyphenyl) retinamide | IKK activity | Shishodia et al., Cancer Res. 2005 Oct 15; 65(20): 9555-65 |
| Scytonemin | IKK activity | Stevenson et al., Inflamm Res. 2002 Feb; 51(2): 112-4 |
| *Semecarpus anacardiu* extract | IKK activity | Singh et al., J Ethnopharmacol. 2006 Jun 2; [Epub ahead of print] |
| SPC-839 | IKK activity | Palanki et al., 2002 |
| Sulforaphane and phenylisothiocyanate | IKK activity | Xu et al., Oncogene. 2005 Jun 30; 24(28): 4486-95 |
| Survanta (Surfactant product) | IKK activity | Raychaudhuri et al., Am J Respir Cell Mol Biol. 2004 Feb; 30(2): 228-32. Epub 2003 Aug 14 |
| Piceatannol | IKK activity | Islam et al., Microbiol Immunol. 2004; 48(10): 729-36 |
| Plumbagin (5-hydroxy-2-methyl-1,4-naphthoquinone) | IKK activity | Sandur et al., J Biol Chem. 2006 Jun 23; 281(25): 17023-33. Epub 2006 Apr 19 |
| IKKb peptide to NEMO binding domain | IKK-NEMO interaction | May et al., Science. 2000 Sep 1; 289(5484): 1550-4 |
| NEMO CC2-LZ peptide | NEMO oligomerization | Agou et al., 2004 |
| AGRO100 (G-quadraplex oligodeoxynucleotide) | NEMO binding | Girvan et al., Mol Cancer Ther. 2006 Jul; 5(7): 1790-9 |
| PTEN (tumor suppressor) | Activation of IKK | Gustin et al., J Biol Chem. 2001 Jul 20; 276(29): 27740-4. Epub 2001 May 16 |
| Theaflavin (black tea component) | Activation of IKK | Aneja et al., Crit Care Med. 2004 Oct; 32(10): 2097-103; Ukil et al., Br J Pharmacol. 2006 Sep; 149(1): 121-31. Epub 2006 Jul 31 |
| Tilianin | Activation of IKK | Nam et al., Atherosclerosis. 2005 May; 180(1): 27-35. Epub 2005 Jan 19 |
| Withanolides | Activation of IKK | Ichikawa et al., Mol Cancer Ther. 2006 Jun; 5(6): 1434-45 |
| Zerumbone | Activation of IKK | Takada et al., Oncogene. 2005 Oct 20; 24(46): 6957-69 |
| Silibinin | IKKα activity; nuclear translocation | Dhanalakshmi et al., Oncogene. 2002 Mar 7; 21(11): 1759-67; Singh et al., Oncogene. 2005 Feb 10; 24(7): 1188-202 |
| Sulfasalazine | IKKa and IKKb kinase activity | Wahl et al., J Clin Invest. 1998 Mar 1; 101(5): 1163-74: Weber et al., Gastroenterology. 2000 Nov; 119(5): 1209-18 |
| Sulfasalazine analogs | IKK kinase activity | Habens et al., Apoptosis. 2005 May; 10(3): 481-91 |
| Quercetin | IKK activity | Peet & Li, J Biol Chem. 1999 Nov 12; 274(46): 32655-61 |
| Rosmarinic acid | IKK activity | Lee et al., Br J Pharmacol. 2006 Jun; 148(3): 366-75 |
| Staurosporine | IKK activity | Peet & Li, J Biol Chem. 1999 Nov 12; 274(46): 32655-61 |

TABLE 2B-continued

IκBα PHOSPHORYLATION AND/OR DEGRADATION INHIBITORS

| Molecule | Point of Inhibition | References |
| --- | --- | --- |
| gamma-Tocotrienol | IKK activity | Shah & Sylvester, Exp Biol Med (Maywood). 2005 Apr; 230(4): 235-41 |
| Wedelolactone | IKK activity | Kobori et al., Cell Death Differ. 2004 Jan; 11(1): 123-30 |
| Betulinic acid | IKKa activity and p65 phosphorylation | Takada & Aggarwal, J Immunol. 2003 Sep 15; 171 (6): 3278-86 |
| Ursolic acid | IKKa activity and p65 phosphorylation | Shishodia et al., Cancer Res. 2003 Aug 1; 63(15): 4375-83 |
| Thalidomide (and thalidomide analogs) | IKK activity | Keifer et al., J Biol Chem. 2001 Jun 22; 276(25): 22382-7. Epub 2001 Apr 10; Ge et al., Blood. 2006 Aug 29; [Epub ahead of print] |
| Interleukin-10 | Reduced IKKa and IKKb expression | Tabary et al., Am J Pathol. 2003 Jan; 162(1): 293-302 |
| MC160 (molluscum contagiosum virus) | Reduced IKKa expression | Nichols & Shisler, J Virol. 2006 Jan; 80(2): 578-86 |
| Monochloramine and glycine chloramine (NH2Cl) | Oxidizes IkB | Kim et al., Biochim Biophys Acta. 2005 Dec 15; 1746(2): 135-42. Epub 2005 Oct 28; Midwinter et al., Biochem J. 2006 May 15; 396(1): 71-8 |
| Anethole | Phosphorylation | Chainy et al., Oncogene. 2000 Jun 8; 19(25): 2943-50 |
| Anti-thrombin III | Phosphorylation | Oelschlager et al., Blood. 2002 Jun 1; 99(11): 4015-20 |
| Artemisia vestita | Phosphorylation | Sun et al., Int J Mol Med. 2006 May; 17(5): 957-62 |
| Aspirin, sodium salicylate | Phosphorylation, IKKbeta | Frantz & O'Neill, Science. 1995 Dec 22; 270(5244): 2017-9; Kopp & Ghosh, Science. 1994 Aug 12; 265(5174): 956-9; Yin et al., Nature. 1998 Nov 5; 396(6706): 77-80 |
| Azidothymidine (AZT) | Phosphorylation | Ghosh et al., Blood. 2003 Mar 15; 101(6): 2321-7. Epub 2002 Oct 24.; Kurokawa et al., Blood. 2005 Jul 1; 106(1): 235-40. Epub 2005 Mar 24 |
| Baoganning | Phosphorylation | Tan et al., Zhongguo Zhong Xi Yi Jie He Za Zhi. 2005 Sep; 25(9): 804-7 |
| BAY-11-7082 (E3((4-methylphenyl)-sulfonyl)-2-propenenitrile) | Phosphorylation | Pierce et al., J Biol Chem. 1997 Aug 22; 272(34): 21096-103. |
| BAY-117083 (E3((4-t-butylphenyl)-sulfonyl)-2-propenenitrile) | Phosphorylation | Pierce et al., J Biol Chem. 1997 Aug 22; 272(34): 21096-103 |
| Benzyl isothiocyanate | Phosphorylation | Srivastava & Singh, Carcinogenesis. 2004 Sep; 25(9): 1701-9. Epub 2004 Apr 29 |
| Black raspberry extracts (cyanidin 3-O-glucoside, cyanidin 3-O-(2(G)-xylosylrutinoside), cyanidin 3-O-rutinoside) | Phosphorylation | Huang et al., Cancer Res. 2002 Dec 1; 62(23): 6857-63.; Hecht et al., Carcinogenesis. 2006 Aug; 27(8): 1617-26. Epub 2006 Mar 7 |
| Buddlejasaponin IV | Phosphorylation | Won et al., Br J Pharmacol. 2006 May; 148(2): 216-25 |
| Cacospongionolide B | Phosphorylation | Posadas et al., Br J Pharmacol. 2003 Apr; 138(8): 1571-9 |
| Calagualine | Phosphorylation | Manna et al., Cancer Lett. 2003 Feb 20; 190(2): 171-82 |
| Carbon monoxide | Phosphorylation | Sarady et al., Am J Respir Cell Mol Biol. 2002 Dec; 27(6): 739-45 |
| Carboplatin | Phosphorylation | Singh & Bhat, Biochem Biophys Res Commun. 2004 May 28; 318(2): 346-53 |
| Cardamonin | Phosphorylation | Israf et al., Mol Immunol. 2007 Feb; 44(5): 673-9. Epub 2006 Jun 13 |
| Chorionic gonadotropin | Phosphorylation | Manna et al., J Biol Chem. 2000 May 5; 275(18): 13307-14 |

TABLE 2B-continued

IκBα PHOSPHORYLATION AND/OR DEGRADATION INHIBITORS

| Molecule | Point of Inhibition | References |
| --- | --- | --- |
| Cordycepin | Phosphorylation | Kim et al., Eur J Pharmacol. 2006 Sep 18; 545(2-3): 192-9. Epub 2006 Jun 28 |
| Cycloepoxydon; 1-hydroxy-2-hydroxymethyl-3-pent-1-enylbenzene | Phosphorylation | Gehrt et al., J Antibiot (Tokyo). 1998 May; 51(5): 455-63 |
| Cytomegalovirus | Phosphorylation | Jarvis et al., 2006 |
| Decursin | Phosphorylation | Kim et al., Mol Pharmacol. 2006 Jun; 69(6): 1783-90. Epub 2006 Mar 1 |
| Dexanabinol | Phosphorylation | Juttler et al., Neuropharmacology. 2004 Sep; 47(4): 580-92 |
| Digitoxin | Phosphorylation | Srivastava et al., Proc Natl Acad Sci USA. 2004 May 18; 101(20): 7693-8. Epub 2004 May 10 |
| Diterpenes (synthetic) | Phosphorylation | Chao et al., Chembiochem. 2005 Jan; 6(1): 133-44 |
| Docosahexaenoic acid | Phosphorylation | Chen et al., Invest Ophthalmol Vis Sci. 2005 Nov; 46(11): 4342-7 |
| *Entamoeba histolytica* | Phosphorylation | Kammanadiminti & Chadee, J Biol Chem. 2006 Sep 8; 281(36): 26112-20. Epub 2006 Jul 13 |
| Extensively oxidized low density lipoprotein (ox-LDL), 4-Hydroxynonenal (HNE) | Phosphorylation | Brand et al., Arterioscler Thromb Vasc Biol. 1997 Oct; 17(10): 1901-9; Page et al., J Biol Chem. 1999 Apr 23; 274(17): 11611-8 |
| FHIT (Fragile histidine triad protein) | Phosphorylation | Nakagawa & Akao, Exp Cell Res. 2006 Aug 1; 312(13): 2433-42. Epub 2006 Apr 25 |
| Gabexate mesilate | Phosphorylation | Uchiba et al., Crit Care Med. 2003 Apr; 31(4): 1147-53 |
| [6]-gingerol; casparol | Phosphorylation | Kim et al., Oncogene. 2005 Apr 7; 24(15): 2558-67.; Aktan et al., Planta Med. 2006 Jun; 72(8): 727-34. Epub 2006 May 29 |
| Gleevec (Imatanib) | Phosphorylation | Wolf et al., Proc Natl Acad Sci USA. 2005 Sep 20; 102(38): 13622-7. Epub 2005 Sep 8 |
| *Glossogyne tenuifolia* | Phosphorylation | Wu et al., J Biomed Sci. 2004 Mar-Apr; 11(2): 186-99; Ha et al., J Ethnopharmacol. 2006 Aug 11; 107(1): 116-25. Epub 2006 Apr 3 |
| Guggulsterone | Phosphorylation | Shishodia & Aggarwal, J Biol Chem. 2004 Nov 5; 279(45): 47148-58. Epub 2004 Aug 17 |
| Hydroquinone | Phosphorylation | Kerzic et al., Toxicology. 2003 May 3; 187(2-3): 127-37 |
| Ibuprofen | Phosphorylation | Palayoor et al., Oncogene. 1999 Dec 2; 18(51): 7389-94 |
| Indirubin-3'-oxime | Phosphorylation | Mak et al., Biochem Pharmacol. 2004 Jan 1; 67(1): 167-74 |
| Interferon-alpha | Phosphorylation | Manna et al., J Immunol. 2000 Nov 1; 165(9): 4927-34 |
| Inhaled isobutyl nitrite | Phosphorylation | Ponnappan et al., Int Immunopharmacol. 2004 Aug; 4(8): 1075-82 |
| Licorce extracts | Phosphorylation | Kim et al., Biochem Biophys Res Commun. 2006 Jul 7; 345(3): 1215-23. Epub 2006 May 15 |
| Melatonin | Phosphorylation | Alonso et al., J Pineal Res. 2006 Aug; 41(1): 8-14 |
| Methotrexate | Phosphorylation | Majumdar & Aggarwal, J Immunol. 2001 Sep 1; 167(5): 2911-20; Yozai et al., J Am Soc Nephrol. 2005 Nov; 16(11): 3326-38. Epub 2005 Sep 21 |
| Monochloramine | Phosphorylation | Omori et al., Free Radic Res. 2002 Aug; 36(8): 845-52 |

TABLE 2B-continued

IκBα PHOSPHORYLATION AND/OR DEGRADATION INHIBITORS

| Molecule | Point of Inhibition | References |
| --- | --- | --- |
| Nafamostat mesilate | Phosphorylation | Noguchi et al., Int Immunopharmacol. 2003 Sep; 3(9): 1335-44 |
| Oleandrin | Phosphorylation | Manna et al., Cancer Res. 2000 Jul 15; 60(14): 3838-47; Sreeivasan et al., Biochem Pharmacol. 2003 Dec 1; 66(11): 2223-39 |
| Omega 3 fatty acids | Phosphorylation | Novak et al., Am J Physiol Lung Cell Mol Physiol. 2003 Jan; 284(1): L84-9. Epub 2002 Aug 30 |
| Panduratin A (from *Kaempferia pandurata*, Zingiberaceae) | Phosphorylation | Yun et al., Planta Med. 2003 Dec; 69(12): 1102-8 |
| Petrosaspongiolide M | Phosphorylation | Posadas et al., Biochem Pharmacol. 2003 Mar 1; 65(5): 887-95 |
| Pinosylvin | Phosphorylation | Lee et al., Planta Med. 2006 Jul; 72(9): 801-6. Epub 2006 Jun 19 |
| *Plagius flosculosus* extract polyacetylene spiroketal | Phosphorylation | Calzado et al., Biochim Biophys Acta. 2005 Jun 30; 1729(2): 88-93 |
| Phytic acid (inositol hexakisphosphate) | Phosphorylation | Ferry et al., Carcinogenesis. 2002 Dec; 23(12): 2031-41 |
| Pomegranate fruit extract | Phosphorylation | Ahmed et al., J Nutr. 2005 Sep; 135(9): 2096-102 |
| Prostaglandin A1 | Phosphorylation/IKK | Rossi et al., Proc Natl Acad Sci USA. 1997 Jan 21; 94(2): 746-50; Rossi et al., Nature. 2000 Jan 6; 403(6765): 103-8 |
| 20(S)-Protopanaxatriol (ginsenoside metabolite) | Phosphorylation | Oh et al., Cancer Lett. 2004 Mar 8; 205(1): 23-9; Lee et al., Planta Med. 2005 Dec; 71(12): 1167-70 |
| Rengyolone | Phosphorylation | Kim et al., Biochem Pharmacol. 2006 Apr 14; 71(8): 1198-205. Epub 2006 Feb 2 |
| Rottlerin | Phosphorylation | Kim et al., Biochem Biophys Res Commun. 2005 Nov 11; 337(1): 110-5 |
| Saikosaponin-d | Phosphorylation | Leung et al., Biochem Biophys Res Commun. 2005 Dec 30; 338(4): 1920-7. Epub 2005 Nov 11. |
| Saline (low Na+ istonic) | Phosphorylation | Tabary et al., Biochem Biophys Res Commun. 2003 Sep 19; 309(2): 310-6 |
| *Salvia miltiorrhizae* water-soluble extract | Phosphorylation | Kim et al., Clin Exp Immunol. 2005 Aug; 141(2): 288-97. |
| Sanguinarine (pseudochelerythrine, 13-methyl-[1,3]-benzodioxolo-[5,6-c]-1,3-dioxolo-4,5 phenanthridinium) | Phosphorylation | Chaturvedi et al., J Biol Chem. 1997 Nov 28; 272(48): 30129-34 |
| Scoparone | Phosphorylation | Jang et al., Life Sci. 2006 May 15; 78(25): 2937-43. Epub 2005 Dec 22 |
| Sesaminol glucosides | Phosphorylation | Lee et al., Neurosci Res. 2006 Oct; 56(2): 204-12. Epub 2006 Jul 13 |
| Silymarin | Phosphorylation | Manna et al., J Immunol. 1999 Dec 15; 163(12): 6800-9; Saliou et al., FEBS Lett. 1998 Nov 27; 440(1-2): 8-12 |
| SOCS1 | Phosphorylation | Kinjyo et al., Immunity. 2002 Nov; 17(5): 583-91; Nakagawa et al., Immunity. 2002 Nov; 17(5): 677-87 |
| Statins (several) | Phosphorylation | Hilgendorff et al., Int J Clin Pharmacol Ther. 2003 Sep; 41(9): 397-401; Han et al., 2004; Planavila et al., Biochim Biophys Acta. 2005 Feb 21; 1687(1-3): 76-83 |

TABLE 2B-continued

IκBα PHOSPHORYLATION AND/OR DEGRADATION INHIBITORS

| Molecule | Point of Inhibition | References |
| --- | --- | --- |
| Sulindac | IKK/Phosphorylation | Yamamato et al., J Biol Chem. 1999 Sep 17; 274(38): 27307-14 |
| THI 52 (1-naphthylethyl-6,7-dihydroxy-1,2,3,4-tetrahydroisoquinoline) | Phosphorylation | Kang et al., Biochem Pharmacol. 2003 Feb 1; 65(3): 457-64 |
| 1,2,4-thiadiazolidine derivatives | Phosphorylation | Manna et al., Int J Cancer. 2005 Feb 10; 113(4): 549-60 |
| Vesnarinone | Phosphorylation | Manna & Aggarwal, J Immunol. 2000 Jun 1; 164(11): 5815-25; Harada et al., Int J Oncol. 2005 Dec; 27(6): 1489-97 |
| Xanthoangelol D | Phosphorylation | Sugii et al., Biol Pharm Bull. 2005 Apr; 28(4): 607-10. |
| YC-1 | Phosphorylation | Huang et al., Mol Cancer Ther. 2005 Oct; 4(10): 1628-35 |
| YopJ (encoded by *Yersinia pseudotuberculosis*) | Deubiquintinase for IkBa | Schesser et al., Mol Microbiol. 1998 Jun; 28(6): 1067-79; Zhou et al., J Exp Med. 2005 Nov 21; 202(10): 1327-32 |
| Acetaminophen | Degradation | Mancini et al., Neurosci Lett. 2003 Dec 19; 353(2): 79-82 |
| Activated Protein C (APC) | Degradation | Yuksel et al., Thromb Haemost. 2002 Aug; 88(2): 267-73 |
| Alachlor | Degradation | Shimomura-Shimizu et al., Biochem Biophys Res Commun. 2005 Jul 8; 332(3): 793-9 |
| a-melanocyte-stimulating hormone (a-MSH) | Degradation | Manna & Aggarwal, J Immunol. 1998 Sep 15; 161(6): 2873-80 |
| Amentoflavone | Degradation | Banerjee et al., Mol Cell Biochem. 2002 Sep; 238(1-2): 105-10 |
| *Artemisia capillaris* Thunb extract | Degradation | Hong et al., Int J Mol Med. 2004 May; 13(5): 717-20 |
| *Artemisia iwayomogi* extract | Degradation | Kim et al., Exp Biol Med (Maywood). 2005 Jan; 230(1): 82-8 |
| L-ascorbic acid | Degradation | Han et al., J Cell Biochem. 2004 Oct 1; 93(2): 257-70 |
| *Antrodia camphorata* | Degradation | Hseu et al., Int Immunopharmacol. 2005 Dec; 5(13-14): 1914-25. Epub 2005 Jul 18 |
| Aucubin | Degradation | Jeong et al., Cytokine. 2002 Jun 7; 18(5): 252-9. |
| Baicalein | Degradation | Ma et al., Blood. 2005 Apr 15; 105(8): 3312-8. Epub 2004 Dec 30 |
| beta-lapachone | Degradation | Manna et al., Biochem Pharmacol. 1999 Apr 1; 57(7): 763-74 |
| Blackberry extract | Degradation | Pergola et al., Nitric Oxide. 2006 Aug; 15(1): 30-9. Epub 2006 Mar 6 |
| 1-Bromopropane | Degradation | Yoshida et al., Neurotoxicology. 2006 Jun 2; [Epub ahead of print] |
| Buchang-tang | Degradation | Shin et al., J Ethnopharmacol. 2005 Oct 31; 102(1): 95-101 |
| Capsaicin (8-methyl-N-vanillyl-6-nonenamide) | Degradation | Singh. et al., J Immunol. 1996 Nov 15; 157(10): 4412-20; Mori et al., Cancer Res. 2006 Mar 15; 66(6): 3222-9 |
| Catalposide | Degradation | Kim et al., Inflamm Bowel Dis. 2004 Sep; 10(5): 564-72 |
| Cyclolinteinone (sponge sesterterpene) | Degradation | D'Acquisto et al., Biochem J. 2000 Mar 15; 346 Pt 3: 793-8 |
| DA-9601 (*Artemisia asiatica* extract) | Degradation | Choi et al., World J Gastroenterol. 2006 Aug 14; 12(30): 4850-8 |
| Diamide (tyrosine phosphatase inhibitor) | Degradation | Toledano & Leonard, Proc Natl Acad Sci USA. 1991 May 15; 88(10): 4328-32; Singh & Aggarwal, J Biol Chem. 1995 May 5; 270(18): 10631-9. |
| Dihydroarteanniun | Degradation | Li et al., Int Immunopharmacol. 2006 Aug; 6(8): 1243-50. Epub 2006 Apr 7 |
| Dobutamine | Degradation | Loop et al., Anesth Analg. 2004 Nov; 99(5): 1508-15; table of contents. |

TABLE 2B-continued

IκBα PHOSPHORYLATION AND/OR DEGRADATION INHIBITORS

| Molecule | Point of Inhibition | References |
| --- | --- | --- |
| Docosahexaenoic acid | Degradation | Weldon et al., J Nutr Biochem. 2006 Jun 15; [Epub ahead of print] |
| E-73 (cycloheximide analog) | Degradation | Sugimoto et al., Biochem Biophys Res Commun. 2000 Oct 22; 277(2): 330-3 |
| Ecabet sodium | Degradation | Kim et al., Helicobacter. 2003; 8(5): 542-53 |
| Electrical stimulation of vagus nerve | Degradation | Guarini et al., Circulation. 2003 Mar 4; 107(8): 1189-94 |
| Emodin (3-methyl-1,6,8-trihydroxyanthraquinone) | Degradation | Kumar et al., Oncogene. 1998 Aug 20; 17(7): 913-8; Huang et al., Biochem Pharmacol. 2004 Jul 15; 68(2): 361-71 |
| *Ephedrae herba* (Mao) | Degradation | Aoki et al., J Pharmacol Sci. 2005 Jul; 98(3): 327-30. Epub 2005 Jul 9 |
| Equol | Degradation | Kang et al., Biochem Pharmacol. 2005 Dec 19; 71(1-2): 136-43. Epub 2005 Nov 10 |
| Erbstatin (tyrosine kinase inhibitor) | Degradation | Natarajan et al., Arch Biochem Biophys. 1998 Apr 1; 352(1): 59-70 |
| Estrogen (E2) | Degradation/and various other steps | Sun et al., Biochem Biophys Res Commun. 1998 Mar 27; 244(3): 691-5; Kalaitzidis & Gilmore, Trends Endocrinol Metab. 2005 Mar; 16(2): 46-52; Steffan et al., Curr Top Med Chem. 2006; 6(2): 103-11. |
| Ethacrynic acid | Degradation (and DNA binding) | Han et al., 2004 |
| Fosfomycin | Degradation | Yoneshima et al., Int J Antimicrob Agents. 2003 Jun; 21(6): 589-92 |
| Fungal gliotoxin | Degradation | Pahl et al., Oncogene. 1999 Nov 22; 18(49): 6853-66 |
| Gabexate mesilate | Degradation | Yuksel et al., J Pharmacol Exp Ther. 2003 Apr; 305(1): 298-305 |
| Gamisanghyulyunbueum | Degradation | Shin et al., Biol Pharm Bull. 2005 Jul; 28(7): 1177-82 |
| Genistein (tyrosine kinase inhibitor) | Degradation; caspase cleavage of IkBa | Natarajan et al., Arch Biochem Biophys. 1998 Apr 1; 352(1): 59-70; Baxa & Yoshimura, Biochem Pharmacol. 2003 Sep 15; 66(6): 1009-18. |
| Genipin | Degradation | Koo et al., Eur J Pharmacol. 2004 Jul 14; 495(2-3): 201-8 |
| Glabridin | Degradation | Kang et al., J Pharmacol Exp Ther. 2005 Mar; 312(3): 1187-94. Epub 2004 Nov 10 |
| Glimepiride | Degradation | Schiekofer et al., Diabetes Obes Metab. 2003 Jul; 5(4): 251-61 |
| Glucosamine sulfate | Degradation | Largo et al., Osteoarthritis Cartilage. 2003 Apr; 11(4): 290-8 |
| gamma-glutamylcysteine synthetase | Degradation | Manna et al., Oncogene. 1999 Jul 29; 18(30): 4371-82. |
| Glutamine | Degradation | Singleton et al., Shock. 2005 Dec; 24(6): 583-9 |
| Gumiganghwaltang | Degradation | Kim et al., Biol Pharm Bull. 2005 Feb; 28(2): 233-7 |
| Heat shock protein-70 | Degradation | Chan et al., Circulation. 2004 Dec 7; 110(23): 3560-6. Epub 2004 Nov 22.; Shi et al., Shock. 2006 Sep; 26(3): 277-84 |
| Hypochlorite | Degradation | Mohri et al., Invest Ophthalmol Vis Sci. 2002 Oct; 43(10): 3190-5. |
| IL-13 | Degradation | Manna & Aggarwal, J Immunol. 1998 Sep 15; 161(6): 2863-72 |
| Intravenous immunoglobulin | Degradation | Ichiyama et al., Inflamm Res. 2004 Jun; 53(6): 253-6. Epub 2004 May 12 |
| Isomallotochromanol and isomallotochromene | Degradation | Ishii et al., Biochim Biophys Acta. 2003 Mar 17; 1620(1-3): 108-18 |

TABLE 2B-continued

IκBα PHOSPHORYLATION AND/OR DEGRADATION INHIBITORS

| Molecule | Point of Inhibition | References |
|---|---|---|
| K1L (Vaccinia virus protein) | Degradation | Shisler & Jin, J Virol. 2004 Apr; 78(7): 3553-60 |
| *Kochia scoparia* fruit (methanol extract) | Degradation | Shin et al., Biol Pharm Bull. 2004 Apr; 27(4): 538-43 |
| Leflunomide metabolite (A77 1726) | Degradation | Manna & Aggarwal, J Immunol. 1999 Feb 15; 162(4): 2095-102 |
| Losartin | Degradation | Chen et al., 2002 |
| Low level laser therapy | Degradation | Rizzi et al., Lasers Surg Med. 2006 Aug; 38(7): 704-13 |
| LY294002 (PI3-kinase inhibitor) [2-(4-morpholinyl)-8-phenylchromone] | Degradation | Park et al., Cell Biol Toxicol. 2002; 18(2): 121-30. |
| MC159 (Molluscum contagiosum virus) | Degradation of IkBb | Murao & Shisler, 2005 |
| Melatonin | Degradation | Zhang et al., Eur J Pharmacol. 2004 Oct 6; 501(1-3): 25-30 |
| 5'-methylthioadenosine | Degradation | Hevia et al., Hepatology. 2004 Apr; 39(4): 1088-98. |
| Midazolam | Degradation | Kim et al., Anesthesiology. 2006 Jul; 105(1): 105-10 |
| Momordin I | Degradation | Hwang et al., Biochem Biophys Res Commun. 2005 Nov 25; 337(3): 815-23. Epub 2005 Sep 28. |
| *Morinda officinalis* extract | Degradation | Kim et al., J Pharm Pharmacol. 2005 May; 57(5): 607-15 |
| *Mosla dianthera* extract | Degradation | Lee et al., Toxicol Appl Pharmacol. 2006 Jun 22; [Epub ahead of print] |
| Murr1 gene product | Degradation | Ganesh et al., Nature. 2003 Dec 18; 426(6968): 853-7. |
| Neurofibromatosis-2 (NF-2; merlin) protein | Degradation | Kim et al., Biochem Biophys Res Commun. 2002 Sep 6; 296(5): 1295-302 |
| *Opuntia ficus* indica va saboten extract | Degradation | Lee et al., 2006 |
| Penetratin | Degradation | Letoya et al., Mol Pharmacol. 2006 Jun; 69(6): 2027-36. Epub 2006 Feb 27. |
| Pervanadate (tyrosine phosphatase inhibitor) | Degradation | Singh & Aggarwal, J Biol Chem. 1995 May 5; 270(18): 10631-9; Singh et al., J Biol Chem. 1996 Dec 6; 271(49): 31049-54 |
| Phenylarsine oxide (PAO, tyrosine phosphatase inhibitor) | Degradation | Mahboubi et al., J Pharmacol Exp Ther. 1998 May; 285(2): 862-8; Singh & Aggarwal, J Biol Chem. 1995 May 5; 270(18): 10631-9 |
| beta-Phenylethyl (PEITC) and 8-methylsulphinyloctyl isothiocyanates (MSO) (watercress) | Degradation | Rose et al., Nitric Oxide. 2005 Jun; 12(4): 237-43 |
| Phenytoin | Degradation | Kato et al., 2005 |
| *Platycodin saponins* | Degradation | Ahn et al., Life Sci. 2005 Apr 1; 76(20): 2315-28 |
| Polymyxin B | Degradation | Jiang et al., Chin Med J (Engl). 2006 Mar 5; 119(5): 384-90. |
| *Poncirus trifoliata* fruit extract | Degradation | Shin et al., Toxicol In vitro. 2006 Oct; 20(7): 1071-6. Epub 2006 Mar 6 |
| Probiotics | Degradation | Petrof et al., Gastroenterology. 2004 Nov; 127(5): 1474-87. |
| Pituitary adenylate cyclase-activating polypeptide (PACAP) | Degradation | Delgado & Ganea, J Biol Chem. 2001 Jan 5; 276(1): 369-80 |
| Prostaglandin 15-deoxy-Delta(12,14)-PGJ(2) | Degradation | Cuzzocrea et al., Br J Pharmacol. 2003 Feb; 138(4): 678-88; Chatterjee et al., Cardiovasc Res. 2004 Feb 15; 61(3): 630-43 |
| PS-341 | Degradation/proteasome | Hideshima et al., J Biol Chem. 2002 May 10; 277(19): 16639-47. Epub 2002 Feb 28 |
| Resiniferatoxin | Degradation | Singh et al., J Immunol. 1996 Nov 15; 157(10): 4412-20 |
| Sabaeksan | Degradation | Choi et al., Exp Mol Pathol. 2005 Jun; 78(3): 257-62. Epub 2005 Feb 17 |

TABLE 2B-continued

IκBα PHOSPHORYLATION AND/OR DEGRADATION INHIBITORS

| Molecule | Point of Inhibition | References |
|---|---|---|
| SAIF (*Saccharomyces boulardii* anti-inflammatory factor) | Degradation | Sougioultzis et al., Biochem Biophys Res Commun. 2006 Apr 28; 343(1): 69-76. Epub 2006 Feb 23. |
| Sesquiterpene lactones (parthenolide; ergolide; guaianolides) | Degradation | Hehner et al., J Biol Chem. 1998 Jan 16; 273(3): 1288-97; Whan Han et al., Br J Pharmacol. 2001 Jun; 133(4): 503-12.; Schorr et al., Phytochemistry. 2002 Aug; 60(7): 733-40 |
| ST2 (IL-1-like receptor secreted form) | Degradation | Takezako et al., Biochem Biophys Res Commun. 2006 Mar 10; 341(2): 425-32. Epub 2006 Jan 11 |
| Thiopental | Degradation | Loop et al., Anesthesiology. 2002 May; 96(5): 1202-13 |
| Tipifarnib | Degradation | Xue et al., J Pharmacol Exp Ther. 2006 Apr; 317(1): 53-60. Epub 2005 Dec 13 |
| Titanium | Degradation | Yang et al., J Biomed Mater Res A. 2003 Sep 15; 66(4): 802-10 |
| TNP-470 (angiogenesis inhibitor) | Degradation | Mauriz et al., Free Radic Res. 2003 Aug; 37(8): 841-8 |
| Stinging nettle (*Urtica dioica*) plant extracts | Degradation | Riehemann et al., FEBS Lett. 1999 Jan 8; 442(1): 89-94 |
| *Trichomomas vaginalis* infection | Degradation | Chang et al., Mol Cells. 2004 Oct 31; 18(2): 177-85 |
| Triglyceride-rich lipoproteins | Degradation | Kumwenda et al., Shock. 2002 Aug; 18(2): 182-8 |
| U0126 (MEK inhibitor) | Degradation | Takaya et al., Am J Physiol Renal Physiol. 2003 May; 284(5): F1037-45. Epub 2003 Jan 7 |
| Ursodeoxycholic acid | Degradation | Joo et al., Arch Pharm Res. 2004 Sep; 27(9): 954-60 |
| *Xanthium strumarium* L. (methanol extract) | Degradation | Kim et al., Biol Pharm Bull. 2005 Jan; 28(1): 94-100 |
| Zinc | Degradation | Uzzo et al., Carcinogenesis. 2006 Oct; 27(10): 1980-90. Epub 2006 Apr 10; Bao et al., Toxicol Lett. 2006 Oct 25; 166(3): 222-8. Epub 2006 Jul 18 |
| Molluscum contagiosum virus MC159 protein | IkBbeta degradation | Murao & Shisler, Virology. 2005 Sep 30; 340(2): 255-64 |
| Vasoactive intestinal peptide | Degradation (and CBP-RelA interaction) | Delgado & Ganea, J Biol Chem. 2001 Jan 5; 276(1): 369-80; Delgado, Biochem Biophys Res Commun. 2002 Oct 11; 297(5): 1181-5 |
| HIV-1 Vpu protein | TrCP ubiquitin ligase inhibitor | Bour et al., J Biol Chem. 2001 May 11; 276(19): 15920-8. Epub 2001 Feb 16 |
| Epoxyquinone A monomer | IKKb/DNA binding | Liang et al., Biochem Pharmacol. 2006 Feb 28; 71(5): 634-45. Epub 2005 Dec 19 |
| Ro106-9920 (small molecule) | IkBa ubiqutination inhibitor | Swinney et al., J Biol Chem. 2002 Jun 28; 277(26): 23573-81. Epub 2002 Apr 11 |

TABLE 3

MISCELLANEOUS INHIBITORS OF NF-κB

| Inhibitor Molecule | Effect or point of inhibition | References |
|---|---|---|
| Conophylline (*Ervatamia microphylla*) | Down regulated TNF-Receptors | Gohda et al., 2003 Int J Oncol. 23(5): 1373-9 |
| MOL 294 (small molecule) | Redox regulated activation of NF-κB | Henderson et al., J Immunol. 2002 Nov 1; 169(9): 5294-9 |
| PEDF (pigment epithelium derived factor) | ROS generation | Yamagishi et al., J Mol Cell Cardiol. 2004 Aug; 37(2): 497-506. |

TABLE 3-continued

MISCELLANEOUS INHIBITORS OF NF-κB

| Inhibitor Molecule | Effect or point of inhibition | References |
|---|---|---|
| Perrilyl alcohol | Calcium pathway | Berchtold et al., Cancer Res. 2005 Sep 15; 65(18): 8558-66. |
| MAST205 | TRAF6 binding | Xiong et al., J Biol Chem. 2004 Oct 15; 279(42): 43675-83. Epub 2004 Aug 11. |
| Rhein | MEKK activation of NF-κB | Martin et al., Inflammation. 2003 Aug; 27(4): 233-46; Domagala et al., Biorheology. 2006; 43(3-4): 577-87. |
| 15-deoxy-prostaglandin J(2) | PPARg activation of NF-κB | Boyault et al., FEBS Lett. 2004 Aug 13; 572(1-3): 33-40. |
| *Antrodia camphorata* extract | IkBa upregulation | Hsu et al., Cancer Lett. 2005 Apr 18; 221(1): 77-89. |
| apigenin (4',5,7-trihydroxyflavone) | IkBa upregulation | Shukla & Gupta, Clin Cancer Res. 2004 May 1; 10(9): 3169-78. |
| beta-amyloid protein | IkBa upregulation | Bales et al., Brain Res Mol Brain Res. 1998 Jun 1; 57(1): 63-72 |
| human breast milk | IkBa upregulation | Minekawa et al., Am J Physiol Cell Physiol. 2004 Nov; 287(5): C1404-11. Epub 2004 Jun 30 |
| Surfactant protein A (SP-A) | IkBa upregulation | Wu et al., Am J Respir Cell Mol Biol. 2004 Dec; 31(6): 587-94. Epub 2004 Aug 12 |
| DQ 65-79 (aa 65-79 of the alpha helix of the alpha-chain of the class II HLA molecule DQA03011) | IkBa upregulation and IKK inhibition | Jiang et al., J Immunol. 2002 Apr 1; 168(7): 3323-8. |
| C5a | IkBa upregulation | Riedemann et al., Immunity. 2003 Aug; 19(2): 193-202. |
| Glucocorticoids (dexamethasone, prednisone, methylprednisolone) | IkBa upregulation | Auphan et al., Science. 1995 Oct 13; 270(5234): 286-90; Brostjan et al., J Biol Chem. 1996 Aug 9; 271(32): 19612-6; Ray & Prefontaine, Proc Natl Acad Sci USA. 1994 Jan 18; 91(2): 752-6; Scheinman et al., Mol Cell Biol. 1995 Feb; 15(2): 943-53. |
| IL-10 | IkBa upregulation | Ehrlich et al., Neuroreport. 1998 Jun 1; 9(8): 1723-6; Lentsch et al., J Clin Invest. 1997 Nov 15; 100(10): 2443-8; Shames et al., Shock. 1998 Dec; 10(6): 389-94 |
| IL-13 | IkBa upregulation | Ehrlich et al., Neuroreport. 1998 Jun 1; 9(8): 1723-6; Lentsch et al., J Clin Invest. 1997 Nov 15; 100(10): 2443-8; Manna & Aggarwal, J Immunol. 1998 Sep 15; 161(6): 2863-72. |
| IL-11 | IKKa; IkBa, IkBb upregulation | Trepicchio & Dorner, Ann NY Acad Sci. 1998 Sep 29; 856: 12-21; Lgssiar et al., Exp Biol Med (Maywood). 2004 May; 229(5): 425-36. |
| alpha-pinene | IkBa upregulation | Zhou et al., Acta Pharmacol Sin. 2004 Apr; 25(4): 480-4. |
| NEF (HIV-1) | IkBa upregulation | Qiao et al., Nat Immunol. 2006 Mar; 7(3): 302-10. Epub 2006 Jan 22. |
| R-etodolac | IkBa upregulation | Neri et al., Br J Haematol. 2006 Jul; 134(1): 37-44. |
| Vitamin D | IkBa upregulation | Cohen-Lahav et al., Nephrol Dial Transplant. 2006 Apr; 21(4): 889-97. Epub 2006 Feb 2. |
| Fox1j | IkBb upregulation | Lin et al., 2004 |
| Dioxin | RelA nuclear transport | Ruby et al., Mol Pharmacol. 2002 Sep; 62(3): 722-8 |
| *Agastache rugosa* leaf extract | Nuclear translocation | Oh et al., Arch Pharm Res. 2005 Mar; 28(3): 305-10. |
| Alginic acid | Nuclear translocation | Jeong et al., Clin Exp Allergy. 2006 Jun; 36(6): 785-94. |
| Astragaloside IV | Nuclear translocation | Zhang et al., Thromb Haemost. 2003 Nov; 90(5): 904-14. |

TABLE 3-continued

MISCELLANEOUS INHIBITORS OF NF-κB

| Inhibitor Molecule | Effect or point of inhibition | References |
| --- | --- | --- |
| Atorvastatin | Nuclear translocation | Haloui et al., Eur J Pharmacol. 2003 Aug 8; 474(2-3): 175-84. |
| Blue honeysuckle extract | Nuclear translocation | Jin et al., Exp Eye Res. 2006 May; 82(5): 860-7. Epub 2005 Nov 23. |
| BMD (N(1)-Benzyl-4-methylbenzene-1,2-diamine) | Nuclear translocation | Shin et al., Eur J Pharmacol. 2005 Oct 3; 521(1-3): 1-8. Epub 2005 Sep 23. |
| *Buthus martensi* Karsch extract | Nuclear translocation | Kim et al., 2005 |
| Canine Distemper Virus | Nuclear translocation | Friess et al., J Comp Pathol. 2005 Jan; 132(1): 82-9. |
| Carbaryl | Nuclear translocation | Shimomura-Shimizu et al., Biochem Biophys Res Commun. 2005 Jul 8; 332(3): 793-9. |
| Celastrol | Nuclear translocation | Pinna et al., Biochem Biophys Res Commun. 2004 Sep 24; 322(3): 778-86. |
| Chiisanoside | RelA Nuclear translocation | Won et al., Biol Pharm Bull. 2005 Oct; 28(10): 1919-24. |
| CP-1158 | Nuclear translocation | Kim et al., Eur J Pharmacol. 2006 Aug 14; 543(1-3): 158-65. Epub 2006 Jun 2. |
| Dehydroxymethylepoxyquinomicin (DHMEQ) | Nuclear translocation | Chaicharoenpong et al., Bioorg Med Chem. 2002 Dec; 10(12): 3933-9 |
| 15-deoxyspergualin | Nuclear translocation | Hutchings et al., Transpl Immunol. 2003 Jul-Sep; 11(3-4): 335-44. |
| Dipyridamole | Nuclear translocation | Weyrich et al., Circulation. 2005 Feb 8; 111(5): 633-42. Epub 2005 Jan 24. |
| Disulfiram | Nuclear translocation | Wang et al., Int J Cancer. 2003 Apr 20; 104(4): 504-11. |
| Diltiazem | Nuclear translocation; induced translocation of p50 dimers | Severa et al., Biochem Pharmacol. 2005 Feb 1; 69(3): 425-32. Epub 2004 Dec 9. |
| Eriocalyxin B | Nuclear translocation/DNA binding | Wang et al., Cell Death Differ. 2006 Jun 16; [Epub ahead of print]; Leung et al., Mol Pharmacol. 2006 Aug 29; [Epub ahead of print] |
| Estrogen enhanced transcript | Nuclear translocation | Jin et al., Cell Immunol. 2003 May; 223(1): 26-34. |
| FAK-related nonkinase | Nuclear translocation | Qin & Liu, Acta Pharmacol Sin. 2006 Sep; 27(9): 1159-64 |
| Gangliosides | Nuclear translocation | Caldwell et al., J Immunol. 2003 Aug 15; 171(4): 1676-83. |
| Glucorticoid-induced leucine zipper protein (GILZ) | Nuclear translocation | Riccardi et al., Adv Exp Med Biol. 2001; 495: 31-9. |
| *Harpagophytum procumbens* (Devil's Claw) extracts | Nuclear translocation | Kaszkin et al., Phytomedicine. 2004 Nov; 11(7-8): 585-95. |
| Heat shock protein 72 | Nuclear translocation | Meldrum et al., Circ Res. 2003 Feb 21; 92(3): 293-9 |
| Hirsutenone | Nuclear translocation | Kim et al., FEBS Lett. 2006 Jan 23; 580(2): 385-92. Epub 2005 Dec 19 |
| Indole-3-carbinol | Nuclear translocation | Rahman & Sarkar, Cancer Res. 2005 Jan 1; 65(1): 364-71 |
| JM34 (benzamide derivative) | Nuclear translocation | Carbonnelle et al., 2005 |
| JSH-23 (4-Methyl--(3-phenyl-propyl)-benzene-1,2-diamine | Nuclear translocation | Shin et al., FEBS Lett. 2004 Jul 30; 571(1-3): 50-4 |
| KIOM-79 (combined plant extracts) | Nuclear translocation | Jeon et al., J Ethnopharmacol. 2006 Apr 28; [Epub ahead of print] |
| KL-1156 (6-Hydroxy-7-methoxychroman-2-carboxylic acid phenylamide) | Nuclear translocation | Kim et al., Biochem Biophys Res Commun. 2004 Dec 3; 325(1): 223-8. |
| Leptomycin B (LMB) | Nuclear translocation | Rodriguez et al., J Biol Chem. 1999 Mar 26; 274(13): 9108-15. |

TABLE 3-continued

MISCELLANEOUS INHIBITORS OF NF-κB

| Inhibitor Molecule | Effect or point of inhibition | References |
|---|---|---|
| Levamisole | Nuclear translocation | Liu et al., J Surg Res. 2004 Apr; 117(2): 223-31. |
| MEB (2-(4-morpholynl) ethyl butyrate hydrochloride) | Nuclear translocation | Soderberg et al., Int Immunopharmacol. 2004 Sep; 4(9): 1231-9. |
| MNF (IkB-like Myxoma virus) | Nuclear translocation | Camus-Bouclainville et al., J Virol. 2004 Mar; 78(5): 2510-6. |
| Montelukast | Nuclear translocation | Wu et al., Can J Physiol Pharmacol. 2006 May; 84(5): 531-7. |
| NLS Cell permeable peptides (SN50) | Nuclear translocation | Lin et al., J Biol Chem. 1995 Jun 16; 270(24): 14255-8. |
| 2',8''-biapigenin | RelA nuclear translocation | Woo et al., Biol Pharm Bull. 2006 May; 29(5): 976-80. |
| Nucling | RelA nuclear translocation | Liu et al., Biochem J. 2004 May 15; 380(Pt 1): 31-41. |
| o,o'-bismyristoyl thiamine disulfide (BMT) | Nuclear translocation | Shoji et al., Biochem Biophys Res Commun. 1998 Aug 28; 249(3): 745-53. |
| Oregonin | RelA nuclear translocation | Lee et al., Br J Pharmacol. 2005 Oct; 146(3): 378-88 |
| 1,2,3,4,6-penta-O-galloyl-beta-d-glucose | RelA nuclear translocation | Kang et al., Eur J Pharmacol. 2005 Nov 7; 524(1-3): 111-9. Epub 2005 Oct 25 |
| *Platycodi radix* extract | RelA nuclear translocation | Lee et al., Int J Mol Med. 2004 Jun; 13(6): 843-7 |
| Phallacidin | Nuclear translocation | Papakonstanti & Strounaras, Mol Biol Cell. 2004 Mar; 15(3): 1273-86. Epub 2003 Dec 29 |
| Piperine | Nuclear translocation | Pradeep & Kuttan, Int Immunopharmacol. 2004 Dec 20; 4(14): 1795-803 |
| Pitavastatin | Nuclear translocation | Wang et al., Biol Pharm Bull. 2006 Apr; 29(4): 634-9 |
| PN-50 | Nuclear translocation | Letoha et al., World J Gastroenterol. 2005 Feb 21; 11(7): 990-9 |
| Probiotics | RelA nuclear translocation | Bai et al., World J Gastroenterol. 2004 Feb 1; 10(3): 455-7. |
| RelA peptides (P1 and P6) | Nuclear translocation | Takada et al., J Biol Chem. 2004 Apr 9; 279(15): 15096-104. Epub 2004 Jan 7. |
| Retinoic acid receptor-related orphan receptor-alpha | Nuclear translocation | Migita et al., FEBS Lett. 2004 Jan 16; 557(1-3): 269-74 |
| *Rhubarb* aqueous extract | RelA nuclear translocation | Moon et al., Life Sci. 2006 Feb 28; 78(14): 1550-7. Epub 2005 Nov 2 |
| Rolipram | Nuclear translocation | Sanchez et al., J Neuroimmunol. 2005 Nov; 168(1-2): 13-20. Epub 2005 Sep 22; Ikezoe et al., Cancer Res. 2004 Oct 15; 64(20): 7426-31. |
| *Salvia miltiorrhoza* Bunge extract | Nuclear translocation | Ding et al., J Cardiovasc Pharmacol. 2005 Jun; 45(6): 516-24 |
| SC236 (a selective COX-2 inhibitor) | Nuclear translocation | Wong et al., Oncogene. 2003 Feb 27; 22(8): 1189-97 |
| Selenomethionine | Nuclear translocation | Cherukuri et al., Cancer Biol Ther. 2005 Feb; 4(2): 175-80. Epub 2005 Feb 8 |
| ShenQi compound recipe | RelA Nuclear translocation | Zhang et al., Zhong Yao Cai. 2006 Mar; 29(3): 249-53 |
| *Sophorae radix* extract | Nuclear translocation | Kwon et al., Clin Chim Acta. 2004 Oct; 348(1-2): 79-86 |
| Sopoongsan | Nuclear translocation | Na et al., Int Arch Allergy Immunol. 2006; 139(1): 31-7. Epub 2005 Nov 3 |
| Sphondin (furanocoumarin derivative from *Heracleum laciniatum*) | Nuclear translocation | Yang et al., Life Sci. 2002 Nov 29; 72(2): 199-213 |
| TAT-SR-IkBa; MTS-SR-IkBa | Nuclear translocation | Blackwell et al., Arthritis Rheum. 2004 Aug; 50(8): 2675-84; Mora et al., Am J Physiol Lung Cell Mol Physiol. 2005 |

TABLE 3-continued

MISCELLANEOUS INHIBITORS OF NF-κB

| Inhibitor Molecule | Effect or point of inhibition | References |
|---|---|---|
| | | Oct; 289(4): L536-44. Epub 2005 Jun 10 |
| Volatile anesthetic treatment | Nuclear translocation | Lee et al., Anesthesiology. 2004 Dec; 101(6): 1313-24 |
| Younggaechulgam-tang | Nuclear translocation | Shin et al., Immunopharmacol Immunotoxicol. 2004; 26(4): 545-58 |
| ZUD protein | Activation of NF-κB; binds p105/RelA | Zhang et al., J Biol Chem. 2004 Apr 23; 279(17): 17819-25. Epub 2004 Feb 9 |
| ZAS3 protein | RelA nuclear translocation; DNA competition | Hong et al., Proc Natl Acad Sci USA. 2003 Oct 14; 100(21): 12301-6. Epub 2003 Oct 6 |
| Clarithromycin | nuclear expression | Ichiyama et al., Antimicrob Agents Chemother. 2001 Jan; 45(1): 44-7 |
| Fluvastatin | nuclear expression | Azuma et al., Cardiovasc Res. 2004 Dec 1; 64(3): 412-20 |
| Leflunomide | RelA nuclear expression | Yao et al., Acta Pharmacol Sin. 2004 Jul; 25(7): 915-20 |
| RASSF1A gene overexpression | RelA nuclear expression | Deng et al., Zhong Nan Da Xue Xue Bao Yi Xue Ban. 2005 Apr; 30(2): 193-6 |
| oxidized 1-palmitoyl-2-arachidonoyl-sn-glycero-3-phosphorylcholine (OXPAPC) | RelA expression | Li et al., Zhonghua Yi Xue Za Zhi. 2004 Aug 2; 84(15): 1235-9 |
| 3C protease (Poliovirus) | RelA expression (cleavage) | Neznanov et al., J Biol Chem. 2005 Jun 24; 280(25): 24153-8. Epub 2005 Apr 21. |
| 5F (from Pteri syeminpinnata L) | RelA expression | He et al., Zhong Yao Cai. 2005 Aug; 28(8): 672-6 |
| AT514 (serratamolide) | RelA expression | Escobar-Diaz et al., Leukemia. 2005 Apr; 19(4): 572-9 |
| *Sorbus commixta* cortex (methanol extract) | RelA expression | Sohn et al., Biol Pharm Bull. 2005 Aug; 28(8): 1444-9 |
| Cantharidin | NF-κB expression | He et al., Ai Zheng. 2005 Apr; 24(4): 443-7 |
| *Cornus officinalis* extract | NF-κB expression | Li et al., Zhongguo Zhong Yao Za Zhi. 2005 Nov; 30(21): 1667-70 |
| Neomycin | NF-κB expression | Garcia-Trapero et al., Neurol Res. 2004 Dec; 26(8): 816-24 |
| omapatrilat, enalapril, CGS 25462 | NF-κB expression | Pu et al., J Hypertens. 2005 Feb; 23(2): 401-9 |
| Onconase (Ranpirnase) | NF-κB expression | Tsai et al., Int J Oncol. 2004 Dec; 25(6): 1745-52 |
| Paeoniflorin | NF-κB expression | Liu et al., Brain Res. 2006 May 17; 1089(1): 162-70. Epub 2006 May 5 |
| Rapamycin | NF-κB expression | Lawrence et al., J Vasc Surg. 2004 Aug; 40(2): 334-8 |
| *Sargassum hemiphyllum* methanol extract | NF-κB expression | Na et al., J Pharmacol Sci. 2005 Feb; 97(2): 219-26. Epub 2005 Feb 5 |
| Shenfu | NF-κB expression | Zhang et al., Chin J Traumatol. 2005 Aug 1; 8(4): 200-4 |
| Tripterygium polyglycosides | NF-κB expression | Zhou et al., Zhongguo Zhong Xi Yi Jie He Za Zhi. 2005 Aug; 25(8): 723-6 |
| Triflusal | nuclear expression | Acarin et al., Neurosci Lett. 2000 Jul 7; 288(1): 41-4 |
| HSCO (hepatoma protein) | Accelerates RelA nuclear export | Higashitsuji et al., Cancer Cell. 2002 Oct; 2(4): 335-46 |
| Andrographolide | Covlalent adduct with Cys-62 of p50 | Xia et al., J Immunol. 2004 Sep 15; 173(6): 4207-17 |
| Bee venom (melittin) | DNA binding by binding to p50 | Park et al., Arthritis Rheum. 2004 Nov; 50(11): 3504-15 |
| Ethyl pyruvate | DNA binding by RelA thru Cys-38 | Han et al., J Pharmacol Exp Ther. 2005 Mar; 312(3): 1097-105. Epub 2004 Nov 3 |
| 1'-acetoxychavicol acetate | DNA binding | Ito et al., Biochem Biophys Res Commun. 2005 Dec 30; 338(4): 1702-10. Epub 2005 Nov 2 |
| 2-acetylaminofluorene | DNA binding | Kang et al., Cancer Lett. 2004 Jan 8; 203(1): 91-8; |

TABLE 3-continued

| MISCELLANEOUS INHIBITORS OF NF-κB | | |
|---|---|---|
| Inhibitor Molecule | Effect or point of inhibition | References |
| Actinodaphine (from *Cinnamomum insularimontanum*) | DNA binding | Jeon et al., Toxicol Lett. 1999 Feb 22; 104(3): 195-202 Hsieh et al., Food Chem Toxicol. 2006 Mar; 44(3): 344-54. Epub 2005 Sep 15 |
| Adiponectin | DNA binding | Ajuwon & Spurlock, Am J Physiol Regul Integr Comp Physiol. 2005 May; 288(5): R1220-5. Epub 2004 Dec 16 |
| ADP ribosylation inhibitors (nicotinamide, 3-aminobenzamide) | DNA binding | Le Page et al., Biochem Biophys Res Commun. 1998 Feb 13; 243(2): 451-7 |
| AIM2 (Absent In Melanoma protein) overexpression | DNA binding | Chen et al., Mol Cancer Ther. 2006 Jan; 5(1): 1-7 |
| Moderate alcohol intake | DNA binding | Mandrekar et al., Alcohol Clin Exp Res. 2006 Jan; 30(1): 135-9 |
| 7-amino-4-methylcoumarin | DNA binding | Kurokawa et al., Eur J Pharmacol. 2003 Aug 8; 474(2-3): 283-93 |
| Amrinone | DNA binding | Chanani et al., Circulation. 2002 Sep 24; 106(12 Suppl 1): I284-9. |
| Angiopoietin-1 | DNA binding | Jeon et al., Circ Res. 2003 Apr 4; 92(6): 586-8 |
| Anthocyanins (soybean) | DNA binding | Kim et al., FEBS Lett. 2006 Feb 20; 580(5): 1391-7. Epub 2006 Jan 26 |
| *Arnica montana* extract (sequiterpene lactones) | DNA binding | Kos et al., Planta Med. 2005 Nov; 71(11): 1044-52 |
| Artemisinin | DNA binding | Aldieri et al., FEBS Lett. 2003 Sep 25; 552(2-3): 141-4; Wang et al., Antimicrob Agents Chemother. 2006 Jul; 50(7): 2420-7 |
| Atrial Natriuretic Peptide (ANP) | DNA binding; IkBa upregulation | Gerbes et al., Hepatology. 1998 Nov; 28(5): 1309-17; Kiemer et al., Biochem Biophys Res Commun. 2002 Aug 2; 295(5): 1068-76. |
| Atrovastat (HMG-CoA reductase inhibitor) | DNA binding | Bustos et al., J Am Coll Cardiol. 1998 Dec; 32(7): 2057-64; Hernandez-Presa et al., Am J Pathol. 1998 Dec; 153(6): 1825-37 |
| AvrA protein (*Salmonella*) | DNA binding | Collier-Hyams et al., J Immunol. 2002 Sep 15; 169(6): 2846-50 |
| Baicalein (5,6,7-trihydroxyflavone) | DNA binding | Suk et al., J Pharmacol Exp Ther. 2003 May; 305(2): 638-45. Epub 2003 Jan 21 |
| Bambara groundnut (*Vignea subterranean*) | DNA binding | Na et al., Biofactors. 2004; 21(1-4): 149-53 |
| Benfotiamine (thiamine derivative) | DNA binding | Hammes et al., Nat Med. 2003 Mar; 9(3): 294-9. Epub 2003 Feb 18 |
| beta-catenin | DNA binding | Deng et al., Cancer Cell. 2002 Oct; 2(4): 323-34 |
| beta-lapachone (a 1,2-naphthoquinone) | DNA binding | Tzeng et al., Am J Respir Crit Care Med. 2003 Jul 1; 168(1): 85-91. Epub 2003 Apr 30 |
| Biliverdin | DNA binding | Yamashita et al., FASEB J. 2004 Apr; 18(6): 765-7. Epub 2004 Feb 20 |
| Bisphenol A | DNA binding | Kim & Jeong, Cancer Lett. 2003 Jun 30; 196(1): 69-76 |
| Bovine serum albumin | DNA binding | Zhang & Frei, Cardiovasc Res. 2002 Sep; 55(4): 820-9 |
| Brazilian green propolis | DNA binding | Bae et al., Eur J Pharmacol. 2005 Apr 25; 513(3): 237-42. Epub 2005 Apr 15; Paulino et al., Planta Med. 2006 Aug; 72(10): 899-906. Epub 2006 Aug 10 |
| Bromelain | DNA binding | Hou et al., J Agric Food Chem. 2006 Mar 22; 54(6): 2193-8 |
| Calcium/calmodulin-dependent kinase kinase (CaMKK) (and increased intracellular calcium by | DNA binding | Chen et al., J Biol Chem. 2002 Jul 5; 277(27): 24169-79. Epub 2002 Apr 25 |

TABLE 3-continued

MISCELLANEOUS INHIBITORS OF NF-κB

| Inhibitor Molecule | Effect or point of inhibition | References |
|---|---|---|
| ionomycin, UTP and thapsigargin) | | |
| Calcitriol (1a,25-dihydroxyvitamin D3) | DNA binding | Harant et al., Eur J Biochem. 1997 Nov 15; 250(1): 63-71 |
| Campthothecin | DNA binding | Hentze et al., Hepatology. 2004 May; 39(5): 1311-20 |
| Cancer bush (*Sutherlandia frutescens*) | DNA binding | Na et al., Biofactors. 2004; 21(1-4): 149-53 |
| Caprofen | DNA binding | Bryant et al., Am J Vet Res. 2003 Feb; 64(2): 211-5 |
| Capsiate | DNA binding | Sancho et al., Eur J Immunol. 2002 Jun; 32(6): 1753-63 |
| Carbocisteine | DNA binding | Yasuda et al., Eur Respir J. 2006 Jul; 28(1): 51-8. Epub 2006 Mar 1 |
| Catalposide (stem bark) | DNA binding | Oh et al., Planta Med. 2002 Aug; 68(8): 685-9 |
| Cat's claw bark (*Uncaria tomentosa*; *Rubiaceae*); Maca | DNA binding | Aguilar et al., J Ethnopharmacol. 2002 Jul; 81(2): 271-6; Valerio & Gonzales, Toxicol Rev. 2005; 24(1): 11-35 |
| CD43 overexpression | DNA binding (RelA) | Laos et al., Int J Oncol. 2006 Mar; 28(3): 695-704 |
| Celecoxib and germcitabine | DNA binding | El-Rayes et al., Mol Cancer Ther. 2004 Nov; 3(11): 1421-6 |
| Cheongyeolsaseuptang | DNA binding | Kim et al., J Ethnopharmacol. 2005 Feb 10; 97(1): 83-8. Epub 2004 Dec 10 |
| Chitosan | DNA binding | Seo et al., Biol Pharm Bull. 2003 May; 26(5): 717-21 |
| Cinnamaldehyde, 2-methoxycinnamaldehyde, 2-hydroxycinnamaldehyde | DNA binding | Reddy et al., Planta Med. 2004 Sep; 70(9): 823-7; Lee et al., Biochem Pharmacol. 2005 Mar 1; 69(5): 791-9. Epub 2005 Jan 16 |
| Chicory root (guaianolide 8-deoxylactucin) | DNA binding | Cavin et al., Biochem Biophys Res Commun. 2005 Feb 18; 327(3): 742-9 |
| Chlorophyllin | DNA binding | Yun et al., Int Immunopharmacol. 2005 Dec; 5(13-14): 1926-35. Epub 2005 Jul 6. |
| Chondrotin sulfate proteoglycan degradation product | DNA binding | Rolls et al., FASEB J. 2006 Mar; 20(3): 547-9. Epub 2006 Jan 5 |
| Clarithromycin | DNA binding | Miyanohara et al., Laryngoscope. 2000 Jan; 110(1): 126-31 |
| Cloricromene | DNA binding | Ianaro et al., Naunyn Schmiedebergs Arch Pharmacol. 2004 Aug; 370(2): 140-5. Epub 2004 Jul 30 |
| Cocaethylene | DNA binding | Tacker et al., Clin Chem. 2006 Oct; 52(10): 1926-33. Epub 2006 Aug 17 |
| Commerical peritoneal dialysis solution | DNA binding | Douvdevani et al., Kidney Int. 1995 Jun; 47(6): 1537-45 |
| Compound K (from *Panax ginseng*) | DNA binding | Park et al., Biol Pharm Bull. 2005 Apr; 28(4): 652-6. |
| *Cortex cinnamomi* extract | DNA binding | Kwon et al., World J Gastroenterol. 2006 Jul 21; 12(27): 4331-7 |
| CP Compound (6-Hydroxy-7-methoxychroman-2-carboxylic acid phenylamide) | DNA binding | Rak Min et al., Life Sci. 2005 Nov 4; 77(25): 3242-57. Epub 2005 Jun 22 |
| Cryptotanshinone | DNA binding | Zhou et al., Biochim Biophys Acta. 2006 Jan; 1760(1): 1-9. Epub 2005 Oct 3. |
| Cyanoguanidine CHS 828 | DNA binding | Johanson et al., Neuroendocrinology. 2005; 82(3-4): 171-6. Epub 2006 Feb 24 |
| Cytochalasin D | DNA binding | Kim et al., J Biol Chem. 2003 Oct 24; 278(43): 42448-56. Epub 2003 Aug 7 |
| DA-9201 (from black rice) | DNA binding | Lee et al., Arch Pharm Res. 2005 Dec; 28(12): 1350-7. |

TABLE 3-continued

MISCELLANEOUS INHIBITORS OF NF-κB

| Inhibitor Molecule | Effect or point of inhibition | References |
|---|---|---|
| Danshenshu | DNA binding | Jiang et al., Zhonghua Shao Shang Za Zhi. 2001 Feb; 17(1): 36-8 |
| (kB site) Decoy oligonucleotides | DNA binding | Kupatt et al., Gene Ther. 2002 Apr; 9(8): 518-26; Morishita et al., Nat Med. 1997 Aug; 3(8): 894-9 |
| Diamide | DNA binding | Toledano & Leonard, Proc Natl Acad Sci USA. 1991 May 15; 88(10): 4328-32 |
| Diarylheptanoid 7-(4'-hydroxy-3'-methoxyphenyl)-1-phenylhept-4-en-3-one | DNA binding | Yadav et al., J Pharmacol Exp Ther. 2003 Jun; 305(3): 925-31. Epub 2003 Mar 6 |
| alpha-difluoromethylornithine (polyamine depletion) | DNA binding | Facchini et al., J Cell Physiol. 2005 Sep; 204(3): 956-63 |
| DIM/I3C | DNA binding | Li et al., Front Biosci. 2005 Jan 1; 10: 236-43. Print 2005 Jan 1 |
| Diterpenoids from Isodon rubescens or Liverwort Jungermannia | DNA binding | Leung et al., Mol Pharmacol. 2005 Aug; 68(2): 286-97. Epub 2005 May 4; Kondoh et al., Planta Med. 2005 Nov; 71(11): 1005-9 |
| DTD (4,10-dichloropyrido[5,6: 4,5]thieno[3,2-d': 3,2-d]-1,2,3-ditriazine) | DNA binding | Rioja et al., Naunyn Schmiedebergs Arch Pharmacol. 2002 May; 365(5): 357-64. Epub 2002 Mar 19. |
| E1B (Adenovirus) | DNA binding | Limbourg et al., J Biol Chem. 1996 Aug 23; 271(34): 20392-8 |
| E3330 (quinone derivative) | DNA binding | Hiramoto et al., J Immunol. 1998 Jan 15; 160(2): 810-9; Kimura et al., Biochem Biophys Res Commun. 1997 Feb 24; 231(3): 557-60 |
| ent-kaurane diterpenoids (*Croton tonkinensis* leaves) | DNA binding | Giang et al., J Nat Prod. 2003 Sep; 66(9): 1217-20 |
| Epinastine hydrochloride | DNA binding | Kanai et al., Int Arch Allergy Immunol. 2006; 140(1): 43-52. Epub 2006 Mar 13 |
| Epoxyquinol A (fungal metabolite) | DNA binding | Li et al., Org Lett. 2002 Sep 19; 4(19): 3267-70 |
| Erythromycin | DNA binding/transactivation | Ren et al., J Orthop Res. 2004 Jan; 22(1): 21-9; Desaki et al., Antimicrob Agents Chemother. 2004 May; 48(5): 1581-5 |
| Evans Blue | DNA binding | Sharma et al., Bioorg Med Chem Lett. 2004 Dec 20; 14(24): 6123-7 |
| Evodiamine | DNA binding | Choi et al., Arch Pharm Res. 2006 Apr; 29(4): 293-7 |
| Fenoldopam | DNA binding | Aravindan et al., J Cardiothorac Vasc Anesth. 2006 Apr; 20(2): 179-86. Epub 2006 Jan 6 |
| Fexofenadine hydrochloride | DNA binding | Asano et al., Clin Exp Allergy. 2004 Dec; 34(12): 1890-8 |
| Fibrates | DNA binding | Hirano et al., Int Immunopharmacol. 2003 Feb; 3(2): 225-32 |
| Fish oil feeding | DNA binding | Fan et al., J Immunol. 2004 Nov 15; 173(10): 6151-60 |
| FK778 | DNA binding | Zeyda et al., Transplant Proc. 2005 May; 37(4): 1968-9 |
| FLN29 overexpression | DNA binding | Mashima et al., J Biol Chem. 2005 Dec 16; 280(50): 41289-97. Epub 2005 Oct 12 |
| FLICE-Like Inhibitory Protein (FLIP) | DNA binding | Bannerman et al., Am J Pathol. 2004 Oct; 165(4): 1423-31 |
| Flunixin meglumine | DNA binding | Bryant et al., Am J Vet Res. 2003 Feb; 64(2): 211-5 |
| Flurbiprofen | DNA binding | Fratelli et al., Antioxid Redox Signal. 2003 Apr; 5(2): 229-35 |
| *Fomes fomentarius* methanol extracts | DNA binding | Park et al., Biol Pharm Bull. 2004 Oct; 27(10): 1588-93 |
| Fucoidan | DNA binding | Haneji et al., Nutr Cancer. 2005; 52(2): 189-201 |
| G-120 (*Ulmus davidiana* | DNA binding; IkB | Son et al., Mol Cells. 2004 Oct |

TABLE 3-continued

MISCELLANEOUS INHIBITORS OF NF-κB

| Inhibitor Molecule | Effect or point of inhibition | References |
|---|---|---|
| Nakai glycoprotein) | increases | 31; 18(2): 163-70.; Lee et al., Food Chem Toxicol. 2005 Jun; 43(6): 961-8 |
| Gallic acid | DNA binding | Kim et al., Toxicol Sci. 2006 May; 91(1): 123-31. Epub 2005 Dec 1 |
| *Ganoderma lucidum* (fungal dried spores or fruting body) | DNA binding | Sliva et al., Biochem Biophys Res Commun. 2002 Nov 8; 298(4): 603-12. |
| Garcinol (fruit rind of *Garcinia* spp) | DNA binding | Hong et al., Carcinogenesis. 2006 Feb; 27(2): 278-86. Epub 2005 Aug 10 |
| Gax (homeobox protein) | DNA binding | Patel et al., Cancer Res. 2005 Feb 15; 65(4): 1414-24 |
| Geranylgeraniol | DNA binding | Espindola et al., Carcinogenesis. 2005 Jun; 26(6): 1091-9. Epub 2005 Feb 17 |
| Ghrelin | DNA binding | Li et al., Circulation. 2004 May 11; 109(18): 2221-6. Epub 2004 Apr 26 |
| Gigantol (*Cymbidium georingii*) | DNA binding | Won et al., Planta Med. 2006 Aug 21; [Epub ahead of print] |
| Ginkgolide B | DNA binding | Nie et al., Yao Xue Xue Bao. 2004 Jun; 39(6): 415-8. |
| Glycyrrhizin | DNA binding | Wang et al., Liver. 1998 Jun; 18(3): 180-5; Yuan et al., World J Gastroenterol. 2006 Jul 28; 12(28): 4578-81 |
| H4/N5 (IkB-like proteins of Microplitis demolitor bracovirus) | DNA binding | Thoetkiattikul et al., Proc Natl Acad Sci USA. 2005 Aug 9; 102(32): 11426-31. Epub 2005 Aug 1 |
| Halofuginone | DNA binding | Leiba et al., J Leukoc Biol. 2006 Aug; 80(2): 399-406. Epub 2006 Jun 12 |
| Heat (fever-like) | DNA binding | Salanova et al., FASEB J. 2005 May; 19(7): 816-8. Epub 2005 Mar 8 |
| Helenalin (sesquiterpene lactone) | DNA binding | Kim et al., Eur J Pharmacol. 2005 Mar 28; 511(2-3): 89-97 |
| Hematein (plant compound) | DNA binding | Oh et al., Atherosclerosis. 2001 Nov; 159(1): 17-26 |
| Herbal compound 861 | DNA binding | You et al., Zhonghua Gan Zang Bing Za Zhi. 2001 Apr; 9(2): 73-4 |
| Hesperetin | DNA binding | Kim et al., Aging Cell. 2006 Oct; 5(5): 401-11. Epub 2006 Aug25 |
| HIV-1 Resistance Factor | DNA binding | Lesner et al., J Immunol. 2005 Aug 15; 175(4): 2548-54 |
| Hydroxyethyl starch | DNA binding | Tian et al., Ann Clin Lab Sci. 2003 Fall; 33(4): 451-8; Feng et al., J Surg Res. 2006 Sep; 135(1): 129-36. Epub 2006 Apr 17 |
| Hydroxyethylpuerarin | DNA binding | Lou et al., Chin J Physiol. 2004 Dec 31; 47(4): 197-201 |
| Hypercapnic acidosis | DNA binding | Chonghaile et al., Curr Opin Crit Care. 2005 Feb; 11(1): 56-62 |
| Hypericin | DNA binding | Bork et al., Planta Med. 1999 May; 65(4): 297-300 |
| Hyperosmolarity | DNA binding | Lang et al., Am J Physiol Cell Physiol. 2003 Jan; 284(1): C200-8 |
| Hypothermia | DNA binding | Hassoun et al., J Surg Res. 2003 Nov; 115(1): 121-6 |
| Hydroquinone (HQ) | DNA binding | Pyatt et al., Toxicol Appl Pharmacol. 1998 Apr; 149(2): 178-84 |
| ICP27 (HSV-1) | DNA binding | Melchjorsen et al., J Gen Virol. 2006 May; 87(Pt 5): 1099-108 |
| Interleukin 4 (IL-4) | DNA binding | Manna & Aggarwal, J Biol Chem. 1998 Dec 11; 273(50): 33333-41 |
| IkB-like protein A238L (encoded by ASFV) | DNA binding | Powell et al., J Virol. 1996 Dec; 70(12): 8527-33; Revilla et al., J Biol Chem. 1998 Feb 27; 273(9): 5405-11 |
| Insulin-like growth factor | DNA binding | Williams et al., Cell Death Differ. |

TABLE 3-continued

MISCELLANEOUS INHIBITORS OF NF-κB

| Inhibitor Molecule | Effect or point of inhibition | References |
|---|---|---|
| binding protein-3 | | 2006 Apr 28; [Epub ahead of print] |
| JSH-21 (N1-Benzyl-4-methylbenzene-1,2-diamine) | DNA binding | Min et al., Arch Pharm Res. 2004 Oct; 27(10): 1053-9 |
| Kamebakaurin | DNA binding | Lee et al., J Biol Chem. 2002 May 24; 277(21): 18411-20. Epub 2002 Mar 4 |
| Kaposi's sarcoma-associated herpesvirus K1 protein | DNA binding | Lee et al., J Virol. 2002 Dec; 76(23): 12185-99 |
| Ketamine | DNA binding | Sun et al., Inflamm Res. 2004 Jul; 53(7): 304-8. Epub 2004 Jun 25 |
| KT-90 (morphine synthetic derivative) | DNA binding | Sueoka et al., Biochem Biophys Res Commun. 1998 Nov 27; 252(3): 566-70 |
| Linoleic acid | DNA binding | Zhao et al., Arch Anim Nutr. 2005 Dec; 59(6): 429-38 |
| *Lithospermi radix* | DNA binding | Chung et al., J Ethnopharmacol. 2005 Dec 1; 102(3): 412-7. Epub 2005 Jul 28 |
| Lovastatin | DNA binding | Sun & Fernandes, Cell Immunol. 2003 May; 223(1): 52-62 |
| Macrolide antibiotics | DNA binding | Nguyen et al., Curr Opin Pulm Med. 2002 Nov; 8(6): 521-8 |
| Mediterranean plant extracts | DNA binding | Stalinska et al., J Physiol Pharmacol. 2005 Mar; 56 Suppl 1: 157-69 |
| Mercaptopyrazine | DNA binding | Lim et al., Biochem Pharmacol. 2004 Aug 15; 68(4): 719-28 |
| 2-methoxyestradiol | DNA binding; Transactivation | Shimada et al., Mol Carcinog. 2004 Jan; 39(1): 1-9; Takada et al., Acta Med Okayama. 2004 Aug; 58(4): 181-7 |
| 6-(Methylsulfinyl)hexyl isothiocyanate (Wasabi) | DNA binding; Transactivation | Uto et al., Biochem Pharmacol. 2005 Dec 5; 70(12): 1772-84. Epub 2005 Oct 27 |
| Metals (chromium, cadmium, gold, lead, mercury, zinc, arsenic) | DNA binding | Shumilla et al., Arch Biochem Biophys. 1998 Jan 15; 349(2): 356-62; Yang et al., 1995; Zuscik et al., J Orthop Res. 2002 Jul; 20(4): 811-8 |
| Mevinolin, 5'-methylthioadenosine (MTA) | DNA binding | Law et al., Mol Cell Biol. 1992 Jan; 12(1): 103-11 |
| Monomethylfumarate | DNA binding | Litjens et al., Eur J Immunol. 2004 Feb; 34(2): 565-75 |
| Moxifloxacin | DNA binding | Werber et al., J Antimicrob Chemother. 2005 Mar; 55(3): 293-300. Epub 2005 Jan 19; Shalit et al., J Antimicrob Chemother. 2006 Feb; 57(2): 230-5. Epub 2005 Dec 13 |
| Myricetin | DNA binding | Kang et al., Arch Pharm Res. 2005 Mar; 28(3): 274-9. |
| NDPP1 (CARD protein) | DNA binding | Zhang & Fu, Int J Oncol. 2002 May; 20(5): 1035-40 |
| N-ethyl-maleimide (NEM) | DNA binding | Toledano & Leonard, Proc Natl Acad Sci USA. 1991 May 15; 88(10): 4328-32 |
| Naringen | DNA binding | Kanno et al., Life Sci. 2006 Jan 11; 78(7): 673-81. Epub 2005 Aug 31 |
| Nicorandil | DNA binding | Katamura et al., Shock. 2005 Aug; 24(2): 103-8 |
| Nicotine | DNA binding | Sugano et al., Biochem Biophys Res Commun. 1998 Nov 9; 252(1): 25-8 |
| Nitric oxide-donating aspirin | DNA binding | Kashfi & Rigas, Biochem Soc Trans. 2005 Aug; 33(Pt 4): 701-4. |
| Nilvadipine | DNA binding | Iwasaki et al., Clin Chim Acta. 2004 Dec; 350(1-2): 151-7 |
| Nitrosoglutathione | DNA binding | Kuo et al., J Trauma. 2004 Nov; 57(5): 1025-31; Khan et al., J Cereb Blood Flow Metab. 2005 Feb; 25(2): 177-92 |

TABLE 3-continued

MISCELLANEOUS INHIBITORS OF NF-κB

| Inhibitor Molecule | Effect or point of inhibition | References |
|---|---|---|
| NS1 (Influenza A) | DNA binding | Wang et al., J Virol. 2000 Dec; 74(24): 11566-73 |
| NS3/4A (Hepatitis C virus) | DNA binding | Karayiannis, J Hepatol. 2005 Oct; 43(4): 743-5 |
| Extracts of *Ochna macrocalyx* bark | DNA binding | Tang et al., Planta Med. 2003 Mar; 69(3): 247-53 |
| Leucine-rich effector proteins of *Salmonella* & *Shigella* (SspH1 and IpaH9.8) | DNA binding | Haraga & Miller, Infect Immun. 2003 Jul; 71(7): 4052-8 |
| Omega-3 fatty acids | DNA binding | Sethi, Redox Rep. 2002; 7(6): 369-78 |
| Oridonin (diterpenoid from *Rabdosia rubescens*) | DNA binding | Ikezoe et al., Mol Cancer Ther. 2005 Apr; 4(4): 578-86 |
| p8 | DNA binding | Vasseur et al., J Biol Chem. 2004 Feb 20; 279(8): 7199-207. Epub 2003 Dec 1 |
| 1,2,3,4,6-penta-O-galloyl-beta-D-glucose | DNA binding | Oh et al., Cancer Lett. 2001 Dec 10; 174(1): 17-24 |
| p202a (interferon inducible protein) | DNA binding by p65 and p50/p65; increases p50 | Ma et al., J Biol Chem. 2003 Jun 20; 278(25): 23008-19. Epub 2003 Apr 3 |
| p21 (recombinant) | DNA binding | Khanna et al., J Immunol. 2005 Jun 15; 174(12): 7610-7 |
| PC-SPES (8 herb mixture) | DNA binding | Ikezoe et al., Mol Pharmacol. 2003 Dec; 64(6): 1521-9; Ikezoe et alInt J Oncol. 2006 Aug; 29(2): 453-61 |
| Panepoxydone | DNA binding | Erkel et al., Biochem Biophys Res Commun. 1996 Sep 4; 226(1): 214-21 |
| Peptide nucleic acid-DNA decoys | DNA binding | Penolazzi et al., Int J Mol Med. 2004 Aug; 14(2): 145-52 |
| Pentoxifylline (1-(5'-oxohexyl) 3,7-dimetylxanthine, PTX) | DNA binding | Biswas et al., J Acquir Immune Defic Syndr. 1993 Jul; 6(7): 778-86; Wang et al., Immunity. 1997 Feb; 6(2): 165-74; Ji et al., Ann Clin Lab Sci. 2004 Autumn; 34(4): 427-36 |
| Peptide YY | DNA binding | Vona-Davis et al., J Am Coll Surg. 2004 Jul; 199(1): 87-95 |
| Pepluanone | DNA binding | Corea et al., J Med Chem. 2005 Nov 3; 48(22): 7055-62 |
| Perindopril | DNA binding | Li et al., World J Gastroenterol. 2005 Aug 21; 11(31): 4807-11 |
| 6(5H)-phenanthridinone and benzamide | DNA binding | Chiarugi, Br J Pharmacol. 2002 Nov; 137(6): 761-70 |
| *Phyllanthus amarus* extracts | DNA binding | Kiemer et al., J Hepatol. 2003 Mar; 38(3): 289-97 |
| PIAS1 (protein inhibitor of activatated STAT1) | RelA DNA binding | Liu et al., Mol Cell Biol. 2005 Feb; 25(3): 1113-23 |
| Pioglitazone (PPARgamma ligand) | DNA binding | Takagi et al., Redox Rep. 2002; 7(5): 283-9 |
| Pirfenidone | DNA binding | Tsuchiya et al., J Hepatol. 2004 Jan; 40(1): 94-101; Nakanishi et al., J Hepatol. 2004 Nov; 41(5): 730-6 |
| Polyozellin | DNA binding | Jin et al., Planta Med. 2006 Jul; 72(9): 857-9. Epub 2006 Jun 19. |
| Prenylbisabolane 3 (from *Croton eluteria* Bennett) | DNA binding | Campagnuoloe et al., Bioorg Med Chem. 2005 Jul 1; 13(13): 4238-42 |
| Pro-opiomelanocortin | DNA binding | Liu et al., Mol Pharmacol. 2006 Feb; 69(2): 440-51. Epub 2005 Nov 3 |
| Prostaglandin E2 | DNA binding and RelA nuclear translocation | Min et al., J Rheumatol. 2002 Jul; 29(7): 1366-76.; Gomez et al., J Immunol. 2005 Nov 15; 175(10): 6924-30 |
| Protein-bound polysaccharide (PSK) | DNA binding | Zhang et al., Oncogene. 2003 Apr 10; 22(14): 2088-96 |
| PYPAF1 protein | DNA binding | Jeru et al., Arthritis Rheum. 2006 Feb; 54(2): 508-14 |
| Pyridine N-oxide derivatives | DNA binding | Stevens et al., Biochem Pharmacol. 2006 Apr |

TABLE 3-continued

MISCELLANEOUS INHIBITORS OF NF-κB

| Inhibitor Molecule | Effect or point of inhibition | References |
|---|---|---|
| | | 14; 71(8): 1122-35. Epub 2006 Jan 24 |
| Pyrithione | DNA binding | Kim et al., Biochem Biophys Res Commun. 1999 Jun 16; 259(3): 505-9 |
| Pyrrole-imidazole polyamides | DNA binding | Wurtz et al., Biochemistry. 2002 Jun 18; 41(24): 7604-9. |
| Quinadril (ACE inhibitor) | DNA binding | Bustos et al., J Am Coll Cardiol. 1998 Dec; 32(7): 2057-64; Hernandez-Presa et al., Am J Pathol. 1998 Dec; 153(6): 1825-37 |
| Quinic acid | DNA binding | Akesson et al., Int Immunopharmacol. 2005 Jan; 5(1): 219-29 |
| Raf Kinase Inhibitor Protein (RKIP) | DNA binding | Keller, Anticancer Drugs. 2004 Aug; 15(7): 663-9 |
| Rapomycin | DNA binding | Dichtl et al., Atherosclerosis. 2006 Jun; 186(2): 321-30. Epub 2005 Sep 23. |
| Raloxifene | RelA DNA binding | Olivier et al., Mol Pharmacol. 2006 May; 69(5): 1615-23. Epub 2006 Feb 23 |
| Raxofelast | DNA binding | Altavilla et al., Free Radic Res. 2003 Apr; 37(4): 425-35 |
| Rebamipide | DNA binding | Hahm et al., Aliment Pharmacol Ther. 2003 Jul; 18 Suppl 1: 24-38 |
| *Rhus verniciflua* Stokes fruits 36 kDa glycoprotein | DNA binding | Ko et al., Toxicol In vitro. 2005 Apr; 19(3): 353-63. Epub 2004 Dec 24 |
| Ribavirin | DNA binding | Fiedler et al., J Virol. 1996 Dec; 70(12): 9079-82. |
| Rifamides | DNA binding | Pahlevan et al., J Antimicrob Chemother. 2002 Mar; 49(3): 531-4 |
| Ritonavir | DNA binding | Ikezoe et al., Cancer Res. 2004 Oct 15; 64(20): 7426-31 |
| Rosiglitazone | DNA binding | Gruden et al., J Am Soc Nephrol. 2005 Mar; 16(3): 688-96. Epub 2005 Jan 26 |
| Roxithromycin | DNA binding | Kim et al., Pharmacology. 2004 Sep; 72(1): 6-11 |
| Sanggenon C | DNA binding | Li et al., Acta Pharmacol Sin. 2002 Feb; 23(2): 138-42 |
| Santonin diacetoxy acetal derivative | DNA binding | Kim et al., J Biol Chem. 2006 May 12; 281(19): 13117-25. Epub 2006 Mar 22 |
| Secretory leukoprotease inhibitor (SLPI) | DNA binding | Jin et al., Cell. 1997 Feb 7; 88(3): 417-26: Greene et al., Infect Immun. 2004 Jun; 72(6): 3684-7; Taggart et al., J Exp Med. 2005 Dec 19; 202(12): 1659-68. Epub 2005 Dec 13. |
| Serotonin derivative (N-(p-coumaroyl) serotonin, SC) | DNA binding | Kawashima et al., J Interferon Cytokine Res. 1998 Jun; 18(6): 423-8 |
| Sesamin (from sesame oil) | DNA binding | Jeng et al., Immunol Lett. 2005 Feb 15; 97(1): 101-6. |
| Shen-Fu | DNA binding | Qian et al., Am J Chin Med. 2006; 34(4): 613-21. |
| Siah2 | DNA binding | Habelhah et al., EMBO J. 2002 Nov 1; 21(21): 5756-65 |
| Silibinin | DNA binding | Schumann et al., J Hepatol. 2003 Sep; 39(3): 333-40. |
| Simvastatin | DNA binding | Li et al., J Pharmacol Exp Ther. 2002 Aug; 302(2): 601-5.; Kalyanasundaram et al., J Vasc Surg. 2006 Jan; 43(1): 117-24. |
| Sinomenine | DNA binding | Chen et al., Zhongguo Zhong Yao Za Zhi. 2004 Sep; 29(9): 900-3. |
| SIRT1 Deacetylase overexpression | DNA binding | Chen et al., J Biol Chem. 2005 Dec 2; 280(48): 40364-74. Epub 2005 Sep 23. |
| Siva-1 | DNA binding | Gudi et al., Oncogene. 2006 Jun 8; 25(24): 3458-62. Epub 2006 Feb 20. |

TABLE 3-continued

| MISCELLANEOUS INHIBITORS OF NF-κB | | |
|---|---|---|
| Inhibitor Molecule | Effect or point of inhibition | References |
| SM-7368 (small molecule) | DNA binding | Lee et al., Biochem Biophys Res Commun. 2005 Oct 21; 336(2): 716-22. |
| *Solana nigrum L.* 150 kDa glycoprotein | DNA binding | Heo et al., Toxicol In vitro. 2004 Dec; 18(6): 755-63.; Lee & Lim, Toxicol In vitro. 2006 Oct; 20(7): 1088-97. Epub 2006 Mar 9. |
| Sulfasalazine | DNA binding | Egan & Sandborn, Gastroenterology. 1998 Nov; 115(5): 1295-6. |
| SUN C8079 | DNA binding | Matsumori et al., Eur J Heart Fail. 2004 Mar 1; 6(2): 137-44. |
| Surfactant protein A | DNA binding | Alcorn & Wright, J Biol Chem. 2004 Jul 16; 279(29): 30871-9. Epub 2004 May 3. |
| Sword brake fern extract | DNA binding | Wu et al., J Ethnopharmacol. 2005 Apr 8; 98(1-2): 73-81. |
| T-614 (a methanesulfoanilide anti-arthritis inhibitor) | DNA binding | Aikawa et al., Inflamm Res. 2002 Apr; 51(4): 188-94 |
| *Tanacetum larvatum* extract | DNA binding | Petrovic et al., J Ethnopharmacol. 2003 Jul; 87(1): 109-13 |
| Tansinones (*Salvia miltiorrhiza* Bunge, Labiatae roots) | DNA binding | Choi et al., Arch Pharm Res. 2004 Dec; 27(12): 1233-7. |
| Taurine + niacine | DNA binding | Giri, Adv Exp Med Biol. 2003; 526: 381-94.; Kim & Kim, Biochem Pharmacol. 2005 Nov 1; 70(9): 1352-60. |
| Tetramethylpyrazine | DNA binding | Cheng et al., Planta Med. 2006 Aug; 72(10): 888-93. Epub 2006 Aug 10. |
| Tobacoo smoke | DNA binding | Zhong et al., Am J Respir Crit Care Med. 2006 Aug 15; 174(4): 428-36. Epub 2006 May 18 |
| Tom1 (target of Myb-1) overexpression | DNA binding | Yamakami & Yokosawa, Biol Pharm Bull. 2004 Apr; 27(4): 564-6. |
| Thiazolidinedione MCC-555 | DNA binding | Kurebayashi et al., Atherosclerosis. 2005 Sep; 182(1): 71-7. Epub 2005 Mar 4. |
| Transdominant p50 | DNA binding | Logeat et al., EMBO J. 1991 Jul; 10(7): 1827-32. |
| Trichostatin A | RelA DNA binding | Hu & Colburn, 2005 |
| Triclosan plus cetylpyridinium chloride | DNA binding | Kim et al., J Periodontol. 2005 Oct; 76(10): 1735-42. |
| Triptolide (PG490, extract of Chinese herb) | DNA binding | Qiu et al., J Biol Chem. 1999 May 7; 274(19): 13443-50; Kim et al., Eur J Pharmacol. 2004 Jun 21; 494(1): 1-9.; Yinjun et al., Leuk Res. 2005 Jan; 29(1): 99-105. |
| Tyrphostin AG-126 | DNA binding | Moore et al., 2003 |
| Ursolic acid | DNA binding | Hsu et al., Life Sci. 2004 Sep 24; 75(19): 2303-16. |
| Uteroglobin | DNA binding | Mandal et al., J Exp Med. 2004 May 17; 199(10): 1317-30. |
| V, C proteins (Sendai virus) | DNA binding | Komatsu et al., Virology. 2004 Jul 20; 325(1): 137-48. |
| Vascular endothelial growth factor (VEGF) | DNA binding | Oyama et al., J Immunol. 1998 Feb 1; 160(3): 1224-32.; Gabrilovich et al., Blood. 1998 Dec 1; 92(11): 4150-66 |
| Verapamil | DNA binding | Li et al., Inflamm Res. 2006 Mar; 55(3): 108-13. |
| Withaferin A | DNA binding | Mohan et al., Angiogenesis. 2004; 7(2): 115-22. |
| Wogonin (5,7-dihydroxy-8-methoxyflavone) | DNA binding | Lee et al., FASEB J. 2003 Oct; 17(13): 1943-4. Epub 2003 Aug 1; Piao et al., Arch Pharm Res. 2004 Sep; 27(9): 930-6. |

TABLE 3-continued

| MISCELLANEOUS INHIBITORS OF NF-κB | | |
|---|---|---|
| Inhibitor Molecule | Effect or point of inhibition | References |
| Xanthohumol (a hops prenylflavonoid) | DNA binding | Colgate et al., Cancer Lett. 2006 Mar 22; [Epub ahead of print] |
| Xylitol | DNA binding | Han et al., Clin Diagn Lab Immunol. 2005 Nov; 12(11): 1285-91 |
| Yan-gan-wan | DNA binding | Yang et al., Hepatol Res. 2005 Aug; 32(4): 202-212. Epub 2005 Aug 16 |
| Yin-Chen-Hao | DNA binding | Cai et al., J Pharm Pharmacol. 2006 May; 58(5): 677-84. |
| *Yucca schidigera* extract | DNA binding | Marzocco et al., Life Sci. 2004 Aug 6; 75(12): 1491-501.; Cheeke et al., J Inflamm (Lond). 2006 Mar 29; 3: 6. |
| Overexpressed ZIP1 | DNA binding | Khadeer et al., Bone. 2005 Sep; 37(3): 296-304. |
| Plant compound A (a phenyl aziridine precursor) | DNA binding and transactivation | De Bosscher et al., Proc Natl Acad Sci USA. 2005 Nov 1; 102(44): 15827-32. Epub 2005 Oct 21. |
| 8-acetoxy-5-Hydroxyumbelliprenin (from Asafetida) | Transactivation | Appendino et al., J Nat Prod. 2006 Jul; 69(7): 1101-4. |
| AMP-activated protein kinase | Transactivation | Cacicedo et al., Biochem Biophys Res Commun. 2004 Nov 26; 324(4): 1204-9. |
| APC0576 | Transactivation | Yuzawa et al., Transplantation. 2003 May 15; 75(9): 1463-8. |
| *Artemisia sylvatica* sesquiterpene lactones | Transactivation (reporter assays) | Jin et al., Phytochemistry. 2004 Aug; 65(15): 2247-53. |
| Artemisolide | Transactivation | Reddy et al., Arch Pharm Res. 2006 Jul; 29(7): 591-7. |
| BSASM (plant extract mixture) | Transactivation (reporter assays) | Lee et al., J Ethnopharmacol. 2005 Jan 4; 96(1-2): 127-9. |
| Bifodobacteria | Transactivation | Riedel et al., World J Gastroenterol. 2006 Jun 21; 12(23): 3729-35. |
| *Bupleurum fruticosum* phenylpropanoids | Transactivation | Bremner et al., Planta Med. 2004 Oct; 70(10): 914-8. |
| Blueberry and berry mix (Optiberry) | Transactivation | Atalay et al., FEBS Lett. 2003 Jun 5; 544(1-3): 252-7 |
| BZLF1(EBV protein) | Transactivation | Morrison et al., Virology. 2004 Oct 25; 328(2): 219-32 |
| Chromene derivatives | Transactivation | Cheng et al., Bioorg Med Chem Lett. 2003 Nov 3; 13(21): 3647-50. |
| D609 (phosphatidylcholine-phospholipase C inhibitor) | Transactivation | Bergmann et al., J Biol Chem. 1998 Mar 20; 273(12): 6607-10 |
| Dehydroevodiamine | Transactivation | Noh et al., Life Sci. 2006 Jul 10; 79(7): 695-701. Epub 2006 Mar 6 |
| 4'-demethyl-6-methoxypodophyllotoxin (lignan of *Linum tauricum* Willd. ssp. *tauricum*) | Transactivation | Vailev et al., Neoplasma. 2005; 52(5): 425-9. |
| Ethyl 2-[(3-methyl-2,5-dioxo(3-pyrrolinyl)) amino]-4-(trifluoromethyl) pyrimidine-5-carboxylate | Transactivation | Palanki et al., Bioorg Med Chem Lett. 2002 Sep 16; 12(18): 2573-7 |
| Cycloprodigiosin hycrochloride | Transactivation | Kamata et al., FEBS Lett. 2001 Oct 19; 507(1): 74-80. |
| Dimethylfumarate (DMF) | Nuclear translocation | Loewe et al., J Immunol. 2002 May 1; 168(9): 4781-7. |
| E1A (Adenovirus) | Transactivation | Cook et al., Proc Natl Acad Sci USA. 2002 Jul 23; 99(15): 9966-71. Epub 2002 Jul 15. |
| Eckol/Dieckol (seaweed *E stolonifera*) | Transactivation | Joe et al., Biol Pharm Bull. 2006 Aug; 29(8): 1735-9. |
| *Fructus Benincasae Recens* extract | Transactivation | Kwon et al., Immunopharmacol Immunotoxicol. 2003 Nov; 25(4): 615-25. |
| Glucocorticoids (dexametasone, prednisone, methylprednisolone) | Transactivation and increases IkBa levels | Auphan et al., Science. 1995 Oct 13; 270(5234): 286-90; Brostjan et al., J Biol Chem. 1996 Aug 9; 271(32): 19612-6; Ray & Prefontaine, Proc Natl Acad Sci USA. 1994 Jan 18; 91(2): 752-6; |

TABLE 3-continued

MISCELLANEOUS INHIBITORS OF NF-κB

| Inhibitor Molecule | Effect or point of inhibition | References |
|---|---|---|
| | | Scheinman et al., Mol Cell Biol. 1995 Feb; 15(2): 943-53 |
| Gypenoside XLIX (from *Gynostemma pentaphyllum*) | Transactivation (PPAR-alpha-dependent) | Huang et al., J Biomed Sci. 2006 Jul; 13(4): 535-48. Epub 2006 Mar 10. |
| Histidine | Transactivation | Son et al., FEBS Lett. 2005 Aug 29; 579(21): 4671-7. |
| HIV-1 protease inhibitors (nelfinavir, ritonavir, or saquinavir) | Transactivation | Equils et al., Antimicrob Agents Chemother. 2004 Oct; 48(10): 3905-11. |
| Kwei Ling Ko (Tortoise shell-Rhizome jelly) | Transactivation | Yip et al., Phytomedicine. 2005 Nov; 12(10): 748-59. |
| *Ligusticum chuanxiong* Hort root | Transactivation | Liu et al., Planta Med. 2005 Sep; 71(9): 808-13. |
| Low gravity | Transactivation | Boonyaratanakornkit et al., FASEB J. 2005 Dec; 19(14): 2020-2. Epub 2005 Oct 6 |
| Nobiletin | Transactivation | Murakami et al., J Nutr. 2005 Dec; 135(12 Suppl): 2987S-2992S |
| NRF (NF-κB repression factor) | Transactivation | Jianfeng et al., Mol Cells. 2003 Dec 31; 16(3): 397-401 |
| Paeonol (from Mountain Cortx) | Transactivation | Ishiguro et al., Toxicol Appl Pharmacol. 2006 Jul 14; [Epub ahead of print] |
| Phenethylisothiocyanate | Transactivation | Gerhauser et al., Mutat Res. 2003 Feb-Mar; 523-524: 163-72. |
| 4-phenylcoumarins (from *Marila pluricostata*) | Transactivation | Bedoya et al., Bioorg Med Chem Lett. 2005 Oct 15; 15(20): 4447-50. |
| Phomol | Transactivation | Weber et al., J Antibiot (Tokyo). 2004 Sep; 57(9): 559-63. |
| PIAS3 | Transactivation | Jang et al., J Biol Chem. 2004 Jun 4; 279(23): 24873-80. Epub 2004 Mar 26. |
| Pranlukast | Transactivation | Ichiyama et al., Clin Exp Allergy. 2003 Jun; 33(6): 802-7; Ishinaga et al., Pharmacology. 2005 Feb; 73(2): 89-96. Epub 2004 Oct 5. |
| Psychosine | Transactivation | Haq et al., J Neurochem. 2003 Sep; 86(6): 1428-40. |
| Quinazolines | Transactivation | Tobe et al., Bioorg Med Chem. 2003 Sep 1; 11(18): 3869-78. |
| Resveratrol | RelA nuclear localization and transactivation | Manna et al., J Immunol. 2000 Jun 15; 164(12): 6509-19; Pendurthi et al., Thromb Haemost. 2002 Jan; 87(1): 155-62. |
| RO31-8220 (PKC inhibitor) | Transactivation | Bergmann et al., J Biol Chem. 1998 Mar 20; 273(12): 6607-10. |
| Saucerneol D and saucerneol E | Transactivation | Hwang et al., Phytochemistry. 2003 Oct; 64(3): 765-71 |
| SB203580 (p38 MAPK inhibitor) | Transactivation | Bergmann et al., J Biol Chem. 1998 Mar 20; 273(12): 6607-10. |
| SH protein (Mumps Virus) | Transactivation | Wilson et al., J Virol. 2006 Feb; 80(4): 1700-9. |
| Tranilast [N-(3,4-dimethoxycinnamoyl)anthranilic acid] | Transactivation | Spiecker et al., Mol Pharmacol. 2002 Oct; 62(4): 856-63. |
| 3,4,5-trimethoxy-4'-fluorochalcone | Transactivation | Rojas et al., Naunyn Schmiedebergs Arch Pharmacol. 2003 Sep; 368(3): 225-33. Epub 2003 Aug 2. |
| *Uncaria tomentosum* plant extract | Transactivation | Akesson et al., Int Immunopharmacol. 2003 Dec; 3(13-14): 1889-900. |
| LY294,002 | Transactivation | Sizemore et al., Mol Cell Biol. 1999 Jul; 19(7): 4798-805. |
| Mesalamine | RelA phosphorylation & transactivation | Egan et al., J Biol Chem. 1999 Sep 10; 274(37): 26448-53. |
| Mesuol | RelA phosphorylation & transactivation | Marquez et al., Antiviral Res. 2005 Jun; 66(2-3): 137-45. Epub 2005 Apr 20 |
| PTX-B (pertussis toxin binding protein) | RelA phosphorylation and transactivation | Iordanskiy et al., Virology. 2002 Oct 10; 302(1): 195-206 |
| 9-aminoacridine (9AA) derivatives (including the | RelA phosphorylation and transactivation | Gurova et al., Proc Natl Acad Sci USA. 2005 Nov |

TABLE 3-continued

MISCELLANEOUS INHIBITORS OF NF-κB

| Inhibitor Molecule | Effect or point of inhibition | References |
|---|---|---|
| antimalaria drug quinacrine) | | 29; 102(48): 17448-53. Epub 2005 Nov 15. |
| Adenosine and cyclic AMP | Transactivation | Majumdar & Aggarwal, Oncogene. 2003 Feb 27; 22(8): 1206-18.; Minguet et al., Eur J Immunol. 2005 Jan; 35(1): 31-41 |
| 17-allylamino-17-demethoxygeldanamycin | Transactivation | Rakitina et al., Cancer Res. 2003 Dec 15; 63(24): 8600-5 |
| 6-aminoquinazoline derivatives | Transactivation | Tobe et al., Bioorg Med Chem. 2003 Sep 1; 11(18): 3869-78 |
| Luteolin | p65 Transactivation | Kim et al., Biochem Pharmacol. 2003 Sep 15; 66(6): 955-63 |
| Manassantins A and B | p65 Transactivation | Lee et al., Biochem Pharmacol. 2003 Nov 15; 66(10): 1925-33.; Son et al., Mol Cells. 2005 Aug 31; 20(1): 105-11. |
| Paromyxovirus SH gene products | Transactivation | Wilson et al., J Virol. 2006 Feb; 80(4): 1700-9 |
| Qingkailing and Shuanghuanglian (Chinese medicinal preparations) | Transactivation | Chen et al., Life Sci. 2002 May 3; 70(24): 2897-913. |
| *Smilax bockii* warb extract (flavenoids) | Transactivation | Xu et al., Arch Pharm Res. 2005 Apr; 28(4): 395-9. |
| Tetracyclic A | Transactivation (ROS production) | Turbyville et al., Mol Cancer Ther. 2005 Oct; 4(10): 1569-76. |
| Tetrathiomolybdate | Transactivation | Pan et al., Cancer Res. 2002 Sep 1; 62(17): 4854-9 |
| Trilinolein | Transactivation | Liu et al., Eur J Pharmacol. 2004 Jan 19; 484(1): 1-8. |
| Troglitazone | Transactivation | Ruan et al., J Biol Chem. 2003 Jul 25; 278(30): 28181-92. Epub 2003 May 5. |
| Valerenic acid/acetylvalerenolic acid | Transactivation | Jacobo-Herrera et al., Phytother Res. 2006 Oct; 20(10): 917-9. |
| *Witheringia solanacea* leaf extracts | Transactivation | Jacobo-Herrera et al., J Nat Prod. 2006 Mar; 69(3): 328-31 |
| Wortmannin (fungal metabolite) | Transactivation | Reddy et al., J Biol Chem. 1997 Nov 14; 272(46): 29167-73.; Manna & Aggarwal, FEBS Lett. 2000 May 4; 473(1): 113-8. |
| Xia-Bai-San | Transactivation | Yeh et al., Int Immunopharmacol. 2006 Sep; 6(9): 1506-14. Epub 2006 Jun 2. |
| Alpha-zearalenol | Transactivation | Li et al., Biomed Environ Sci. 2005 Oct; 18(5): 314-20. |
| Antithrombin | RelA-p300 interaction | Uchiba et al., Thromb Haemost. 2004 Dec; 92(6): 1420-7. |
| Extract of the stem bark of *Mangifera indica* L. | NF-κB mRNA expression | Leiro et al., Int Immunopharmacol. 2004 Aug; 4(8): 991-1003 |
| Rifampicin | Glucocorticoid receptor modulation | Yerramesetti et al., J Clin Immunol. 2002 Jan; 22(1): 37-47. |
| Mangiferin | Inhibition of RelA and RelB expression | Leiro et al., Int Immunopharmacol. 2004 Jun; 4(6): 763-78 |

In specific embodiments, the NF-κB pathway inhibitor is an inhibitor of IκB phosphorylation, such as BAY 11-7082 and BAY-11-7085 (BioMol, Plymouth Meeting, Pa.).

Desirably, the inhibitor of NF-κB function is non-toxic to the host with minimal or negligible side effects. Suitably, the inhibitor of NF-κB blocks the alternate NF-κB pathway, or both the classical and the alternate NF-κB pathways as described for example in paragraph [0008] (Martin E et al., Immunity 2003, supra).

2.3 Antigens

Various target antigens exist, which are associated with unwanted or deleterious immune responses. In accordance with the present invention, an antigen that corresponds to at least a portion of a target antigen is used in combination with an NF-κB inhibitor as described, for example, in Section 2.2 to produce particles as described, for example in Section 2.1, for inducing a tolerogenic immune response to the target antigen. Illustrative target antigens include alloantigens and self antigens or peptide fragments thereof, which are presented in the context of MHC, as well as soluble proteins and fragments of insoluble complexes, particulate antigens, e.g., bacteria or parasites, and allergens. Thus, exemplary antigens which are useful in the practice of the present invention include, but are not limited to, self antigens that are targets of autoimmune responses, allergens and transplantation antigens. Examples of self antigens include, but are not restricted to, lupus autoantigen, Smith, Ro, La, U1-RNP, fibrillin associated with scleroderma; nuclear antigens, histones, glycoprotein gp70 and ribosomal proteins associated with systemic lupus erythematosus; pyruvate dehydrogenase dehydrolipoamide acetyltransferase (PCD-E2) associated with primary biliary cirrhosis; hair follicle antigens associated with alopecia greata; human tropomyosin isoform 5 (hTM5) associated with ulcerative colitis; proinsulin, insulin, IA2 and GAD65 associated with insulin-dependent diabetes; collagen type II, human cartilage gp 39 (HCgp39) and gp130-RAPS, dnaJp1, citrullinated proteins and peptides e.g., citrullinated type II collagen, vimentin or fibrinogen associated with rheumatoid arthritis; myelin basic protein, proteolipid protein (PLP) and myelin oligodendrocyte glycoprotein (MOG) associated with multiple sclerosis; thyroid stimulating factor receptor (TSH-R) associated with Graves' disease; acetylcholine receptor (AchR) associated with Myasthenia Gravis; gliadin associated with celiac disease; histones, PLP, glucose-6-phosphate isomerase, thyroglobulin, various tRNA synthetases, proteinase-3, myeloperoxidase etc. Examples of allergens include, but are not limited to, Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite dermatophagoides, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruit fly, sheep blow fly, screw worm fly, grain weevil, silkworm, honeybee, non-biting midge larvae, bee moth larvae, mealworm, cockroach and larvae of Tenibrio molitor beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives. Transplantation antigens can be derived from donor cells or tissues from e.g., heart, lung, liver, pancreas, kidney, neural graft components, or from donor antigen-presenting cells bearing MHC loaded with self antigen in the absence of exogenous antigen.

The antigen(s) may be isolated from a natural source or may be prepared by recombinant techniques as is known in the art. For example, peptide antigens can be eluted from the MHC and other presenting molecules of antigen-presenting cells obtained from a cell population or tissue for which a modified immune response is desired, e.g., an allogeneic tissue or cell population in transplantation medicine. The eluted peptides can be purified using standard protein purification techniques known in the art (Rawson et al., 2000, Cancer Res 60(16), 4493-4498). If desired, the purified peptides can be sequenced and synthetic versions of the peptides produced using standard protein synthesis techniques as for example described below. Alternatively, crude antigen preparations can be produced by isolating a sample of a cell population or tissue for which a modified immune response is desired, and either lysing the sample or subjecting the sample to conditions that will lead to the formation of apoptotic cells (e.g., irradiation with ultra violet or with gamma rays, viral infection, cytokines or by depriving cells of nutrients in the cell culture medium, incubation with hydrogen peroxide, or with drugs such as dexamethasone, ceramide chemotherapeutics and anti-hormonal agents such as Lupron or Tamoxifen). The lysate or the apoptotic cells can then be used as a source of crude antigen for contact with the antigen-presenting cells.

When the antigen is known, it may be conveniently prepared in recombinant form using standard protocols as for example described in: Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6. Typically, an antigen may be prepared by a procedure including the steps of (a) providing an expression vector from which the target antigen or analogue or mimetic thereof is expressible; (b) introducing the vector into a suitable host cell; (c) culturing the host cell to express recombinant polypeptide from the vector; and (d) isolating the recombinant polypeptide.

Alternatively, the antigen can be synthesised using solution synthesis or solid phase synthesis as described, for example, by Atherton and Sheppard (Solid Phase Peptide Synthesis: A Practical Approach, IRL Press at Oxford University Press, Oxford, England, 1989) or by Roberge et al. (1995, Science 269: 202).

In some embodiments, the antigen is in the form of one or more peptides. Usually, such peptides are at least 6, 7, 8, 9, 10, 11, 12, 13, 14, 15, 20, 25, 30 amino acid residues in length and suitably no more than about 500, 200, 100, 80, 60, 50, 40 amino acid residues in length. In some embodiments in which two or more peptides are used, the peptides can be in the form of a plurality of contiguous overlapping peptides whose sequences span at least a portion of a target antigen. Suitably, the peptide sequences are derived from at least about 30, 40, 50, 60, 70, 80, 90, 91, 92, 93, 94, 95, 96, 97, 98, 99% of the sequence corresponding to the target antigen. In some embodiments, each peptide of the plurality of contiguous overlapping peptide fragments can be 30-90 amino acids in length, e.g., 30, 35, 40, 45, 50, 55, 60, 65, 70, 73, 75, 80, 81, 85, 86 and 90 amino acids in length. In various embodiments, the amino acid sequences of contiguous overlapping peptide fragments in the plurality overlap by about 10 to about 15 amino acids, e.g., 10, 11, 12, 13, 14 and 15 amino acids. Exemplary methods for producing such peptide antigens are described, for example, by Astori et al. (2000 J. Immunol. 165, 3497-3505; and references cited therein) and in U.S. Pat. Appl. Pub. No. 2004/0241178. The antigen may be suitably modified, for example, by lipid modification to modify its physico-chemical properties.

2.4 Ancillary Components

In some embodiments the particulate compositions further comprises one or more immunosuppressive cytokines, which are suitably selected from IL-1 receptor antagonist, IL-1RII, VEGF, IL-4, IL-10 (human or viral), IL-13, TGF-β and FLT3 ligand or their functional, recombinant or chemical equivalents or homologues thereof.

3. Pharmaceutical Formulations

In accordance with the present invention, one or more NF-κB pathway inhibitors described in Section 2.2 and one or more antigens described in Section 2.3 are used to produce particles as described, for example in Section 2.1, for modifying an immune response, especially for inducing a tolerogenic response including the suppression of a future or existing immune response, to one or more target antigens. These compositions are useful, therefore, for treating or preventing an undesirable immune response including, for example, transplant rejection, graft versus host disease, allergies, parasitic diseases, inflammatory diseases and autoimmune diseases. Examples of transplant rejection, which can be treated or prevented in accordance with the present invention, include rejections associated with transplantation of bone marrow and of organs such as heart, liver, pancreas, kidney, lung, eye, skin etc. Examples of allergies include seasonal respiratory allergies; allergy to aeroallergens such as hayfever; allergy treatable by reducing serum IgE and eosinophilia; asthma; eczema; animal allergies, food allergies; latex allergies; dermatitis; or allergies treatable by allergic desensitisation. Autoimmune diseases that can be treated or prevented by the present invention include, for example, psoriasis, systemic lupus erythematosus, myasthenia gravis, stiff-man syndrome, thyroiditis, Sydenham chorea, rheumatoid arthritis, diabetes and multiple sclerosis. Examples of inflammatory disease include Crohn's disease, chronic inflammatory eye diseases, chronic inflammatory lung diseases and chronic inflammatory liver diseases, autoimmune haemolytic anaemia, idiopathic leucopoenia, ulcerative colitis, dermatomyositis, scleroderma, mixed connective tissue disease, irritable bowel syndrome, systemic lupus erythromatosus (SLE), multiple sclerosis, myasthenia gravis, Guillan-Barre syndrome (antiphospholipid syndrome), primary myxoedema, thyrotoxicosis, pernicious anaemia, autoimmune atrophic gastris, Addison's disease, insulin-dependent diabetes mellitus (IDDM), Goodpasture's syndrome, Behcet's syndrome, Sjogren's syndrome, rheumatoid arthritis, sympathetic ophthalmia, Hashimoto's disease/hypothyroiditis, celiac disease/ dermatitis herpetiformis, and demyelinating disease primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock. Other unwanted immune reactions that can also be treated or prevented by the present invention include antibodies to recombinant therapeutic agents such as anti-factor VIII antibodies in hemophilia or anti-insulin antibodies in diabetes.

The above compositions are, therefore, useful for treating or preventing an unwanted or deleterious immune response in a patient, which comprises administering to the patient a pharmaceutical composition comprising an NF-κB pathway inhibitor and an antigen that corresponds to a target antigen, in particulate form, in amounts that are effective to reduce or suppress the immune response to the target antigen. The pharmaceutical composition may comprise a pharmaceutically acceptable carrier or diluent. In some embodiments, the compositions are administered to individuals having the unwanted or deleterious immune response. In other embodiments, the compositions are administered to at-risk individuals who are autoantibody positive and/or HLA haplotype identified at risk e.g., Type 1 diabetes first degree relatives with at least one and desirably two or more autoantibodies positive (see, e.g., Scofield, R. H., 2004. Lancet 363, 1544; Berglin et al., 2004, Arthritis Res Ther 6, R30336; Harrison et al., 2004, Diabetes Care 27, 2348), or individuals at risk of rheumatoid arthritis, with one or two HLA susceptibility genes and positive anti-CCP antibodies (Klarskog et al. 2006, Arthritis Rheum. 54: 38) (Rantapaa-Dahlqvist S et al. 2003, Arthritis Rheum. 48:2741).

Pharmaceutical compositions suitable for use in the present invention include compositions wherein the bioactive agents (i.e., the NF-κB pathway inhibitor and the antigen) are contained in an effective amount to achieve their intended purpose. The dose of active compounds administered to a patient should be sufficient to achieve a beneficial response in the patient over time such as a reduction in at least one symptom associated with the unwanted or deleterious immune response, which is suitably associated with a condition selected from an allergy, an autoimmune disease and a transplant rejection. The quantity or dose frequency of the pharmaceutically active compounds(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the treatment or prophylaxis of the unwanted or deleterious immune response, the practitioner may evaluate inflammation, pro-inflammatory cytokine levels, lymphocyte proliferation, cytolytic T lymphocyte activity and regulatory T lymphocyte function. In any event, those of skill in the art may readily determine suitable dosages of the antagonist and antigen.

Accordingly, the particles are administered to a subject to be treated in a manner compatible with the dosage formulation, and in an amount that will be prophylactically and/or therapeutically effective. The amount of the composition to be delivered, generally in the range of from 0.01 μg/kg to 100 μg/kg of bioactive molecule (e.g., antigen or inhibitor) per dose, depends on the subject to be treated. In some embodiments, and dependent on the intended mode of administration, the NF-κB pathway inhibitor-containing compositions will generally contain about 0.1% to 90%, about 0.5% to 50%, or about 1% to about 25%, by weight of the inhibitor, the remainder being suitable pharmaceutical carriers and/or diluents etc and the antigen. The dosage of the inhibitor can depend on a variety of factors, such as mode of administration, the species of the affected subject, age and/or individual condition. In other embodiments, and dependent on the intended mode of administration, the antigen-containing compositions will generally contain about 0.1% to 90%, about 0.5% to 50%, or about 1% to about 25%, by weight of antigen, the remainder being suitable pharmaceutical carriers and/or diluents etc and NF-κB pathway inhibitor.

Depending on the specific condition being treated, the particles may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, transcutaneous, intradermal, intramedullary delivery (e.g., injection), as well as intrathecal, direct intraventricular, intravenous, intraperitoneal, intranasal, or intraocular delivery (e.g., injection). For injection, the particles of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The compositions of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the particles of the present invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the particles in water-soluble form. Additionally, suspensions of the particles may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, the suspension may also contain suitable stabilisers or agents that increase the solubility of the compounds to allow for the preparation of highly concentrated solutions.

Pharmaceutical preparations for oral use can be obtained by combining the particles with solid excipients and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, eg. by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterise different combinations of particle doses.

Pharmaceuticals which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The particles of the invention may be administered over a period of hours, days, weeks, or months, depending on several factors, including the severity of the neuropathic condition being treated, whether a recurrence of the condition is considered likely, etc. The administration may be constant, e.g., constant infusion over a period of hours, days, weeks, months, etc. Alternatively, the administration may be intermittent, e.g., particles may be administered once a day over a period of days, once an hour over a period of hours, or any other such schedule as deemed suitable.

The compositions of the present invention may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 µm, suitably less than 10 µm.

In some embodiments, the particles are administered for active uptake by cells, for example by phagocytosis, as described for example in U.S. Pat. No. 5,783,567 (Pangaea). In some embodiments, phagocytosis by these cells may be improved by maintaining a particle size typically below about 20 µm, and preferably below about 11 µm.

In specific embodiments, the particles are delivered directly into the bloodstream (i.e., by intravenous or intraarterial injection or infusion) if uptake by the phagocytic cells of the reticuloendothelial system (RES), including liver and spleen, is desired. Alternatively, one can target, via subcutaneous injection, take-up by the phagocytic cells of the draining lymph nodes. The particles can also be introduced intradermally (i.e., to the APCs of the skin, such as dendritic cells and Langerhans cells) for example using ballistic or microneedle delivery. Illustrative particle-mediated delivery techniques include explosive, electric or gaseous discharge delivery to propel carrier particles toward target cells as described, for example, in U.S. Pat. Nos. 4,945,050, 5,120,657, 5,149,655 and 5,630,796. Non-limiting examples of microneedle delivery are disclosed in International Publication Nos. WO 2005/069736 and WO 2005/072630 and U.S. Pat. Nos. 6,503,231 and 5,457,041.

Another useful route of delivery (particularly for DNAs encoding tolerance-inducing polypeptides) is via the gastrointestinal tract, e.g., orally. Alternatively, the particles can be introduced into organs such as the lung (e.g., by inhalation of powdered microparticles or of a nebulized or aerosolized solution containing the microparticles), where the particles are picked up by the alveolar macrophages, or may be administered intranasally or buccally. Once a phagocytic cell phagocytoses the particle, the NF-κB pathway inhibitor and antigen are released into the interior of the cell.

Accordingly, the present invention provides for the induction of tolerance or anergy to an antigen that is associated with an unwanted or deleterious immune response including without limitation autoimmune diseases, allergies and transplantation associated diseases. In some embodiments, therefore, the present invention provides for the induction of tolerance to an autoantigen for the treatment of autoimmune diseases by administering the antigen for which tolerance is desired along with an NF-κB inhibitor, wherein the antigen and NF-κB inhibitor are in particulate form. In an illustrative example of this type, autoantibodies directed against the acetylcholine receptor (AChR) are observed in patients with Myasthenia gravis, and, accordingly, AchR-antigen or antigen-expressing vectors in particulate form may be used in the invention to be delivered in conjunction with an NF-κB inhibitor in particulate form to treat and/or prevent Myasthenia gravis.

In still other embodiments, an individual who is a candidate for a transplant from a non-identical twin may suffer from rejection of the engrafted cells, tissues or organs, as the engrafted antigens are foreign to the recipient. Prior tolerance of the recipient individual to the intended graft abrogates or reduces later rejection. Reduction or elimination of chronic anti-rejection therapies may be achieved by administering concurrently to the recipient of the transplant one or more transplantation antigens in particulate form and an NF-κB inhibitor in particulate form.

In further embodiments, sensitization of an individual to an industrial pollutant or chemical, such as may be encountered on-the-job, presents a hazard of an immune response. Prior tolerance of the individual's immune system to the chemical may be desirable to prevent the later occupational development of an immune response. In these cases, it is generally desirable to administer concurrently to the individual a particulate form of the chemical reacted with the individual's endogenous proteins, together with an NF-κB inhibitor in particulate form.

Notably, even in diseases where the pathogenic autoantigen is unknown, bystander suppression may be induced using particulate forms of antigens present in the anatomical vicinity of the pathogenesis and an NF-κB inhibitor in particulate form. For example, autoantibodies to collagen are observed in rheumatoid arthritis and, accordingly, collagen or a collagen-encoding gene (see e.g. Choy (2000) Curr Opin Investig Drugs 1: 58-62) in particulate form may be utilized, together with an NF-κB inhibitor in particulate form in order to treat rheumatoid arthritis. Furthermore, tolerance to beta cell autoantigens may be utilized to prevent development of type 1 diabetes (see e.g. Bach and Chatenoud (2001) Ann Rev Immunol 19: 131-161) in a similar manner.

As another example, auto-antibodies directed against myelin oligodendrocyte glycoprotein (MOG) are observed in autoimmune encephalomyelitis and in many other CNS diseases as well as multiple sclerosis (see e.g. Iglesias et al. (2001) Glia 36: 22-34). Accordingly, co-delivery of a particulate form of MOG antigen or MOG antigen-expressing constructs with an NF-κB inhibitor in particulate form allows for treatment or prevention of multiple sclerosis as well as related autoimmune disorders of the central nervous system.

In order that the invention may be readily understood and put into practical effect, particular preferred embodiments will now be described by way of the following non-limiting examples.

EXAMPLES

Example 1

Antigen-Specific Suppression of Arthritis by Liposomes

Materials and Methods

Reagents

Fluorescein isothiocyanate (FITC), ovalbumin (OVA), methylated bovine serum albumin (mBSA) and were purchased from Sigma-Aldrich (Missouri, USA). Penicillin, streptomycin, L-glutamine, sodium pyruvate and 2-mercaptoethanol were purchased from Gibco® Invitrogen (California, USA). Complete Freund's Adjuvant (CFA) was obtained from Sigma-Aldrich (Missouri, USA). carboxyfluorescein diacetate succinimidyl ester (CFSE) was obtained from Molecular Probes (Oregon, USA). KJ1-26 antibody labelled with phycoerythrin (PE) was purchased from BD Pharmingen (California, USA). Anti-mouse-MHC II-FITC was purchased from Biolegend (California, USA). CD4 epitope of OVA (sequence 323-339) was obtained from Auspep (Victoria, Australia). All other reagents were of at least analytical grade.

Mice

Male C57/B16 and BALB/c mice were obtained from ARC and the OVA-specific TCR-transgenic strain, DO11.10 on the BALB/c background, was bred at University of Queensland. CFSE was from Molecular Probes (Eugene, Oreg.).

Conjugation of Fluorescein Isothiocyanate to Ovalbumin

Fifty mg of FITC was dissolved in 50 mL of carbonate buffer (pH 9.5, 0.22 mol/L) with 500 mg of OVA. The mixture was gently stirred and allowed to react in the dark at room temperature for 1 hour and subsequently kept at 4° C. overnight. Buffer salts and unbound FITC were removed from the conjugated protein by repeated dilution with water and ultrafiltration using a 10,000 molecular weight cut-off membrane (Millipore, Mass., USA) using a 400 mL ultrafiltration cell (Millipore, Mass., USA) pressurized with nitrogen gas to 200 kPa. The resulting FITC-ovalbumin (FITC-OVA) solution was frozen in an acetone-dry ice bath and lyophilized (Alpha 2-4 LD Freeze-drier, Martin Christ, Germany). Degree of conjugation was confirmed by centrifugation a sample of the lyophilised protein solution at 10,000 g for 20 minutes (EBA 12R centrifuge, Hettich Zentrifugen, Germany), through a 10,000 molecular weight cut off filter unit (Millipore, Mass., USA). Unbound FITC contributed less than 1% of total fluorescence in all cases. The conjugated protein was then stored and protected from light at 4° C. until required.

Liposome Preparation and Composition

Liposomes were prepared by conventional thin film method. Briefly, 100 mg egg phosphatidylcholine (EPC) and 0.35, 1.42 and 1.75 mg of Bay 11-7082, Quecertin or Curcumin respectively (or other quantities of inhibitor as required) were dissolved together in 10 mL of chloroform/ethanol solvent mixture (9:1 v/v) in a 250 mL round bottomed flask. The lipid solution was dried in a rotary evaporator under vacuum at 40° C. for 30 minutes to produce a thin lipid film. Lipid films were then stored under vacuum for a further 30 minutes to remove any residual solvent (Alpha 2-4 LD Freeze-drier, Martin Christ, Germany). Two mL of ovalbumin or mBSA at a concentration of 10 mg/ml in pH 7.4 HEPES buffer was then added and shaken by hand at room temperature to produce multilamellar vesicles. In some experiments, 2 mL of FITC-OVA at the concentration of 10 mg/mL were used. Liposome dispersions were allowed to stand at room temperature for a further 2 hours to complete the swelling process. Crude liposome suspensions were then frozen in an acetone dry-ice bath and thawed in a water bath at a temperature of 40° C. This freeze-thawing cycle was repeated 5 times to increase entrapment of protein.

For liposome loaded with ovalbumin, liposomes were reduced in size and lamellarity by 5 cycles of high-pressure extrusion through 800 nm polycarbonate membrane (Nucleopore Corp., CA, USA) and then 5 cycles through 400 nm polycarbonate membrane (Nucleopore Corp., CA, USA) using a 10 mL extruder (Lipex Extruder, Northern Lipids Inc, Vancouver, Canada) pressurized with nitrogen gas. For liposome loaded with mBSA, liposomes were extruded 10 times through a 400 nm membrane. Liposomes were left at room temperature for at least 2 hours in order to allow the annealing process to complete before being further used. Fluorescent labelling of liposomes was accomplished when required by adding 15 μL of an ethanolic solution of DiI at a concentration of 10 mg/ml to the final liposome preparation.

Removal of non-entrapped NF-κB inhibitors and antigens was effected by diluting liposomes in HEPES buffer followed by ultracentrifugation using an Optima™ TLX Tabletop ultracentrifuge (Beckman Coulter, USA) at 100,000 g (4° C., 45 min). Liposome pellets were re-dispersed in HEPES buffer prior to use. Entrapment efficiency of protein following this process was typically at least 20%, approximately 60% for Bay and greater than 80% for both Quecertin and Curcumin. Empty, NF-κB inhibitor or protein only liposomes were prepared as above, by omitting the relevant bioactive/s.

Protein antigens as described above can be substituted by peptide epitopes of antigenic proteins and these can be efficiently encapsulated within liposomes by lipid modification and hydration of freeze dried monophase systems as described by Liang et al. (2005, Int. J. Pharm. 301: 247-254).

Detection of Liposomes by Flow Cytometry and Immunofluorescence Microscopy

Twenty four hours after subcutaneous (s.c.), intravenous (i.v.) or intraperitoneal (i.p.) injection of DiI-labelled liposomes or no injection, spleen and draining lymph nodes were removed. One portion was frozen in OCT and subjected to immunofluorescence microscopy. Cells were purified from the remaining portion, stained with FITC-conjugated anti-I-A mAb, and analyzed by flow cytometry.

Bone Marrow Derived DC Preparation and Administration

Bone marrow cells were collected and suspended from murine long bones, passed through nylon mesh, and mononuclear cells separated by ficoll gradient centrifugation. Macrophages, class II+ cells and lymphocytes were immunodepleted using appropriate mAb followed by magnetic beads (MACS, Miltenyi Biotec, CA). BM cells were incubated for 6-8d in XCe11620 (CSL) medium supplemented with 10 ng/ml each GM-CSF and IL-4 (Peprotech, Rocky Hill, N.J.), with fresh medium was applied on alternate days. DC preparations routinely contained 80-90% CD11c+ cells. Bay-treated DC were cultured continuously in the presence of approximately 5 μM BAY 11-7082 (Bay, BioMol, Plymouth Meeting, Pa.) then exposed to 100 μM mBSA (Sigma) for 24 h before washing and suspension in normal saline. 5×105 Bay-treated DC were administered s.c. in the tail base 6 days after the induction of arthritis. Liposomes were suspended at 10 mg/mL, and 100 μL were administered either i.v. or s.c. to the tail base 6 days after the induction of arthritis. In some experiments either 50 μg soluble mBSA or 10 μg Bay solution, were injected s.c. in the tail base, adjacent to the site of liposome injection.

Characterization of Liposome Formulations Entrapping NF-κB Inhibitor and Model Antigen Entrapment Efficiency of NF-κB Inhibitor and Antigen in Liposomes (% EE)

Following removal of non-entrapped NF-κB inhibitor and antigen, the amount of NF-κB inhibitor and antigen entrapped in liposome could be quantified by assay method. The entrapment efficiency was expressed as:

$$\% EE = \frac{\text{Amount of drug in liposome}}{\text{Amount of drug initially added}} \times 100$$

Assay of NF-κB Inhibitor

For Bay 11-7082, liposomes were lysed by addition of ethanol at 20-fold dilution which was required for protein precipitation. The resulting solution was then kept at −20° C. After 30 minutes, the sample was centrifuged at maximum speed at 4° C. for 10 minutes (EBA 12R centrifuge, Hettich Zentrifugen, Germany) to remove precipitated protein. The concentration of Bay 11-7082 in the resulting supernatant was then assayed and calculated based on the established calibration (with consideration to the dilutions performed) (data not shown). For quercetin and curcumin, liposomes were lysed by addition of 5% w/v triton X-100 in PBS pH 6.5. The concentration of either quercetin or curcumin in the resulting solution was then assayed and calculated based on the established calibration curves (with consideration to the dilutions performed). Validation of assay showed that there was no significant interference from antigen on the developed quantitative assay of each NF-κB inhibitor.

Assay of Model Antigen

The quantity of model antigen entrapped in liposomes was determined by a standard bicinchoninic acid (BCA) protein assay with slight modification. Briefly, liposomes loaded with OVA or mBSA were lysed using ethanol or iso-propanol at 20-fold dilution, respectively, and then stored at −20° C. After 30 minutes, the sample was centrifuged at maximum speed at 4° C. for 10 minutes (EBA 12R centrifuge, Hettich Zentrifugen, Germany). The supernatant containing lipid and NF-κB inhibitor was discarded. The protein pellet was then placed in an Alpha 2-4 LD Freeze-drier (Alpha 2-4 LD Freeze-drier, Martin Christ, Germany) to remove remaining solvent. One hundred μL of 2.5% w/v sodium dodecyl sulfate (SDS) solution (for OVA) or water (for mBSA) was added to redissolve the protein pellet. SDS was required for aiding to re-dissolve OVA pellet. The resulting protein solution was mixed with 2 mL of BCA solution (Pierce Biotechnology Inc., USA) and incubated at 37° C. for 30 minutes. After incubation, the absorbance of the solution was measured using a Cary 50 UV-VIS spectrophotometer (Varian, Calif., USA) at a wavelength of 562 nm. The concentration of OVA and mBSA was calculated on the basis of calibration curves established using a series of known concentrations of either OVA or mBSA solution ranging from 0.25 mg/mL to 2 mg/mL.

Particle Size and Zeta Potential

The size distribution and zeta potential of the extruded and washed liposomal dispersions were determined, following dilution in HEPES buffer pH 7.4, by photon correlation spectroscopy and micro-electrophoresis, respectively (Zetasizer 3000, Malvern, UK).

Stability of Liposomal Formulation

Liposomal samples prepared were kept at 4° C. (usual short-term storage conditions) and particle size and the polydispersity index were monitored over 7 days by correlation spectroscopy.

Retention of Antigen Entrapped in Liposomes Containing Different NF-κB Inhibitors The retention of antigen within liposomes was investigated using FITC-OVA. Liposome formulations were prepared. The liposome dispersion was diluted with HEPES pH 7.4 buffer or HEPES pH 7.4 buffer containing 10% FBS to obtain a dilution factor of 1:20. The diluted dispersions were stirred and incubated at 37° C. At defined time points, aliquots were removed from the diluted dispersion and ultracentrifuged (100,000 g, 45 minutes, 4° C., Optima™ TLX Tabletop ultracentrifuge, Beckman Coulter, USA) to separate released FITC-OVA from liposomes. 0.6 mL of 5% w/v triton X-100 in PBS pH 6.5 was added to 0.4 mL of supernatant containing release FITC-OVA following dilution with 3 mL HEPES buffer pH 7.4. The resulting solution was then analysed the fluorescent intensity by fluorescence spectrophotometry at excitation wavelength of 492 nm and emission wavelength of 518 nm (RF-1501 spectrofluorophotometer, Shimadzu, Japan) and compared to fluorescent intensity of total FITC-OVA entrapped in liposomes treated with the same condition but without separation of release from entrapped FITC-OVA.

NF-κB Activity in Mice Treated with Liposomes Containing NF-κB Inhibitor

NF-κB inhibitor loaded liposomes were prepared. Groups of C57BL/6 mice (n=3) were injected subcutaneously at the tail base with a 50 µL of liposome formulations containing NF-κB inhibitors including Bay 11-7082, quercetin and curcumin with final concentrations of 0.5, 2 and 2 mM, respectively. Control mice received sc injections of empty liposomes. After 24 hours, ILN were removed and pressed through a 70 µm cell strainer. Cells were washed and resuspended at a concentration of $2\times10^6$ cells/mL in RPMI+10% FCS supplemented with 100 µg/mL penicillin, 100 µg/mL streptomycin, 10 mM sodium pyruvate, 20 mM HEPES, 2 mM L-glutamine and 50 µM 2-mercaptoethanol (complete RPMI). Cells were then incubated with or without 100 ng/mL of LPS. After 24 hours incubation, nuclear extracts were prepared as previously described (Pettit, A. R., C. Quinn, K. P. MacDonald, L. L. Cavanagh, G. Thomas, W. Townsend, M. Handel, and R. Thomas. 1997. Nuclear localization of RelB is associated with effective antigen-presenting cell function. *J Immunol* 159:3681-3691).

Briefly, cells ($2\times10^6$ cells) were harvested, washed and resuspended in 400 µL of ice cold 10 mM HEPES buffer pH 7.9 containing 10 mM potassium chloride (KCl), 0.1 mM ethylenediaminetetraacetic acid (EDTA), 0.1 mM ethylene glycol-bis(-aminoethylether)-N,N,N,N-tetra-acetic acid (EGTA), 0.1 mM dithiothreitol (DTT), 0.5 mM phenylmethylsulfonyl fluoride (PMSF) and 1% v/v protease inhibitor cocktail. The cells were incubated on ice for 15 minutes, followed by the addition of 25 µL of cold 10% Nonidet P-40 (Sigma, USA) and 10 seconds of vigorous stirring using a bench top vortex. The homogenate was centrifuged at 10,000 rpm for 30 seconds at 4° C. (Mikro 20, Hettich Zentrifugen, Germany) and the supernatant containing the cytoplasmic fraction was discarded. The nuclear pellet was then resuspended in 50 µL of ice cold buffer 20 mM HEPES pH 7.9 containing 0.4 M Sodium Chloride (NaCl), 1 mM EDTA, 1 mM EGTA, 0.1 mM DTT, 1 mM PMSF and 1% v/v protease inhibitor cocktail. The tube was vigorously rocked at 4° C. for 15 minutes followed by centrifugation at 12,000 rpm for 5 minutes at 4° C. (Mikro 20, Hettich Zentrifugen, Germany). The supernatant was collected as the nuclear fraction and stored at −70° C. until required. The protease inhibitor cocktail was a mixture of aprotinin, leupeptin and pepstatin-A supplied as a tablet (Complete Mini Tablet™, Roche Diagnostics, Switzerland) and prepared following the manufacturer's instructions. P50/NF-κB DNA binding was detected by ELISA using BD Transfactor Family Colorimetric kit for NF-κB (BD Biosciences) following the manufacturer's instructions. The resulting color was detected by a Multiskan plate reader (Labsystems, Illinois, USA).

Induction of Specific Tolerance Following In Vivo Administration of Liposomes Co-Entrapping NF-κB Inhibitor and Antigen: Ova-Specific T-Cell Model

Stimulation of OVA-Specific T-Cells by Liposomes Co-Entrapping OVA and NF-κB Inhibitor Spleen and ILN were harvested from naïve DO11.10 mice (OVA-specific TCR transgenic mice) and pressed through a 70 µm cell strainer. Cells were suspended at $1\times10^7$ cell/mL in warm PBS and mixed with an equal volume of 10 µM CFSE and incubated for 10 minutes at 37° C. The cells in CFSE solution were washed twice with ice cold RPMI+10% FCS by centrifuging at 450×g for 5 minutes at 4° C., and resuspended at a density of $2.5\times10^7$ cells/mL. Two hundred µL of cell suspension was intravenously injected into recipient BALB/c mice via the tail vein. After 24 hours, 50 µL of liposome formulations entrapping OVA and NF-κB inhibitor were subcutaneously injected at the tail base (formulations reported in Table 1). Empty liposomes, OVA-liposomes and OVA in CFA were used as controls. ILN were removed 72 hours post-injection, and processed into single cell suspensions. Cells were then stained with KJ1-26-PE antibody (specific for DO11.10 cells) for flow cytometry analysis.

Effect of NF-κB Inhibitor Co-Entrapped with OVA in Liposomes on Ova-Specific T-Cell Activity after Restimulation with OVA Peptide Antigen Spleen and ILN were harvested from naïve DO11.10 mice and pressed through a 70 µm cell strainer. Two hundred µL cell suspension at a density of $2.5\times10^7$ cells/mL was injected intravenously into recipient BALB/c mice via the tail vein. Twenty four hours after transfer, mice were primed with OVA in CFA by subcutaneous injection at the tail base. 7 days later, mice were injected subcutaneously at the tail base with 50 µL of liposome formulations co-entrapping OVA and NF-κB inhibitor (Table 4). ILN were removed 7 days post-injection and processed into a single cell suspension. T-cells were enriched by passing through a nylon wool column and then washed by centrifuging at 450×g for 5 minutes. T-cells were resuspended at a concentration of $2\times10^6$ cells/mL in complete RPMI. One hundred µL of T-cell suspension was cultured in round-bottom 96-well microtiter plates (Techno Plastic Products, Switzerland) and restimulated with CD11c+ cells purified from spleens of naïve mice by positive immuno-selection using CD11c+ microbeads and LS columns (Miltenyi, Germany). OVA peptide at a concentration ranging from 0-2000 ng/mL was added to the wells containing T-cells to obtain a final concentration of peptide from 0-1000 ng/mL and a final volume of 200 µL. Plates were incubated at 37° C. and 5% $CO_2$ for 3 days. T-cell proliferation was measured by the uptake of [$^3$H]-thymidine which was added for the final 18 hours of culture. The cells were then collected onto glass fiber filter paper with an automated 96-well harvester (Packard Instruments, Connecticut, USA). [$^3$H]-thymidine incorporation was determined by liquid scintillation counting using a TopCount NXT scintillation counter (Packard Instruments, Connecticut, USA). Proliferation was reported as the mean cpm±SEM of triplicate wells.

TABLE 4

Composition of liposomes co-entrapping OVA and NF-κB inhibitors

| Compositions in liposomal formulations* | OVA liposome | Bay11-7082 OVA liposome | Quercetin OVA liposome | Curcumin OVA liposome |
|---|---|---|---|---|
| OVA (mg/mL) | 2 | 2 | 2 | 2 |
| NF-kB inhibitor (mM) | — | 0.5 | 2 | 2 |

*The average final concentrations of OVA and NF-kB in liposomes prepared from 100 mg of EPC after free drugs were removed and re-dispersed in 2 mL of HEPES pH 7.4.

Induction of Specific Tolerance Following In Vivo Administration of Liposomes Co-Entrapping NF-κB Inhibitor and Antigen: Antigen-Induced Arthritis (AIA) Model Twenty one days before arthritis induction, C57BL/6 mice were immunized in each axilla by intradermal injection with 100 μg mBSA in 50 μL saline, emulsified in 50 μL CFA. Simultaneously, 400 ng of pertussis toxin in 200 μL saline was intraperitoneally injected. 7 days later, a booster dose of 100 μg mBSA in 50 μL saline, emulsified in 50 μL CFA was subcutaneously injected at the tail base. At day 21, arthritis was induced by intra-articular injection of 60 μg mBSA in 10 μL saline into the right knee joint cavity, while the left knee joint was treated with 10 μL of saline as control. At day 27, each group of mice (n=10) was subcutaneously injected with 50 μL of various liposomal formulations (Table 5) at the tail base. Untreated mice and mice receiving 50 μL empty liposomes were used as controls.

TABLE 5

Composition of liposomes co-entrapping mBSA and NF-κB inhibitors

| Compositions in liposomal formulations* | mBSA liposome | Bay 11-7082 mBSA liposome | Quercetin mBSA liposome | Curcumin mBSA liposome |
|---|---|---|---|---|
| mBSA (mg/mL) | 2.5 | 2.5 | 2.5 | 2.5 |
| NF-kB inhibitor (mM) | — | 0.5 | 2 | 2 |

*The average final concentrations of mBSA and NF-kB in liposomes prepared from 100 mg of EPC after free drugs were removed and re-dispersed in 2 mL of HEPES pH 7.4.

In separate experiments, groups of mice were injected subcutaneously with 50 μL of curcumin-OVA liposomes (composition specified in Table 1), 50 μl, of curcumin-mBSA liposomes (composition specified in Table 5) or 50 μL of curcumin encapsulated within liposomes (no antigen) administered concurrently with 50 μL of mBSA solution at concentration of 2.5 mg/mL. From the day of arthritis induction, knee joint swelling was measured in each mouse every 3-4 days for up to 13 days with a vernier calliper (Mitutoyo corp, Japan), and expressed as a percentage based on the difference between the diameter of the right and the left knee joint, where the maximum difference between two knees in each mouse was equal to 100%. At day 33, mice were killed by cervical dislocation, and skin on the knees was removed. The severity of knee joint swelling was compared between knees injected with antigen and saline, and expressed as a clinical score. The score was rated from 1 to 5 where 1=no change between saline and antigen knees, 2=slight discoloration of joint, 3=discoloration of joint and mild lateral swelling and discoloration, 4=discoloration of joint and moderate lateral swelling and discoloration and 5=severe discoloration of joint to the point where the ligament is no longer visible and severe lateral swelling and discoloration.

Statistical Analysis

Significant differences between groups of data reported in this chapter were determined by either unpaired Student's t-test (where two comparisons were being made) or Analysis of Variance (where multiple comparisons were being made). A value of p of less than 0.05 was considered to indicate significant difference.

Results

Liposomes are Taken Up by MHC Class II+ Phagocytic Cells in Lymphoid Organs and Present Antigen to Specific T Cells The distribution of liposome in vivo is influenced by route of administration, particle size and lipid composition (Oussoren, C., and G. Storm. 2001. Liposomes to target the lymphatics by subcutaneous administration. *Adv Drug Deliv Rev* 50:143-156). To date, intravenous (i.v.) and subcutaneous (s.c.) injections have been extensively investigated as routes of administration of liposomes for vaccination. Liposomes administered by i.v. injection are delivered to various organs systemically, and typically rapidly accumulate in liver and spleen, while those injected subcutaneously are retained at the injection site and are captured by infiltrating antigen presenting cells which then migrate to regional draining lymph nodes, or are able to access resident lymph node APCs directly through the skin draining lymphatics (Oussoren, C., M. Velinova, G. Scherphof, J. J. van der Want, N. van Rooijen, and G. Storm. 1998. Lymphatic uptake and biodistribution of liposomes after subcutaneous injection. IV. Fate of liposomes in regional lymph nodes. *Biochim Biophys Acta* 1370:259-272; Metselaar, J. M., M. H. Wauben, J. P. Wagenaar-Hilbers, O. C. Boerman, and G. Storm. 2003. Complete remission of experimental arthritis by joint targeting of glucocorticoids with long-circulating liposomes. *Arthritis Rheum* 48:2059-2066; Allen, T. M., C. B. Hansen, and L. S. Guo. 1993. Subcutaneous administration of liposomes: a comparison with the intravenous and intraperitoneal routes of injection. *Biochim Biophys Acta* 1150:9-16). Coating the liposome surface with a hydrophilic polymer such as polyethyleneglycol has been found to avoid the rapid uptake of liposomes by the liver, prolonging the circulation time of liposomes in the blood stream (Torchilin, V. P. 2005. Recent advances with liposomes as pharmaceutical carriers. *Nat Rev Drug Discov* 4:145-160).

For the purpose of tolerance, liposomes are required to deliver their encapsulated components to phagocytic cells, including DC precursors and some DCs that are resident in or migrate to lymphoid organs such as spleen and lymph node. Fluorescently labeled EPC liposomes extruded through 400 nm filter membranes were administered to mice either by intravenous injection via the tail vein, or subcutaneous injection at the tail base to investigate whether the liposomes can target APCs in lymphoid organs. In view of its many advantages, including strong fluorescence, low toxicity, easy labelling process, integration with high stability in liposomal membrane and resistance to transfer between cell membranes, DiI was used as a fluorescent label (Claassen, E. 1992. Post-formation fluorescent labelling of liposomal membranes. In vivo detection, localisation and kinetics. *J Immunol Methods* 147:231-240). To assess for uptake of DiI-labelled liposomes by APC, 24 hours post-injection, spleen (for i.v. injection) and regional lymph nodes (for s.c. and i.p. injection) were collected, processed into cell suspensions and then stained for MHC-class II, which is expressed by APCs, including B cells, DCs and macrophages, or CD11c, which is expressed by DCs.

DiI liposomes are visualised, after uptake by MHC class II+ and CD11c+ cells in draining lymph nodes or spleen (FIG. 1, A-C). Liposomes are taken up by CD11b+ and F480+ macrophages and CD11c+ DCs in the spleen after i.v. or s.c. injection (FIG. 1, D-H)).

NF-κB Activity in Mice Treated with Liposomes Containing NF-κB Inhibitor

Figure 2:
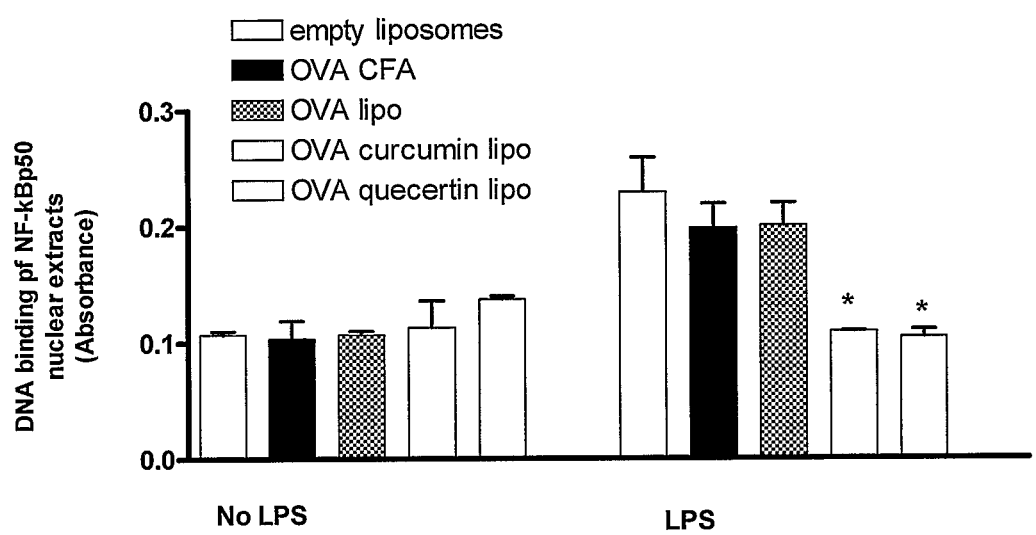
FIG. 2 is a graphical representation showing that liposomes containing NF-κB inhibitors block the NF-κB response in draining lymph node cells. C57BL/6 mice were injected i.v. with 50 μL of liposomal formulations. After 24 hours, the spleen was removed and processed into cell suspensions. Cells were incubated in medium with or without 100 ng/mL LPS for 24 hours. Nuclear extracts were obtained and analyzed for p50 NF-κB DNA binding by ELISA. Each column represents the level of p50/NF-kB DNA binding from a pool of three mice. Results represent mean and SD as error bar from three experiments in mice treated with liposomes. *$p<0.05$, comparing LPS response after curcumin and quecertin liposomes with response after empty liposome administration.

To examine the effect of NF-κB inhibitor entrapped in liposomes on the activation of NF-κB, groups of C57BL/6 mice (n=~3) were injected sc or iv with OVA-liposome entrapping various NF-κB inhibitors. 24 hours post-injection, cells in spleen were isolated and then cultured for a further 24 hr with or without LPS. Nuclear NF-κB activity was determined by DNA binding of p50/NF-κB in nuclear extracts to consensus oligonucleotides using ELISA (FIG. 2). Nuclear p50 was tested in this assay, as p50 is highly expressed by APC, and therefore should be a sensitive method to determine NF-κB activity even though MHC-II$^+$ cells were not purified from draining lymph nodes.

Cells obtained from mice treated with liposomes displayed low levels of p50 DNA binding in the absence of LPS treatment ex vivo. As expected, LPS increased the p50 DNA binding in cells from mice receiving empty liposomes. In contrast, after LPS treatment, cells obtained from mice injected with liposomes entrapping either quercetin or curcumin had no p50 DNA binding increase in response to LPS. These results indicate that liposomes entrapping either quercetin or curcumin can block the NF-κB activity of APCs after delivery in vivo. The induction of specific tolerance in vivo by liposome co-entrapping NF-κB inhibitor and antigen: OVA-specific T-cell model

Stimulation of OVA-Specific T-Cells by Liposomes Co-Entrapping OVA and NF-κB Inhibitor To determine whether OVA entrapped within liposomal formulations can be presented by APCs to OVA-specific T-cells in vivo, liposomes co-entrapping OVA and NF-κB inhibitors but without DiI were injected subcutaneously into the tail base of naïve Balb/c mice to which DO11.10 OVA specific TCR transgenic T-cells labelled with CFSE had been adoptively transferred. 72 hours after liposome injection, cells from ILN removed from recipient mice were stained with PE labelled KJ126 antibody specific for DO11.10 T-cells. CFSE is a cytoplasmic stain that is shared equally between daughter cells when the parent cell divides. T-cell proliferation can therefore be determined by measuring the decrease in CFSE fluorescence intensity of OVA-specific T-cells using flow cytometry.

Figure 3:
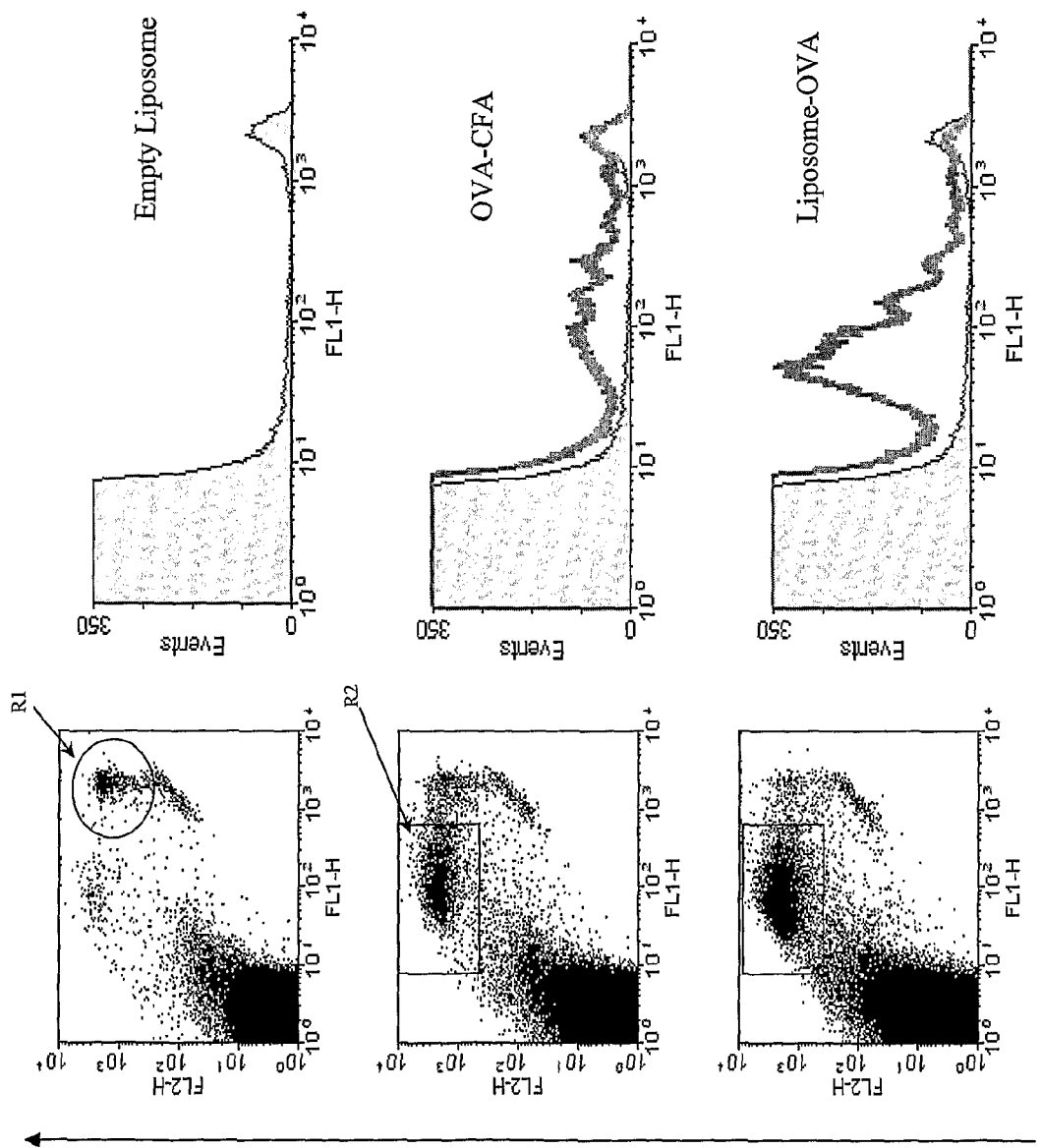
FIG. 3 is a graphical representation showing that liposomes combined with antigen stimulate a specific T cell response in draining LN whether or not NF-κB inhibitor is included in the particle. BALB/c mice were treated with 504 of various liposomal formulations 1 day after adoptive transfer of OVA-specific T-cells labelled with CSFE. After 72 hours, inguinal lymph nodes were removed and processed into cell suspensions. Cells were then stained with PE labelled KJ1-26 antibody, which recognises the OVA-specific TCR, and analysed by flow cytometry. Dot plots with circular gate (R1) represent parent cells while dot plots with rectangular gate (R2) represent daughter cells. The histograms demonstrates the decrease in CFSE fluorescence intensity (from right to left) indicating the T-cells responses from mice treated with various OVA formulations (line histogram) compared to mice treated with empty liposomes (fill histogram). Results are representative of two separate experiments.

In mice injected with empty liposomes, T-cell proliferation, as measured by CFSE dilution from the parent population, was negligible. In contrast, in mice injected with either OVA-CFA or OVA-liposomes, T-cells divided vigorously over 72 hours (FIG. 3). These results clearly demonstrate that OVA entrapped within liposomes can be delivered to APCs in vivo, where it is processed and presented to T-cells, resulting in antigen-specific proliferation. There was no difference in the T-cell proliferative response in draining lymph nodes whether mice were injected with liposomes entrapping OVA and liposomes co-entrapping OVA and NF-κB inhibitor (FIG. 3).

The expansion of T-cells in vivo upon administration of liposome entrapping OVA and NF-κB inhibitor was similar to previous studies using DEC-205-conjugated antigen to target DCs in the steady state in vivo. The immature DCs internalizing DEC-205 antigen could first induce the proliferation of T-cells but within a week, most of T-cells were unable to respond to the antigen previously supplied in the conjugate (Mahnke, K., Y. Qian, J. Knop, and A. H. Enk. 2003. Induction of CD4+/CD25+ regulatory T cells by targeting of antigens to immature dendritic cells. *Blood* 101:4862-4869; Hawiger, D., K. Inaba, Y. Dorsett, M. Guo, K. Mahnke, M. Rivera, J. V. Rauetch, R. M. Steinman, and M. C. Nussenzweig. 2001. Dendritic cells induce peripheral T cell unresponsiveness under steady state conditions in vivo. *J Exp Med* 194:769-780). The delayed suppression of T-cell response was due to the induction of peripheral regulatory T cells by immature DCs, leading to antigen-specific tolerance by a sequence of anergy and deletion of effector T-cells (Mahnke, K., Y. Qian, J. Knop, and A. H. Enk. 2003. Induction of CD4+/CD25+ regulatory T cells by targeting of antigens to immature dendritic cells. *Blood* 101:4862-4869; Lohr, J., B. Knoechel, E. C. Kahn, and A. K. Abbas. 2004. Role of B7 in T cell tolerance. *J Immunol* 173:5028-5035).

Figure 4:
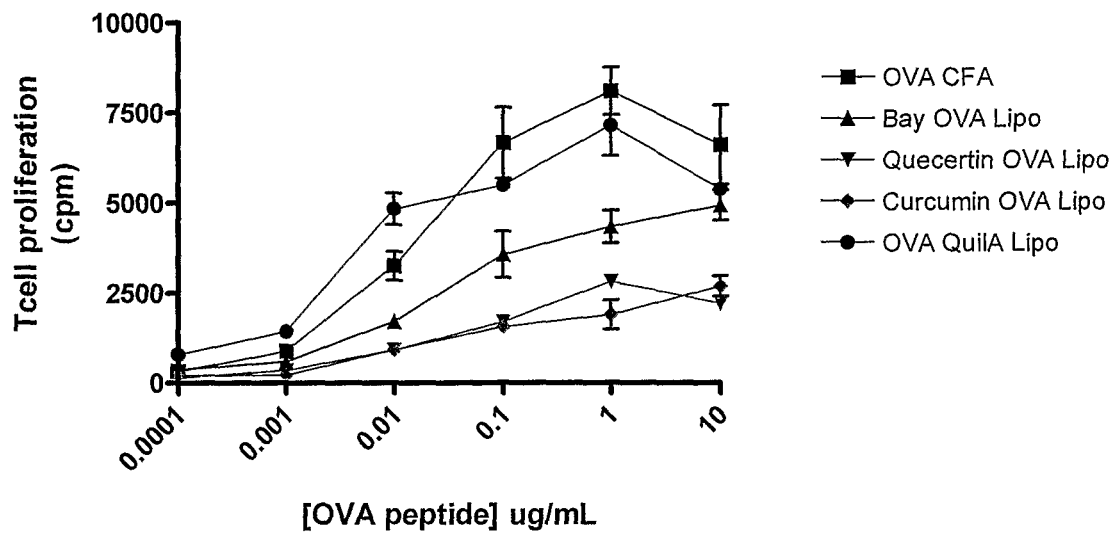
FIG. 4 is a graphical representation showing a suppressed OVA recall response to OVA delivered by liposomes and NF-κB inhibitor. After adoptive transfer of OVA-specific DO11.10 T-cells, Balb/c mice were primed with OVA-CFA. 7 days later, mice were treated with OVA-CFA (red line), liposomes co-entrapping OVA and Bay 11-7082 (blue line), liposomes co-entrapping OVA and quercetin (brown line) liposomes co-entrapping OVA and curcumin (orange line) or liposomes co-entrapping OVA and QuilA (green line). After 7 days post treatment, T-cells were harvested from inguinal lymph node and cultured in RPMI+10% FCS. Using [$^3$H] thymidine incorporation as readout, proliferation of T-cells was evaluated after incubation for 72 hours with naïve DCs and OVA-peptide (323-339) at concentrations varying from 0-10 ug/mL. Mean cpm and error bars as SEM from triplicate wells are shown. Results are representative of two separate experiments.

Effect of NF-κB Inhibitor Co-Entrapped with OVA in Liposomes on OVA-Specific T-Cell Activity after Restimulation with OVA-Peptide Antigen The present inventors tested whether liposomes co-entrapping OVA and NF-κB inhibitors would induce antigen-specific tolerance. To test this, DO11.10 OVA specific TCR transgenic T-cells were transferred to BALB/c mice. These mice were primed 18 h later with OVA and CFA to induce an OVA-specific immune response. 7 days after priming, mice were injected subcutaneously with liposome formulations containing only OVA or OVA and NF-κB inhibitor. 7 days later, the inguinal lymph node was removed and T-cells were enriched using a nylon wool column. Using [$^3$H]thymidine incorporation as a read out, the OVA-specific immune response of T-cells was then evaluated after re-stimulating T-cells with splenic DC purified from naïve syngeneic mice which had been pulsed with OVA-peptide at different concentrations (FIG. 4).

Compared with the positive control OVA-CFA, the OVA-specific response to OVA-liposomes, and OVA-liposomes entrapping NF-κB inhibitors was suppressed. T-cell proliferation was most suppressed in mice administered with OVA-liposomes entrapping either quercetin or curcumin, while suppression was less profound in mice administered with OVA-liposomes alone or entrapping Bay 11-7082. These results further suggest that the inefficiency of liposomes to retain Bay11-7082 may reduce the efficiency with which Bay11-7082 is delivered to target cells, as compared to the highly lipophilic inhibitors curcumin and quercetin.

These results suggest that the suppression of T-cell responses after re-stimulating with OVA-peptide is likely due to the effect of inducing regulatory T cells. Furthermore, the capacity to block NF-κB activation in target APCs correlates with the extent of antigen-specific T cell suppression in this assay, suggesting that liposomes can co-deliver antigen and NF-κB inhibitor to in vivo APCs so that the NF-κB activity of APCs is suppressed, with associated antigen-specific T-cell tolerance.

Figure 5:
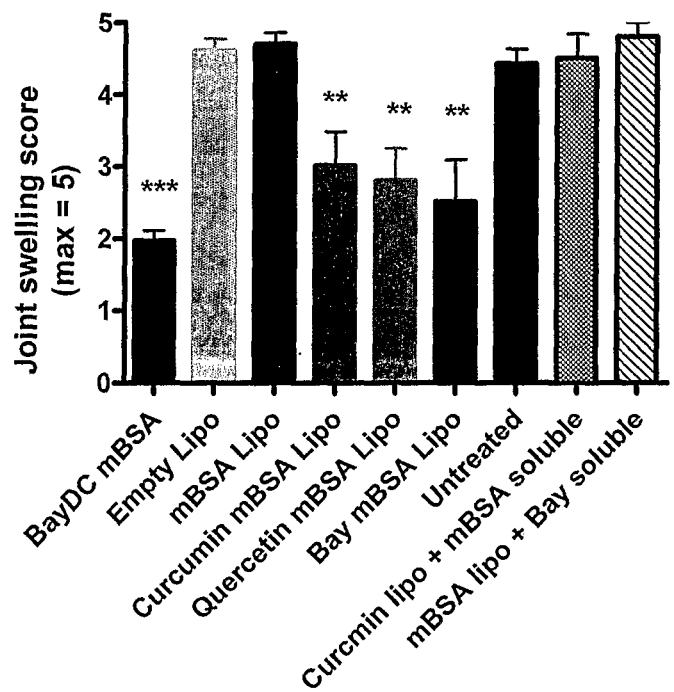
FIG. 5 is a graphical representation showing that liposome particulates containing both antigen and NF-κB inhibitor suppress arthritis in an antigen-specific manner. Antigen induced arthritis (AIA) was induced by priming and boosting with mBSA in complete Freund's adjuvant twice in two weeks, followed by injection of mBSA to one knee joint. 6 days later, when joint swelling was fully clinically expressed, either DC generated in the presence of Bay11-7082 and pulsed with mESA, or liposomes were injected s.c. Joint swelling score was assessed 4 days later by caliper reading. Liposomes were either empty, contained mBSA alone, contained mBSA and curcumin, contained quercetin and mBSA, contained Bay11-7082 and mBSA, contained curcumin alone with soluble mBSA injected adjacent, or contained mBSA alone with soluble Bay11-7082 injected adjacent. p<0.001, *p<0.0001 compared with untreated arthritic mice. Repeated 3 times with 5 mice per group.

Antigen-Specific Suppression of Arthritis by Liposomes is Equivalent to Suppression by DC Treated with an NF-κB Inhibitor To assess the efficacy of liposomes in the suppression of arthritis, antigen induced arthritis (AIA) was induced by priming and boosting with mBSA in complete Freund's adjuvant twice in two weeks, followed by injection of mBSA to one knee joint. 6 days later, when joint swelling was fully clinically expressed, either DC generated in the presence of Bay11-7082 and pulsed with mBSA, or liposomes were injected s.c. to the arthritic mice. Joint swelling score was assessed 4 days later by calipur reading. Liposomes were either empty, contained mBSA alone, contained mBSA and curcumin, contained quercetin and mBSA, contained Bay11-7082 and mBSA, contained curcumin alone with soluble mBSA injected adjacent, or contained mBSA alone with soluble Bay11-7082 injected adjacent (FIG. 5). These data indicate that both liposomes containing both antigen and NF-κB inhibitor combined in a particle, have equivalent efficacy for suppression of acute inflammatory arthritis. However, liposomes containing only one of these components were not effective in suppressing arthritis, even if the other component was injected to adjacent s.c. tissue.

Characterization of Liposomes Entrapping Selected NF-κb Inhibitors and Model Antigens Liposomes are potential carriers for delivery of selected NF-κB inhibitory compounds, particularly if they are lipophilic. To produce immune tolerance towards a specific antigen by targeting a NF-κB inhibitor to phagocytic DC precursors in vivo, the present inventors aimed to co-encapsulate an antigen within NF-κB-loaded liposomes. Several NF-κB inhibitors were chosen for incorporation into liposomes, including Bay11-7082, curcumin and quercetin. The latter two are more lipophilic than Bay11-7082, and hence have greater affinity for the lipid bilayer of liposomes and would be expected to be better retained. Curcumin (1,7-bis(4-hydroxy-3-methoxyphenyl)-1,6-heptadiene-3,5-dione) is a phenolic natural product isolated from the rhizome of *Curcuma longa* (turmeric), which has been shown to exhibit anti-inflammatory and antimutagenic activity, with anti-oxidant properties attributed to the inhibition of several signal transduction pathways in multiple cell types, including p38 MAP kinase and NF-κB (Kim, G. Y., K. H. Kim, S. H. Lee, M. S. Yoon, H. J. Lee, D. O. Moon, C. M. Lee, S. C. Ahn, Y. C. Park, and Y. M. Park. 2005. Curcumin inhibits immunostimulatory function of dendritic cells: MAPKs and translocation of NF-kappaB as potential targets. *J Immunol* 174:8116-8124). Quercetin is a major flavenoid found in fruits such as apricots and mangoes, with similar properties (Kim, B. H., S. M. Cho, A. M. Reddy, Y. S. Kim, K. R. Min, and Y. Kim. 2005. Down-regulatory effect of quercitrin gallate on nuclear factor-kappa B-dependent inducible nitric oxide synthase expression in lipopolysaccharide-stimulated macrophages RAW 264.7. *Biochem Pharmacol* 69:1577-1583).

Liposomes produced from EPC at the concentration of 50 mg/mL were used as a base formulation in the studies reported here. The feasibility of co-encapsulating hydrophilic antigens (specifically OVA and mBSA) within these liposomes together with selected lipophilic NF-κB inhibitors was therefore initially investigated. Multilamellar liposomes were prepared by the conventional thin film method and subjected to freeze-thawing cycles to increase encapsulation efficiency of hydrophilic macromolecules. The resulting liposome samples were subsequently extruded through a 400 nm filter membrane to reduce the particle size for subsequent in vivo evaluation.

Effect of Co-Encapsulation on the Entrapment Efficiency of NF-κB Inhibitor and Antigen Within Liposomes Liposomes co-entrapping NF-κB inhibitor and antigen were characterized for entrapment efficiency, size distribution, zeta potential, and retention of hydrophilic antigen. Despite high entrapment of lipophilic compounds, liposomes prepared by the conventional thin film method without incorporating freeze-thawing cycles exhibit relatively low entrapment efficiency for hydrophilic molecules. For instance, previous experiment using the same condition and EPC lipid concentration to entrap FITC-OVA reported the entrapment efficiency of less than 5% (Copland, M. J., M. A. Baird, T. Rades, J. L. McKenzie, B. Becker, F. Reck, P. C. Tyler, and N. M. Davies. 2003. Liposomal delivery of antigen to human dendritic cells. *Vaccine* 21:883-890). In comparison and in the present study, inclusion of a freeze-thawing cycle repeated 5 times increased the entrapment of OVA to almost 20%. These results demonstrate that the inclusion of freeze-thawing cycles in the preparation process substantially increase the encapsulating efficiency of hydrophilic compounds.

The entrapment efficiencies of mBSA (approximately 25%) were slightly higher than that of OVA. This may be attributed to the methylation of BSA which presumably increases its lipophilicity. This increased lipophilicity may thus play a role in the high entrapment of mBSA compared to OVA. Further, it has been previously reported that albumin proteins from different sources interact with liposomes to different extents (Dimitrova, M. N., H. Matsumura, A. Dimitrova, and V. Z. Neitchev. 2000. Interaction of albumins from different species with phospholipid liposomes. Multiple binding sites system. *Int J Biol Macromol* 27::187-194). This was attributed to the differences in amino acid sequences, leading to differences in surface properties of proteins and hence protein-liposome interaction.

No statistically significant variation in entrapment of either OVA or mBSA as a result of co-entrapment of NF-κB inhibitors could be observed ($p>0.05$) although in all cases entrapment of OVA was slightly higher in liposomes co-encapsulating NF-κB than in those not containing inhibitor. Further, when comparing liposomes loaded with the same NF-κB inhibitor, there was no significant difference in entrapment efficiency of NF-κB inhibitor whether liposomal formulations were prepared with OVA or mBSA ($p>0.05$). Entrapment efficiency of the highly lipophilic compounds, quercetin and curcumin (log $P>3$) was greater than 80%, while that of the less lipophilic Bay11-7082 (log P of 1.63) was lower, at around 60%.

The lack of relationship between antigen and NF-κB inhibitor on liposomal entrapment was expected. The lipophilic NF-κB inhibitors are likely entrapped within the lipid bilayer, interacting with aliphatic chains of the phospholipids via hydrophobic interactions, with their polar functional groups interacting with the polar heads of the phospholipids. In contrast, hydrophilic antigens are expected to be encapsulated within the aqueous domains, although some interaction with the surface of the lipid bilayer is likely as a result of the surface-active nature of proteins. Hence, little interaction is likely to occur between the lipophilic NF-κB inhibitors and the hydrophilic antigens upon encapsulation within liposomes, resulting in their lack of interaction in terms of respective entrapment efficiencies. These results demonstrate that liposomes are suitable for co-delivery of NF-κB inhibitors and antigens, which largely differ in terms of both hydro/lipophilicity and molecular size.

Effect of Co-Encapsulation on the Particle Size, Polydispersity and Zeta Potential of Liposome Entrapping Antigens and NF-κB Inhibitor Except for quercetin, the particle sizes of liposomes co-entrapping mBSA and NF-κB inhibitors were around 350 nm. This was similar and not statistically different (p>0.05) to the size of liposomes encapsulating NF-κB inhibitors without antigen. However, regardless of the entrapped NF-κB inhibitor, the particle sizes of liposome entrapping OVA were slightly larger than liposomes entrapping mBSA (409.9±16.9 vs 328.7±22.0 nm for the liposome without NF-κB inhibitor) and liposomes without antigens. It was noted that liposomes prepared with OVA were less easy to extrude and consequently the protocol of simply extruding through 400 nm membranes (10 cycles) was changed to sequential extrusion through first 800 nm membranes (5 cycles) and then 400 nm membranes (5 cycles) for OVA liposomes.

Liposomes co-entrapping quercetin together with antigens had a larger particle size than liposomes co-entrapping other NF-κB inhibitors and antigen (p<0.05). The reasons for the increase in observed size are likely due to the insertion of quercetin into the bilayer, affecting the packing parameter of the bilayer lipids as well as the interaction of quercetin with the lipid polar head groups via hydrogen bonding.

There was no significant difference in the zeta potential of liposomes entrapping OVA or mBSA (p>0.05). Further, when compared to liposomes encapsulating only NF-κB inhibitor, the encapsulation of antigens did not affect the zeta potential of these liposomal formulations (p>0.05). Again, considering the location of the antigen within the interior aqueous domains of the liposomes, encapsulation of antigen would not be expected to alter the charge on the surface of liposomes and hence zeta potential. The lack of change in zeta potential would suggest however, that neither antigen is appreciably adsorbed onto the exterior surface of liposomes following removal of non-encapsulated antigen by centrifugation.

Taken together, these results indicate that the incorporation of either antigen did not significantly change the physical properties of NF-κB inhibitor loaded liposomes in terms of size, size distribution and zeta potential when compared to liposomes entrapping only NF-κB inhibitors.

Stability of Liposomal Formulations Co-Entrapping NF-κB Inhibitor and Antigen

The stability of liposomes co-entrapping antigen and NF-κB inhibitors in terms of particle size upon storage at 4° C. for 7 days (conditions used for storage of formulations as required prior to in vivo evaluation) was investigated. The results indicate that liposomes co-entrapping antigen and NF-κB inhibitor are physically stable when stored under these conditions for at least 7 days. Therefore, all liposomal formulations were stored at 4° C. and used within 7 days of preparation.

Retention of Antigen Entrapped in Liposomes Containing Different NF-κB Inhibitors When liposomes are used as carriers to deliver bioactive compounds in vivo, hydrophilic compounds, particularly small molecules, entrapped in the aqueous core may be rapidly lost following administration (e.g., by intravenous injection) because of the interaction of liposomes with serum components such as lipoproteins (Jones, M. N., and A. R. Nicholas. 1991. The effect of blood serum on the size and stability of phospholipid liposomes. *Biochim Biophys Acta* 1065:145-152; Harashima, H., T. M. Huong, T. Ishida, Y. Manabe, H. Matsuo, and H. Kiwada. 1996. Synergistic effect between size and cholesterol content in the enhanced hepatic uptake clearance of liposomes through complement activation in rats. *Pharm Res* 13:1704-1709; Maurer, N., D. B. Fenske, and P. R. Cullis. 2001. Developments in liposomal drug delivery systems. *Expert Opin Biol Ther* 1:923-947). It has been shown that liposomes can be destabilized by the transfer of phospholipids from the liposomal membranes to high density (HDL) and low density lipoproteins (LDL), resulting in leakage of encapsulated drug (Allen, T. M. 1981. A study of phospholipid interactions between high-density lipoproteins and small unilamellar vesicles. *Biochim Biophys Acta* 640:385-397; Scherphof, G., F. Roerdink, M. Waite, and J. Parks. 1978. Disintegration of phosphatidylcholine liposomes in plasma as a result of interaction with high-density lipoproteins. *Biochim Biophys Acta* 542:296-307; Hunter, J. A., Z. Shahrokh, T. M. Forte, and A. V. Nichols. 1982. Aggregation of low density lipoproteins with unilamellar phosphatidylcholine vesicles. *Biochem Biophys Res Commun* 105:828-834). The presence of only 10% FBS in an incubating medium was reported to dramatically induce leaking of liposomal contents and as such, can be used as an indication of the serum stability of liposomes (Allen, T. M., and L. G. Cleland. 1980. Serum-induced leakage of liposome contents. *Biochim Biophys Acta* 597:418-426).

The susceptibility of liposomes to destabilization in serum is particularly influenced by the fluidity of the liposomal membrane. Liposomes composed of saturated phospholipid with high $T_c$, such as DSPC have been reported to have enhanced stability and consequently reduced leakage of solutes in plasma (Hao, Y. L., Y. J. Deng, Y. Chen, X. M. Wang, H. J. Zhong, and X. B. Suo. 2005. In vitro and in vivo studies of different liposomes containing topotecan. *Arch Pharm Res* 28:626-635; Clary, L., G. Verderone, C. Santaella, and P. Vierling. 1997. Membrane permeability and stability of liposomes made from highly fluorinated double-chain phosphocholines derived from diaminopropanol, serine or ethanolamine. *Biochim Biophys Acta* 1328:55-64; Senior, J., and G. Gregoriadis. 1982. Stability of small unilamellar liposomes in serum and clearance from the circulation: the effect of the phospholipid and cholesterol components. *Life Sci* 30:2123-2136; Gregoriadis, G., and J. Senior. 1980. The phospholipid component of small unilamellar liposomes controls the rate of clearance of entrapped solutes from the circulation. *FEBS Lett* 119:43-46). The inclusion of cholesterol in the liposomal formulation has also been shown to improve the stability of the bilayer by increasing the packing density of lipids (Allen, T. M., and L. G. Cleland. 1980. Serum-induced leakage of liposome contents. *Biochim Biophys Acta* 597:418-426, Kirby, C., J. Clarke, and G. Gregoriadis. 1980. Effect of the cholesterol content of small unilamellar liposomes on their stability in vivo and in vitro. *Biochem J* 186:591-598). In addition, the presence of cholesterol in the liposomal structure has been shown to inhibit transfer of phospholipids to HDL (Damen, J., J. Regis, and G. Scherphof. 1981. Transfer and exchange of phospholipid between small unilamellar liposomes and rat plasma high density lipoproteins. Dependence on cholesterol content and phospholipid composition. *Biochim Biophys Acta* 665:538-545).

In the current studies, the model liposomal formulations were composed of EPC without cholesterol. It was decided therefore to determine whether the liposomal formulations are stable and capable of retaining their contents, particularly entrapped antigens, in the presence of serum. FITC-OVA was used as the antigen to be entrapped in various NF-κB inhibitor-loaded liposomes, which were suspended in HEPES buffer pH 7.4 supplemented with 10% FBS. The release of FITC-OVA was monitored over 28 hrs at 37° C., and compared to the release from liposomes incubated in buffer without FBS under the same conditions.

Figure 6:
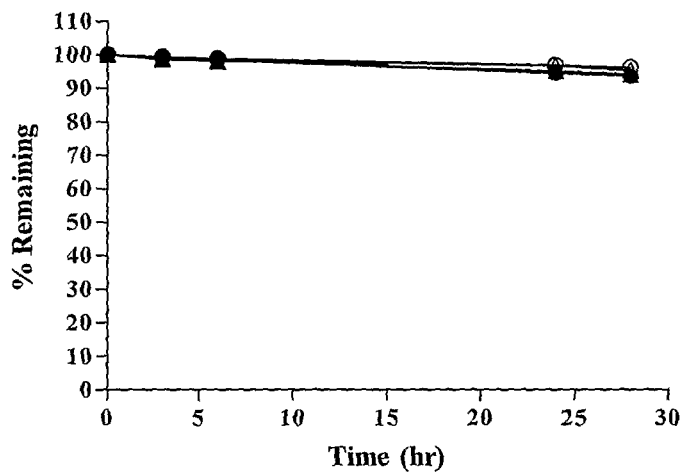
FIG. 6 is a graphical representation showing retention of FITC-OVA in various NF-κB inhibitors loaded liposomes. Liposomes entrapping only FITC-OVA (●), liposomes co-entrapping FITC-OVA and Bay 11-7082 (▲), liposomes co-entrapping FITC-OVA and quercetin (Δ) and liposomes co-entrapping FITC-OVA and curcumin (○) were incubated in HEPES buffer pH 7.4 (A) or HEPES buffer pH 7.4+10% FBS (B) at 37° C. The release of FITC-OVA was monitored over 28 hours by fluorescence spectrophotometry. Data represent mean and SD of three experiments.
Figure 6:
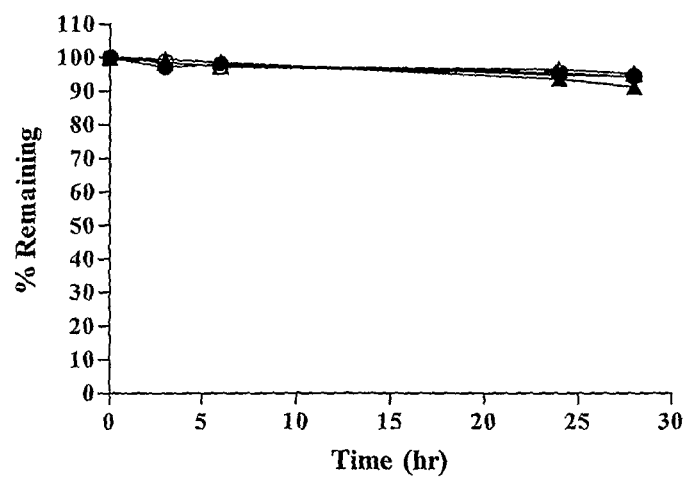

The release profiles of FITC-OVA from various NF-κB inhibitor-loaded liposomes are shown in FIG. 6. More than 90% of FITC-OVA was retained in liposomes after 28 hours incubation in the presence of 10% FBS at 37° C. irrespective of co-entrapped NF-κB inhibitors. Further, there was no significant difference between liposomes incubated with or without FBS. The satisfactory retention of entrapped antigen within liposomes upon incubation with FBS may be due to the large molecular structure of the antigen, hindering its diffusion out of the liposome.

Example 2

Either Antigen-Associated Liposomes or Microspheres Induce Antigen-Specific Suppression by Induction of Regulatory T Cells Materials and Methods Reagents Poly(d,l-lactic-co-glycolic acid (PLGA) microspheres were prepared by combining ovalbumin, curcumin, PLGA and poly vinyl alcohol (PVA) then homogenizing 13500 rpm, followed by stirring at 800 rpm. After density centrifugation, the particles were dispersed in 5% w/v sucrose solution, sized and lyophilized. Before use, particles were reconstituted in PBS. OVA-curcumin liposomes were prepared as described in Example 1.

In Vivo Model to Test Antigen-Specific Suppression

DO11.10 mice were primed with OVA and complete Freunds adjuvant (CFA) and 7 days later injected with either curcumin-OVA liposomes or curcumin-OVA microspheres. After 7 days, splenocytes from these mice were purified and transferred to BALB/c recipients which had been primed with OVA and CFA 7 days earlier. Recipient mice were sacrificed after 5 days and splenocytes were restimulated with varying concentrations of OVA peptide.

Results

Figure 7:
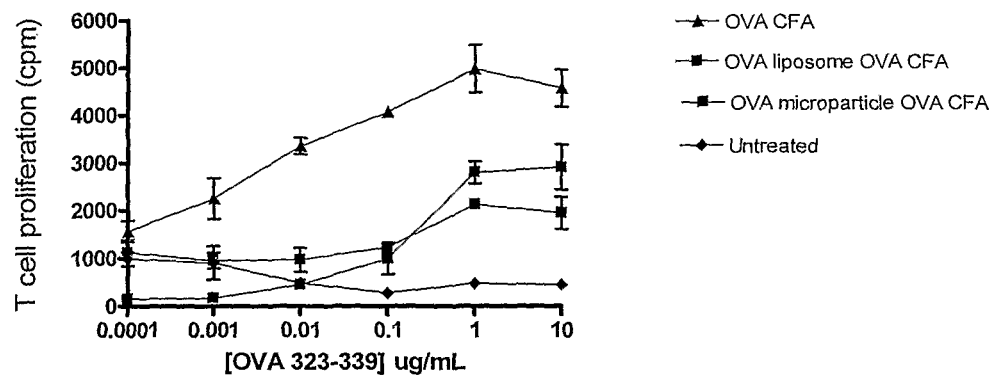
FIG. 7 is a graphical representation showing that either OVA curcumin-liposomes or OVA-curcumin-microspheres induce regulatory T cells. DO11.10 mice were primed with OVA and complete Freunds adjuvant and 7 days later injected with either curcumin-OVA liposomes or curcumin-OVA polymeric microparticles. After 7 days, splenocytes were purified and transferred to primed BALB/c recipients. Mice were sacrificed after 5 days and splenocytes were restimulated with varying concentrations of OVA peptide.

Either Antigen-Associated Liposomes or Microspheres Induce Antigen-Specific Suppression by Induction of Regulatory T Cells Splenocytes from OVA/CFA-primed mice which received OVA-specific DO11.10 T cells from OVA/CFA primed mice responded well to OVA peptide restimulation (FIG. 7, red line). In contrast, when donors of DO11.10 T cells had been primed with OVA/CFA then treated with OVA-curcumin liposomes (green line) or microspheres (blue line), the splenocyte response from recipient mice was suppressed. As a negative control, splenocytes from unprimed mice responded poorly to OVA peptide (black line). These data indicate that either liposomes or microspheres encapsulating OVA and NF-kB inhibitor could lead to suppression of a previously primed response to OVA. Suppression can be transferred by T cells from one animal to the next—an indicator that regulatory T cells have been induced (Martin E, O'Sullivan B J, Low P and R Thomas. Antigen-specific suppression of a primed immune response by dendritic cells mediated by regulatory T cells secreting interleukin-10. Immunity 2003. 18:155-67.)

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe certain embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for eliciting a tolerogenic immune response to a target antigen in a subject, comprising administering to the subject an NF-κB inhibitor and an antigen that corresponds to at least a portion of the target antigen, wherein the inhibitor and the antigen are contained in at least one particle capable of being taken up by an immune cell and wherein the at least one particle is a liposome or a polymeric microsphere.

2. A method according to claim 1, wherein the particle is a liposome.

3. A method according to claim 1, wherein the particle is a polymeric microsphere and comprises a poly(lactide-co-glycolide).

4. A method according to claim 1, wherein the antigen is selected from allergens, autoantigens and alloantigens.

5. A method according to claim 1, wherein the antigen is a proteinaceous antigen.

6. A method according to claim 4, wherein the autoantigen is selected from the group consisting of lupus autoantigen, Smith, Ro, La, U1-RNP, fibrillin; nuclear antigens, histones, glycoprotein gp70 and ribosomal proteins; pyruvate dehydrogenase dehydrolipoamide acetyltransferase (PCD-E2); hair follicle antigens; human tropomyosin isoform 5 (hTM5); proinsulin, insulin, IA2 and GAD65; collagen type II, human cartilage gp 39 (HCgp39) and gp130-RAPS, dnaJp1, citrullinated proteins and peptides, citrullinated type II collagen, citrullinated vimentin and citrullinated fibrinogen; myelin basic protein, proteolipid protein (PLP) and myelin oligodendrocyte glycoprotein (MOG); thyroid stimulating factor receptor (TSH-R); acetylcholine receptor (AchR); gliadin; histones, PLP, glucose-6-phosphate isomerase, thyroglobulin, tRNA synthetases, proteinase-3 and myeloperoxidase.

7. A method according to claim 1, wherein the antigen is in a non-nucleic acid form.

8. A method according to claim 1, wherein the NF-κB inhibitor decreases the level or functional activity of RelB.

9. A method according to claim 8, wherein the NF-κB inhibitor is selected from quecertin, curcumin and Bay 11-7082.

10. A method according to claim 1, wherein the NF-κB inhibitor is in a non-nucleic acid form.

11. A method according to claim 1, wherein the composition is administered subcutaneously.

* * * * *